US011519021B2

(12) United States Patent
Burn et al.

(10) Patent No.: US 11,519,021 B2
(45) Date of Patent: Dec. 6, 2022

(54) METHODS OF IDENTIFYING MICROSATELLITE INSTABILITY

(71) Applicant: Cancer Research Technology Limited, London (GB)

(72) Inventors: John Burn, Newcastle Upon Tyne (GB); Mohammed Ghanim Mehdi Alhilal, Baghdad (IQ); Francisco Mauro Santibanez-Koref, Newcastle Upon Tyne (GB); Lisa Redford, Hagan (NO); Michael Stewart Jackson, Newcastle Upon Tyne (GB)

(73) Assignee: CANCER RESEARCH TECHNOLOGY LIMITED

( * ) Notice: Subject to any disclaimer, the term of this patent is extended or adjusted under 35 U.S.C. 154(b) by 393 days.

(21) Appl. No.: 16/327,847

(22) PCT Filed: Aug. 23, 2017

(86) PCT No.: PCT/GB2017/052488
§ 371 (c)(1),
(2) Date: Feb. 24, 2019

(87) PCT Pub. No.: WO2018/037231
PCT Pub. Date: Mar. 1, 2018

(65) Prior Publication Data
US 2019/0194731 A1 Jun. 27, 2019

(30) Foreign Application Priority Data

Aug. 24, 2016 (GB) ..................... 1614474

(51) Int. Cl.
*C12Q 1/6827* (2018.01)
*C12Q 1/686* (2018.01)
*C12Q 1/6869* (2018.01)

(52) U.S. Cl.
CPC .......... *C12Q 1/6827* (2013.01); *C12Q 1/686* (2013.01); *C12Q 1/6869* (2013.01); *C12Q 2531/119* (2013.01); *C12Q 2535/119* (2013.01); *C12Q 2535/122* (2013.01); *C12Q 2537/143* (2013.01); *C12Q 2600/16* (2013.01)

(58) Field of Classification Search
CPC ..................................................... C12Q 1/686
See application file for complete search history.

(56) References Cited

U.S. PATENT DOCUMENTS

| 2012/0295267 A1 | 11/2012 | Goel et al. |
| 2015/0045369 A1 | 2/2015 | Lambrechts |
| 2016/0040254 A1 | 2/2016 | Garner et al. |

FOREIGN PATENT DOCUMENTS

| JP | 2008517606 A | 5/2008 |
| JP | 2015516144 A | 6/2015 |
| WO | 2016127067 A1 | 8/2016 |

OTHER PUBLICATIONS

Bonneville, R. et al., Landscape of Microsatellite Instability Across 39 Cancer Types, JCO Precision Oncology, DOI: 10.1200./PO.17.00073, pp. 1-15 (Year: 2017).*
Affymetrix, "Data Sheet Affymetrix(R) Genome-Wide Human SNP Array 6.0", Internet Citation,(2007), pp. 1-4,URL:http://www.affymetrix.com/support/technical/datasheets/genomewide_snp6_datasheet.pdf, (Apr. 10, 2009).
XP-002774860, Database, dbsnp, Submitted SNP(ss) Details: ss337001895, dbsnp, (Jul. 20, 2011), Database accession No. ss337001895.
Written Opinion in PCT Application No. PCT/GB2017/052488, dated Nov. 2, 2017.
International Preliminary Report on Patentability in PCT Application No. PCT/GB2017/052488, dated Feb. 26, 2019.
Vieux E.F. et al., "Primer Design for PCR and Sequencing in High-Throughput Analysis of SNPs", BioTechniques (2002), vol. 32, pp. S28-S32.
Redford L. et al., "A novel panel of short mononucleotide repeats linked to informative polymorphisms enabling effective high volume low cost discrimination between mismatch repair deficient and proficient tumours". PLoS One, (2018), vol. 13, No. 8, pp. 1-21.
Burn, J., et al., "Long-term effect of aspirin on cancer risk in carriers of hereditary colorectal cancer: an analysis from the CAPP2 randomised controlled trial", Lancet, (2011) pp. 378, 2081-2087.
Cancer Genome Atlas Network. (2012). Comprehensive molecular characterization of human colon and rectal cancer. Nature 487, 330-337.
Li, H., "Toward better understanding of artifacts in variant calling from highcoverage samples". Bioinformatics, (2014) vol. 30, pp. 2843-2851.

(Continued)

*Primary Examiner* — Teresa E Strzelecka
(74) *Attorney, Agent, or Firm* — Troutman Pepper Hamilton Sanders LLP

(57) ABSTRACT

The present invention relates to methods and kits for identifying microsatellite instability (MSI) in a sample. In particular it relates to identifying microsatellite instability in a tumor sample, which may be from a subject suspected of having colorectal cancer or Lynch syndrome. The methods and kits can be used to identify mismatch repair defects. More particularly the invention relates to a panel of markers for a sequencing based MSI test, that can differentiate between MSI-H and MSS CRCs. The invention also allows for determination of biological significance, differentiating between PCR and sequencing errors and MSI induced indels/mutations.

13 Claims, 7 Drawing Sheets

Specification includes a Sequence Listing.

(56) References Cited

OTHER PUBLICATIONS

O'Rawe, J., et al., "Low concordance of multiple variant-calling pipelines: practical implications for exome and genome sequencing", (2013) Genome Med, 5:28, pp. 1-18.
Pabinger, S., et al., "A survey of tools for variant analysis of next-generation genome sequencing data. Brief Bioinform", (2013) vol. 15, No. 2, pp. 256-278.
Houniet, D. T., et al., Using population data for assessing next-generation sequencing performance. Bioinformatics, (2015) vol. 31, No. 1, pp. 56-61.
Minoche, A. E., et al., "Evaluation of genomic high-throughput sequencing data generated on Illumina HiSeq and genome analyzer systems", Genome Biol, (2011) 12, R112 pp. 1-15.
De la Chapelle, A., et al., "Clinical relevance of microsatellite instability in colorectal cancer." Journal of Clinical Oncology ((2010), vol. 28, pp. 3380-3387.
Laiho, P., et al., "Low-level microsatellite Instability in Most Colorectal Carcinomas", Cancer Research (2002), 62, pp. 1166-1170.
Boyle, T.A., et al., "Summary of microsatellite instability test results from laboratories participating in proficiency surveys: proficiency survey results from 2005 to 2012" Arch Pathol Lab Med (2014) vol. 138, pp. 363-370.
Shinde, D., et al., "Taq DNA polymerase slippage mutation rates measured by PCR and quasi-likelihood analysis: (CA/GT)n and (A/T)n microsatellites", Nucleic Acids Research, (2003) vol. 31, No. 3, pp. 974-980.
Umar, A., et al., "Revised Bethesda Guidelines for hereditary nonpolyposis colorectal cancer (Lynch syndrome) and microsatellite instability", Journal of the National Cancer Institute (2004) 96, pp. 261-268.
Shia, J. "Immunohistochemistry versus microsatellite instability testing for screening colorectal cancer patients at risk for hereditary nonpolyposis colorectal cancer syndrome. Part I. The utility of immunohistochemistry" (2008) The Journal of molecular diagnostics vol. 10, No. 4, pp. 293-300.
Zhang, L. "Immunohistochemistry versus microsatellite instability testing for screening colorectal cancer patients at risk for hereditary nonpolyposis colorectal cancer syndrome. Part II. The utility of microsatellite instability testing", The Journal of molecular diagnostics (2008) vol. 10, No. 4, pp. 301-307.
Niu, B., et. al., "MSIsensor: microsatellite instability detection using paired tumor-normal sequence data. Bioinformatics", (2014) vol. 30, No. 7, pp. 1015-1016.
Lu, Y., et al., A novel approach for characterizing microsatellite instability in cancer cells.: PLoS One (2013) vol. 8, e63056, pp. 1-10.
Salipante, S.J., et al., "Microsatellite instability detection by next generation sequencing" Clin Chem (2014). 60, 1192-1199.
Ananda, G., et al., "Distinct mutational behaviors differentiate short tandem repeats from microsatellites in the human genome" Genome Biol Evol (2013) 5, 606-620.
Snowsill, T., et al., "Distinct mutational behaviors differentiate short tandem repeats from microsatellites in the human genome" Genome Biol Evol (2013) 5, 606-620.
International Search Report in PCT Application No. PCT/GB2017/052488, dated Nov. 2, 2017.
Singapore Search Report Application No. 11201901620S, search completed Jun. 1, 2020.
Singapore Written Opinion Application No. 11201901620S completed Jun. 1, 2020.
NICE "Molecular testing strategies for Lynch syndrome in people with colorectal cancer" (2017)[https://www.nice.org.uk/guidance/dg27] (accessed Oct. 4, 2017).
Yoon, K., et al., "Comprehensive genome- and transcriptome-wide analyses of mutations associated with microsatellite instability in Korean gastric cancers" Genome Res, (2013) 23, 1109-17.
Kent, W. J., et al. "The human genome browser at UCSC" Genome Res, (2002) 12, 996-1006.
Rozen, S. et al., "Primer3 on the WWW for general users and for biologist programmers", Methods Mol Biol, (2000) 132, 365-86.
Alhopuro, P., et al., "Unregulated smooth-muscle myosin in human intestinal neoplasia", Proceedings of the National Academy of Sciences of the United States of America (2008) 105, 5513-5518.
Sammalkorpi, H., et al., "Background mutation frequency in microsatellite-unstable colorectal cancer", Cancer Res (2007) 67, 5691-5698.
Boland, C.R., et al., "Microsatellite instability in colorectal cancer. Gastroenterology" (2010) 138, 2073-2087 e2073.
Hiatt et al., "Genome Research" (2013) 23(5):843-54. (http://genome.cshlp.org/content/23/5/843.long ).
Li, H., et al., "Fast and accurate short read alignment with Burrows-Wheeler transform", Bioinformatics (2009) 25, 1754-1760.
Li, H., et al., "The Sequence Alignment/Map format and SAMtools", Bioinformatics (2009) 25, 2078-2079.
DePristo, M.A., "A framework for variation discovery and genotyping using next-generation DNA sequencing data", Nature genetics (2011) 43, 491-498.
Sherry, S.T., et al., "dbSNP: the NCBI database of genetic variation", Nucleic acids research (2001) 29, 308-311.

\* cited by examiner

METHODS OF IDENTIFYING MICROSATELLITE INSTABILITY

The present invention relates to methods and kits for identifying microsatellite instability (MSI) in a sample. In particular it relates to identifying microsatellite instability in a tumor sample, which may be from a subject suspected of having colorectal cancer or Lynch syndrome. The methods and kits can be used to identify mismatch repair defects. More particularly the invention relates to a panel of markers for a sequencing based MSI test, that can differentiate between MSI-H and MSS CRCs. The invention also allows for determination of biological significance, differentiating between PCR and sequencing errors and MSI induced indels/mutations.

BACKGROUND

Mismatch Repair and Microsatellite Instability

Microsatellites are regions of genomic DNA comprising simple repetitive sequences or tandem repeats with repeat units of typically 1-6 bp which are repeated, often 5-50 times. Microsatellite loci are classified based on the length of the smallest repetitive unit. For example, loci with repetitive units of 1 to 5 base pairs in length are termed "mono-nucleotide", "di-nucleotide", "tri-nucleotide", "tetra-nucleotide", and "penta-nucleotide" repeat loci, respectively.

Microsatellite loci of normal genomic DNA for most diploid species, e.g. genomic DNA from mammals such as humans, consists of two alleles at each locus. Microsatellite alleles are normally maintained at constant length in a given individual and its descendants, however instability in the length of microsatellites has been observed in some tumors. In particular, microsatellites are known to be unstable during meiotic and mitotic replication in eukaryotes and prokaryotes. Factors which affect the susceptibility of microsatellites to slippage events include the length of the microsatellite, repeat unit length, base composition, and the sequence surrounding a microsatellite. For example, closely situated mononucleotide repeats are more mutable than single mononucleotide repeats of the same. Microsatellite instability (MSI) occurs due to a failure to correct DNA replication errors as a result of defects in mismatch repair (MMR) genes. Testing for MSI in tumours is therefore used to identify MMR gene defects.

Traditional mononucleotide and dinucleotide repeats have been used in MSI tests. Tri-, tetra-, and pentanucleotide repeats are less desirable in an MSI test because they show a low mutability in MSI-H tumours. Also, one cause of tetra nucleotide repeat instability, also known as Elevated Microsatellite Alterations at Selected Tetranucleotide repeats (EMAST), is believed to a consequence of inflammation, and research suggests that this instability is reversible in tumours and thus is not a good marker.

Colorectal Cancer (CRC)

The third most common cancer type in 2012 was colorectal cancer (CRC) with ~1.4 million new cases and ~694,000 deaths. Colorectal cancers therefore constitute 9.7% of the world's cancer burden. There is an increasing rate of colorectal cancers in high and middle human development index (HDI) areas and this is believed to be because there is an increased risk of colorectal cancer associated with alcohol consumption, smoking, obesity, diabetes, the consumption of large amounts of meat, and little physical activity.

There are different types of CRC which are traditionally divided into two groups, those with chromosome instability and those with mismatch repair gene defects. Chromosome instability is the most common cause of colon cancer accounting for approximately 85% of CRCs and these cancers are characterized by the gain or loss of chromosomes and chromosome parts, the amplification of genes, and chromosome translocations. Chromosome instability can occur due to defects that affect the mitotic checkpoint. Another cause of chromosome instability is abnormal centrosome function, which can also lead to unequal chromosome segregation. Other mechanisms that can cause chromosome instability include telomere dysfunction, which can lead to chromosomes breaking and fusing during mitosis, and problems with the mitotic cell cycle arrest response that can lead to DNA damage not being repaired.

The other 15% of CRCs have mismatch repair gene defects and are characterized by microsatellite instability (MSI), which can be defined as somatic changes in the length of microsatellites. Microsatellites are repetitive regions of DNA that are scattered throughout the genome. Because of their repetitive nature, polymerases are more likely to cause slippage in the form of insertions and deletions while replicating microsatellites compared to other regions of DNA. Defects in mismatch repair genes cause microsatellite instability (MSI) because errors during DNA replication are not rectified by the cell's compromised mismatch repair system. The DNA mismatch repair system is also a part of the mechanism that causes cell death when the mutation burden becomes too high. This function is also lost with a compromised mismatch repair system. A compromised mismatch repair system can, through these two mechanisms, lead to a high mutation burden which can cause cancer. MSI will cause tumorigenesis through mutations in genes that contain coding microsatellites. Two examples of such genes are TGFBR2 and BAX.

Based on microsatellite status, colorectal tumours can be divided into 3 the categories; tumours with high levels of microsatellite instability (MSI-H), tumours with low levels of microsatellite instability (MSI-L), and tumours that are microsatellite stable (MSS). Tumours with mismatch repair defects have high levels of microsatellite instability and are categorised as MSI-H tumours. MSS tumours are usually tumours associated with chromosome instability. MSI-L tumours also appear to arise as a result of chromosome instability. The MSI-L category has been widely used, but there is debate over whether there is a qualitative difference between MSI-L and MSS tumours and if MSI-L tumours can be considered a discrete group.

A recent molecular classification has identified four molecular sub groups. The distinction of tumours with a breakdown in mismatch repair is still evident; they demonstrated marked inter connectivity across 6 different classification systems and distilled the groups into four consensus molecular subtypes: CMS1 Microsatellite instability, immune (14%) CMS2 Canonical (37%) ⍰ CMS3 Metabolic (13%) ⍰ CMS4 Mesenchymal (23%). Tumours which could not be classified into one of these groups were deemed to represent a transitional phenotype or intratumoural heterogeneity.

Lynch Syndrome and Sporadic Microsatellite Unstable Tumours

Lynch syndrome, formerly known as hereditary non polyposis colorectal cancer (HNPCC), is a hereditary form of autosomal dominant colon cancer which results from inherited mismatch repair gene defects and is characterized by high levels of microsatellite instability. Throughout this document Lynch Syndrome will be included when reference to cancer are made. Lynch Syndrome constitutes 20% of MSI-H CRCs. Mutations in the MLH1, MSH2, MSH6, PMS2 and PMS1 genes can cause Lynch Syndrome. A deletion in the EPCAM gene upstream of MSH2 can cause the knockout of MSH2 and has also been shown to be a pathogenic mutation in some Lynch Syndrome patients. Patients with Lynch Syndrome develop their first cancer early, on average in their mid forties, unlike patients with sporadic MSI-H cancers where the average age is over seventy. In addition to an increased risk of CRC, Lynch Syndrome is associated with an elevated risk of endometrial cancer, bladder cancer, and tumors of the small intestine, ovary, urinary tract, stomach, biliary tract, pancreas, brain, and sebaceous glands. The risk of developing CRC by the age of 70 years has been estimated at 66% for men, and for women the risk of developing a colorectal or endometrial cancer is estimated at 73%.

Sporadic MSI-H tumours are usually caused by the epigenetic silencing of MLH1 caused by promoter methylation. Whereas Lynch Syndrome tumours have been thought to arise from adenomas sporadic MSI-H CRCs arise from serrated polyps. More recently, the sessile serrated adenoma with its indistinct edges, mucus cap and characteristic "saw tooth" histology has become the primary suspect for the high prevalence of ascending colon "interval cancers" arising between frequent screening colonoscopies.

Approximately 80% of MSI-H tumours are sporadic tumours. Sporadic MSI-H tumours, in addition to having on average a later age of onset compared to Lynch Syndrome tumours, also have predisposition for the proximal colon and are more common in women than men.

It is clear therefore that knowledge of MSI status is useful as it can define hereditary forms of CRC and inform clinical care. Identifying patients with Lynch Syndrome is important as they and their relatives have a high risk of developing second primary cancers. Early detection of these cancers has a significant impact upon prognosis, and it has been estimated that more than 60% of Lynch Syndrome cancer deaths could be prevented with proper follow up. In addition, survival rates may be improved further by prophylactic use of aspirin, as its daily use for >2 years has been shown to reduce Lynch Syndrome cancer rates by ~60% (Burn et al. (2011).

MSI is usually detected by PCR amplification of a panel of five >20 bp microsatellite markers, with alleles being resolved using fragment analysis. MMR defects can also be detected by immunohistochemistry staining. BRAF-V600E mutation screening of MSI-H tumours can be used to narrow down which patients may have Lynch Syndrome and save screening costs because the BRAF mutation rarely occurs in Lynch Syndrome patients but is very common in sporadic MSI-H CRCs. Sequence based MSI typing could be advantageous in terms of cost and ease of interpretation through automation. However, long microsatellites are not amenable to sequence analysis, and although some short (6-14 bp) mononucleotide repeats have been identified which exhibit instability, the frequencies of instability are highly variable.

Recently, however, it has been reported that current clinical criteria and management guidelines used to identify CRC patients for MSI testing (Amsterdam II criteria and revised Bethesda Guidelines) fail to identify a significant number of Lynch Syndrome patients. This has led to suggestions that all CRC and endometrial tumours should receive molecular testing.

It is generally the case that MSI-H is a predictor of a better prognosis in CRCs compared to MSS. Further, MSI-H CRCs, whether sporadic or inherited, respond similarly to many different drugs. This will be due to the mismatch repair system being knocked out in both cancer types. A test for MSI-H CRCs would therefore allow appropriate treatment to be allocated.

Another compelling reason for MSI testing of all CRC and endometrial tumors is that microsatellite stable (MSS) and MSI-H tumours respond differently to different types of chemotherapy, and treatment can be tailored based on a tumor's MSI status. In 2015 a major study of the drug pembrolizumab showed startling benefits in MMR deficient colorectal cancers with a highly significant beneficial effect in cases of metastatic disease when compared to MMR proficient tumours. In this study 40% of the patients with a MMR or MSI-H colorectal cancer had an immune related objective response, and the progression free survival rate at 20 weeks was 78% for the patients with a MMR colorectal cancer. If the benefits of pembrolizumab are confirmed, MMR functional testing of all colorectal cancers is likely to become mandatory.

It is also noted that the drug irinotecan shows promise as an MSI-H cancer drug. Data from preclinical studies suggest that it could be more effective for MSI-H colorectal cancers compared to MSS colorectal cancers. The drug bevacizumab may also be effective as a treatment for MSI-H colorectal cancers, but does not appear to give any survival benefit to patients with MSS tumours. There are also other drugs that appear to work well for MSS CRCs but don't work well for MSI-H CRCs. For example, evidence suggests that the drugs cisplatin and carboplatin do not work well on cancers with a compromised mismatch repair (MMR) system.

The drug 5-fluorouracil (5-FU) may also be useful for treating colorectal cancers exhibiting compromised mismatch repair (MMR) systems.

The advent of high throughput sequencing technologies has enabled the potential for sequence based MSI classification to be investigated at the genome level. The potential utility of a sequence based approach was established by a CGAP exome analysis of 224 CRCs and normal pairs which looked at mononucleotide repeats to establish that MSI could be detected using next generation sequencing. (Cancer Genome Atlas Network, 2012). A result later confirmed in gastric cancers and gastric cancer cell lines where mononucleotide repeats were analysed. Since then, software has been developed to analyse whole genome, exome, whole transcriptome, and capture panel data. Currently, such genome-wide approaches are not cost effective.

To cope with the increase in tumours being tested for microsatellite instability (MSI) in countries where this in not already being routinely done, it would be advantageous to consider high throughput screening approaches to test for MSI.

Variant Calling

A potential issue with an approach using high throughput or next generation sequencing is that for indels there is still very little consistency between different variant callers (Li, 2014, O'Rawe et al., 2013). O'Rawe et al. (2013) assessed three different variant calling pipelines (SOAPindel, BWA-GATK, SAMtools) and discovered that there was only a 26.8% concordance between the indels being called using those pipelines. 28.5% of the indels were unique to GATK, 22.4% unique to SOAPindel, and 7.8% unique to SAMtools (O'Rawe et al, 2013). Pabinger et al. (2014) compared the number of indel calls made by CRISP, GATK, SAMtools, SNVer and VarScan 2, and they called 259, 1959, 234, 332 and 1896 indels respectively, with GATK and Varscan having the largest number of indels in common (~57%). Houniet et al. (2015) have evaluated the indel callers Samtools, Dindel and GATK for their ability to identify indels in exome sequences. The results of their analysis showed that Samtools had a sensitivity of less than 0.05 for identifying indels while GATK had a sensitivity of around 0.35 and Dindel had a sensitivity ranging from ~0.17-~0.38 depending on which aligner was used.

There are many reasons why calling indels is a challenge. Sequence error is one problem, as the average error rate for Illumina sequences is 0.002% for 2 bp mononucleotide repeats, but rises to ~2% for 17 bp mononucleotide repeats (Minoche et al., 2011). There is also concern that PCR errors in mononucleotide repeats are still not being modelled well, with different variant callers calling different indels. Gapped alignment around indels represent a further challenge, particularly in low complexity regions, where incorrect alignment can create false indels. True indels may also be lost after being filtered out by low-complexity filters. Finally, most variant callers are geared towards bi-allelic genomes and can result in the removal of low frequency variants that do not meet set criteria for heterozygosity. Linked SNPs could potentially be used to differentiate between indels caused by artefacts and indel originating from MSI if MSI presents as a mono-allelic event. Such an approach has not before been tested.

It would be advantageous to provide an MSI test that could potentially be rolled out into a clinical setting as a high throughput MSI test.

It would be advantageous to provide a new system and/or method for variant calling to determine biological significance.

The present invention aims to mitigate one or more of the disadvantages associated with the prior art.

SUMMARY OF THE INVENTION

The inventors have shown that their next generation sequencing based MSI test is comparable with currently used methods for identifying loss of mismatch repair function.

According to the present invention there is provided a method for evaluating levels of microsatellite instability in a sample comprising:

(a) providing primers for amplifying a plurality of the selected group of microsatellite loci of human genomic DNA identified in Table A (b) amplifying from the sample the plurality of selected microsatellite mono-nucleotide repeat loci to give microsatellite amplicons;

(c) sequencing the microsatellite amplicons; and (d) comparing the sequences from the microsatellite amplicons to predetermined sequences and determining any deviation, indicative of instability, from the predetermined sequences.

Deviation may be in the form of an insertion or deletion when compared to the predetermined sequences.

Optionally, in step (a) primers are provided for amplifying at least 6 or at least 7 of the selected group of microsatellite loci identified in Table A, optionally wherein the at least 6 or at least 7 microsatellite loci are selected group consisting of GM07, LR11, LR36, LR44, LR48, IM49 and GM14.

Optionally, in step (a) primers are also provided for amplifying the microsatellite loci DEPDC2 and AP003532_2.

Optionally in step (a) primers are provided for amplifying at least 10 of the selected group of microsatellite loci of human genomic DNA of Table A and/or Table B or at least 17 of the selected group of microsatellite loci of human genomic DNA of Table A and/or Table B or at least 18 of the selected group of microsatellite loci of human genomic DNA of Table A and/or Table B.

More preferably step (a) is providing primers for amplifying at least 10 of the selected group of microsatellite loci of human genomic DNA comprising;
DEPDC2, LR46, AL359238, AL954650, AP003532_2, TTK, AL355154, AVIL, GM29, LR32, ASTE1, GM07, GM14, LR11, LR48, IM49, LR36, LR44, LR49, IM66, LR20, GM11, LR24, IM16, GM17, GM9.

More preferably step (a) is providing primers for amplifying at least 10 of the selected group of microsatellite loci of human genomic DNA comprising;
DEPDC2, LR46, AL359238, AL954650, AP003532_2, TTK, AL355154, AVIL, GM29, LR32, ASTE1, GM07, GM14, LR11, LR48, IM49, LR36, LR44.

Optionally step (a) is providing primers for amplifying the selected group of microsatellite loci of human genomic DNA comprising;
DEPDC2, LR46, AL359238, AL954650, AP003532_2, TTK, AL355154, AVIL, GM29, LR32, ASTE1, GM07, GM14, LR11, LR48, IM49, LR36, LR44.

More preferably step (a) is providing primers for amplifying at least 10 of the selected group of microsatellite loci of human genomic DNA comprising;
LR49, IM66, LR20, GM11, LR24, IM16, GM17, GM9, GM07, LR36, LR44, LR48, LR11, AP003532_2, DEPDC2, GM14, IM49.

Optionally step (a) is providing primers for amplifying the selected group of microsatellite loci of human genomic DNA comprising;
LR49, IM66, LR20, GM11, LR24, IM16, GM17, GM9, GM07, LR36, LR44, LR48, LR11, AP003532_2, DEPDC2, GM14, IM49.

The loci referred to above are further specified in Table A.

Preferably the primers are for co-amplifying the selected microsatellite loci.

Preferably the step of (b) amplifying from the sample the plurality of selected microsatellite mono-nucleotide repeat loci to give microsatellite amplicons, comprises co-amplifying the set of selected loci in a multiplex amplification reaction.

Optionally the primer pairs are selected to allow for multiplexing.

Alternatively a number of separate microsatellite mono-nucleotide repeat loci are amplified and sequenced as separate reactions.

Preferably the step of (c) uses high throughput or next generation sequencing.

Optionally step (c) uses sequencing-by-synthesis.

Optionally step (c) uses ion semiconductor sequencing or ion torrent sequencing.

Optionally step (c) uses pyrosequencing.

Preferably amplification is by polymerase chain reaction and uses using primer pairs, each primer pair comprising a forward primer which is complimentary to a portion upstream from a selected microsatellite mono-nucleotide repeat loci, and a reverse primer which is complimentary to a portion downstream from said selected microsatellite mono-nucleotide repeat loci.

Preferably the selected group of microsatellite loci also include a single nucleotide polymorphism (SNP) within a short distance of the microsatellite loci.

Optionally the selected group of microsatellite loci also include a single nucleotide polymorphism (SNP) within 100 base pairs of the microsatellite loci.

Optionally the selected group of microsatellite loci also include a single nucleotide polymorphism (SNP) within 80 base pairs of the microsatellite loci.

Optionally the selected group of microsatellite loci also include a single nucleotide polymorphism (SNP) within 50 base pairs of the microsatellite loci.

Optionally the selected group of microsatellite loci also include a single nucleotide polymorphism (SNP) within 30 base pairs of the microsatellite loci.

Preferably the single nucleotide polymorphism (SNP) has a minor allele frequency between 0.05-0.95.

Preferably the single nucleotide polymorphism (SNP) has a high frequency.

Preferably the primers are selected to amplify both the microsatellite loci and the SNP.

The amplification step (b) gives microsatellite amplicons including both microsatellite and SNP.

The method can include the step of determining allelic imbalance.

The method can include the step of diagnosing MSI induced CRC or Lynch syndrome. This may further include the step of proposing an appropriate class of therapeutics or specific therapeutics e.g. pembromizulab.

A method as above may be useful for identifying mismatch repair defects, wherein deviation from the predetermined sequences for two or more microsatellite mono-nucleotide repeat loci is indicative of a mismatch repair defect.

A method as above may be useful for identifying MSI-H, wherein deviation from the predetermined sequences for two or more microsatellite mono-nucleotide repeat loci is indicative of the sample having high levels of microsatellite instability (MSI-H).

Optionally the sample is a tumor sample or a body tissue or fluid suitable for detecting tumor cells.

Preferably the sample is a human tissue or fluid sample.

Optionally the sample may be a nucleic acid sample.

According to another aspect of the present invention there is provided a kit for evaluating levels of microsatellite instability in a sample, comprising: oligonucleotide primers for co-amplifying a plurality of microsatellite loci of human genomic DNA selected from the set of microsatellite loci identified in Table A.

Optionally, the primers are for amplifying at least 6 or at least 7 of the selected group of microsatellite loci identified in Table A, optionally wherein the at least 6 or at least 7 microsatellite loci are selected group consisting of GM07, LR11, LR36, LR44, LR48, IM49 and GM14.

Optionally, the kit further comprising primers that are for amplifying the microsatellite loci DEPDC2 and AP003532_2.

Optionally the primers are for amplifying at least 10 of the selected group of microsatellite loci of human genomic DNA of Table A and/or Table B or at least 17 of the selected group of microsatellite loci of human genomic DNA of Table A and/or Table B or at least 18 of the selected group of microsatellite loci of human genomic DNA of Table A and/or Table B.

More preferably the primers are for amplifying at least 10 of the selected group of microsatellite loci of human genomic DNA comprising;

DEPDC2, LR46, AL359238, AL954650, AP003532_2, TTK, AL355154, AVIL, GM29, LR32, ASTE1, GM07, GM14, LR11, LR48, IM49, LR36, LR44, LR49, IM66, LR20, GM11, LR24, IM16, GM17, GM9.

More preferably the primers are for amplifying at least 10 of the selected group of microsatellite loci of human genomic DNA comprising;

DEPDC2, LR46, AL359238, AL954650, AP003532_2, TTK, AL355154, AVIL, GM29, LR32, ASTE1, GM07, GM14, LR11, LR48, IM49, LR36, LR44.

Optionally the primers are for amplifying the selected group of microsatellite loci of human genomic DNA comprising;

DEPDC2, LR46, AL359238, AL954650, AP003532_2, TTK, AL355154, AVIL, GM29, LR32, ASTE1, GM07, GM14, LR11, LR48, IM49, LR36, LR44.

More preferably the primers are for amplifying at least 10 of the selected group of microsatellite loci of human genomic DNA comprising;

LR49, IM66, LR20, GM11, LR24, IM16, GM17, GM9, GM07, LR36, LR44, LR48, LR11, AP003532_2, DEPDC2, GM14, IM49.

Optionally the primers are for amplifying the selected group of microsatellite loci of human genomic DNA comprising;

LR49, IM66, LR20, GM11, LR24, IM16, GM17, GM9, GM07, LR36, LR44, LR48, LR11, AP003532_2, DEPDC2, GM14, IM49.

Typically the primers are selected according to the above lists from those primers identified in Table B.

Preferably the kit also comprises a thermostable polymerase.

Optionally the kit also comprises labeled dNTPs or analogs thereof.

Optionally the labeled dNTPs or analogs thereof are fluorescently labeled.

According to another aspect of the present invention there is provided a method for evaluating the biological significance of mutations identified during sequencing:

(a) providing primers for amplifying a plurality of a selected group of microsatellite mono-nucleotide repeat loci of human genomic DNA, said microsatellite loci having a single nucleotide polymorphisms loci within a short distance of the microsatellite loci and said primers selected to amplify both the microsatellite loci and the SNP in a single amplicon;

(b) amplifying from the sample the plurality of selected microsatellite mono-nucleotide repeat loci to give microsatellite amplicons;

(c) sequencing the microsatellite amplicons; and (d) comparing the sequences from the microsatellite amplicons to predetermined sequences (wild type sequences) and determining any deviation, indicative of instability, from the predetermined sequences; and (e) for heterozygous SNPs, determining whether there is a bias between indel frequencies for the two alleles.

Optionally the selected group of microsatellite loci include a single nucleotide polymorphism (SNP) within 100 base pairs of the microsatellite loci.

Optionally the selected group of microsatellite loci include a single nucleotide polymorphism (SNP) within 80 base pairs of the microsatellite loci.

Optionally the selected group of microsatellite loci include a single nucleotide polymorphism (SNP) within 50 base pairs of the microsatellite loci.

Optionally the selected group of microsatellite loci include a single nucleotide polymorphism (SNP) within 30 base pairs of the microsatellite loci.

Preferably the single nucleotide polymorphism (SNP) has a minor allele frequency between 0.05-0.95.

Preferably the single nucleotide polymorphism (SNP) has a high frequency.

Throughout the description and claims of this specification, the words "comprise" and "contain" and variations of them mean "including but not limited to", and they are not intended to (and do not) exclude other moieties, additives, components, integers or steps.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $2^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. As a further example, Singleton and Sainsbury, Dictionary of Microbiology and Molecular Biology, 2d Ed., John Wiley and Sons, NY (1994); and Hale and Marham, The Harper Collins Dictionary of Biology, Harper Perennial, NY (1991) provide those of skill in the art with a general dictionary of many of the terms used in the invention. Although any methods and materials similar or equivalent to those described herein find use in the practice of the present invention, the preferred methods and materials are described herein.

Throughout the description and claims of this specification, the singular encompasses the plural unless the context otherwise requires. In particular, where the indefinite article is used, the specification is to be understood as contemplating plurality as well as singularity, unless the context requires otherwise. Accordingly, as used herein, the singular terms "a", "an," and "the" include the plural reference unless the context clearly indicates otherwise.

Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

Features, integers, characteristics, compounds, chemical moieties or groups described in conjunction with a particular aspect, embodiment or example of the invention are to be understood to be applicable to any other aspect, embodiment or example described herein unless incompatible therewith.

The patent, scientific and technical literature referred to herein establish knowledge that was available to those skilled in the art at the time of filing. The entire disclosures of the issued patents, published and pending patent applications, and other publications that are cited herein are hereby incorporated by reference to the same extent as if each was specifically and individually indicated to be incorporated by reference. In the case of any inconsistencies, the present disclosure will prevail.

Various aspects of the invention are described in further detail below.

BRIEF DESCRIPTION OF THE DRAWINGS

In order to provide a better understanding of the present invention, embodiments will be described by way of example only and with reference to the following figures in which.

DETAILED DESCRIPTION

Figure 1:
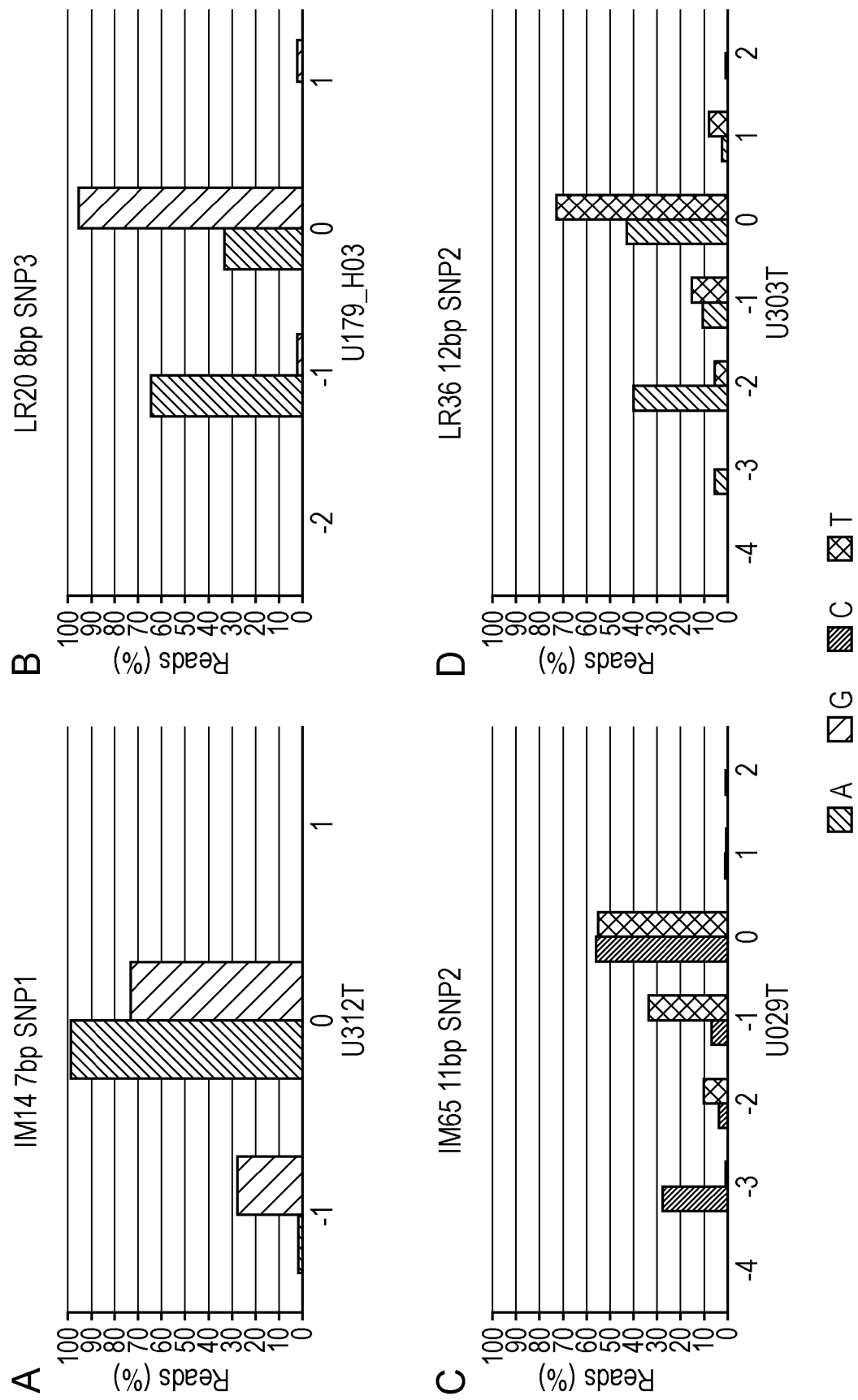
FIG. 1 shows examples of allelic imbalance in different lengths of mononucleotide repeat. Panel A the repeat IM14 in tumour U312, Panel B the repeat LR20 in tumour U179_H03, Panel C the repeat IM65 in tumour U029, Panel D the repeat LR36 in tumour U303.

Testing for microsatellite instability is one of the main methods used to assess MMR proficiency. However, somatic microsatellite mutations can also be observed in MMR proficient tumours. Thus, detection of low levels of microsatellites instability is not considered to be indicative of mismatch repair defects (de la Chapelle and Hampel, 2010 and Laiho et al., 2002). Microsatellite instability is commonly tested by amplification of a panel of microsatellites followed by analysis of the amplified fragments by capillary electrophoresis. A variety of panels have been recommended and current tests rely on long MNRs (e.g. Boyle et al., 2014). Long homopolymers tend to be more unstable both in vivo and in vitro, and PCR-induced errors lead to stutter peaks in electropherograms (Shinde et al., 2003). This can complicate downstream phenotype interpretation and visual inspection of the fragment size profiles can be required.

Samples can be classified according to the frequency of microsatellite mutations. For example, the Revised Bethesda Guidelines for Hereditary Nonpolyposis Colorectal Cancer (Lynch Syndrome) and Microsatellite Instability described a classification using a panel of 5 quasi monomorphic MNR (Umar et al., 2004). Samples showing mutations in two or more MMR designated as microsatellite instability high (MSI-H) samples, samples with only one altered MNR as MSI-L (microsatellite instability low) and where all microsatellites appear to be stable as MSS (microsatellite stable). MSI-H status is indicative of an MMR defect.

Microsatellite instability assesses the function of the MMR system. An alternative is to ascertain the presence of its components by immunohistochemistry (IHC). Lack of protein can result from mutations causing premature truncation of the encoded polypeptides and nonsense-mediated decay, or from the destabilisation of protein complexes leading to accelerated degradation of their components(Shia, 2008). Immunohistochemistry requires highly skilled personnel. Since IHC assesses MMR the levels of MMR proteins as opposed to a consequence of MMR dysfunction, there is some discordance between the results of microsatellite instability and IHC analyses (Shia 2008 and Zhang 2008). The reported concordance varies but a sensitivity of IHC in predicting MSI of 92% has been reported (Shia, 2008).

In the past few years, several groups have developed sequencing based approaches to identify microsatellite instability. These include methods utilising genome (Niu et al., 2014) or transcriptome (Lu et al., 2013) wide data as well as sequences from target enriched libraries (Salipante et al., 2014). In vitro amplification errors, which lead to the presence of variant read lengths in the PCR product, can complicate sequence-based approaches. The frequency of such artefacts will differ between MNRs, but some mutant reads are expected even in the absence of mutations in the starting material. One approach to address the problem of amplification errors is to use a threshold value of the proportion of mutant molecules to discriminate between PCR-artefacts and the genuine presence of MNR mutations in the starting material (e.g. Salipante et al., 2014).

Short MNRs tend to be less polymorphic than longer ones (Ananda et al., 2013). Thus, the likelihood of encountering germline variants in short MNRs is reduced, suggesting that they would be suitable for assessing MSI status in tumours without requiring matched germline DNA. The lower mutation rate also means that mutant reads from shorter repeats are more likely to reflect a single mutational event, and affect only one allele while recurrent artefacts will affect both alleles. As a result, assessing whether length variants are concentrated in one allele offers an additional criterion to differentiate between PCR artefacts and mutations that occur in vivo.

The inventors have developed a method suitable for high throughput and automated MSI analysis that allows separation of samples into two classes: MSI and MSS. The former corresponds to samples classified as MSI-H by fragment analysis while with the latter includes MSS samples and samples with low levels of instability (MSI-L).

The inventors have selected a panel of short MNR, and have developed a method to score instability based on both MNR specific variant read frequency thresholds and allelic bias. The parameters required for classification were determined in a series of 139 tumours where the MSI status had been previously characterised, and an independent cohort of 70 tumours was used for blinded validation of the method.

The inventors have therefore developed a novel approach to the detection of MSI tumours whose main advantage is its simplicity making it suitable for high throughput analysis without the need for control normal DNA. Establishing whether tumours have resulted from a breakdown in mismatch repair is important in clinical management of the individual and can help prevent future cancers in those families where there is a germline molecular defect. Expansion of testing to all colorectal cancers has been shown to be cost effective in the UK (Snowsill et al., 2014) and is soon to become standard of care on the basis of National Institute of Healthcare and Clinical Excellence (NICE) guidance in the UK National Health Service(NICE, 2017, Molecular testing strategies for Lynch syndrome in people with colorectal cancer). Similar decisions are being taken in other developed nations. A scalable, reliable MSI test will have clinical utility while modest costs and the ability to link this analysis to routine pathology assessment with help to ensure rapid adoption and facilitate further molecular approaches to tumour profiling and precision medical care.

Definitions

The term "microsatellite" or "microsatellite regions" as used herein refers to mono-, di-, tri-, tetra, penta- or hexa-nucleotide repeats in a nucleotide sequence, consisting of at least two repeat units and with a minimal length of 6 bases. A particular subclass of microsatellites includes the homopolymers. "Homopolymer" as used herein refers to a microsatellite region that is a mononucleotide repeat of at least 6 bases; in other words a stretch of at least 6 consecutive A, C, T or G residues if looking at the DNA level. Most particularly, when determining microsatellites, one looks at genomic DNA of a subject (or of genomic DNA of a cancer present in the subject).

The term "MSI status" as used in the application refers to the presence of microsatellite instability (MSI), a clonal or somatic change in the number of repeated DNA nucleotide units in microsatellites. MSI status can be one of three discrete classes: MSI-H, also referred to as MSI-high, MSI positive or MSI, MSI-L, also referred to as MSI-low, or microsatellite stable (MSS), also referred to as absence of MSI. Typically, to be classified as MSI-H, at least 20% of the markers used to classify MSI status need to score positive, while for the MSS classification, less than 2.5% score positive. If an intermediate number of markers scores positive, the tumor is classified as MSI-L. Alternatively, only the difference between presence and absence of microsatellite instability is assessed, in which case the status is either presence of MSI or absence of MSI (=MSS).

An "indel" as used herein refers to a mutation class that includes both insertions, deletions, and the combination thereof. An indel in a microsatellite region results in a net gain or loss of nucleotides. The presence of an indel can be established by comparing it to DNA in which the indel is not present (e.g. comparing DNA from a tumor sample to germline DNA from the subject with the tumor), or, especially in case of monomorphic microsatellites or homopolymers, by comparing it to the known length of the microsatellite, particularly by counting the number of repeated units.

The term "cancer" as used herein, refers to different diseases involving unregulated cell growth, also referred to as malignant neoplasm. The term "tumor" is used as a synonym in the application. It is envisaged that this term covers all solid tumor types (carcinoma, sarcoma, blastoma), but it also explicitly encompasses non-solid cancer types such as leukemia. Thus, a "sample of tumor DNA" can also be a blood sample from a person with leukemia. Typically, a sample of tumor DNA has at one point been isolated from a subject, particularly a subject with cancer. Optionally, it has undergone one or more forms of pre-treatment (e.g. lysis, fractionation, separation, purification) in order for the DNA to be sequenced, although it is also envisaged that DNA from an untreated sample is sequenced. As used herein, the noun "subject" refers to an individual vertebrate, more particularly an individual mammal, most particularly an individual human being.

A "subject" as used herein is typically a human, but can also be a mammal, particularly domestic animals such as cats, dogs, rabbits, guinea pigs, ferrets, rats, mice, and the like, or farm animals like horses, cows, pigs, goat, sheep, llamas, and the like. A subject can also be a non-mammalian vertebrate, like a fish, reptile, amphibian or bird; in essence any animal which can develop cancer fulfills the definition.

The term "Lynch syndrome" as used herein refers to an autosomal dominant genetic condition which has a high risk of colon cancer as well as other cancers including endometrium, ovary, stomach, small intestine, hepatobiliary tract, upper urinary tract, brain, and skin cancer. The increased risk for these cancers is due to inherited mutations that impair DNA mismatch repair. The old name for the condition is HNPCC.

As will be described in detail below in the Examples section, the invention provides a plurality of markers that can be used to differentiate between MSI-H and MSS tumours (e.g. MSI-H CRCs, such as Lynch Syndrome). Specific panels of 18 and 17 markers are provided in Examples 1 and 2. However, any combination of the informative markers within these panels may also be used. The methods and kits of the invention may therefore utilise two or more markers (as identified in Table A and/or Table B), and may particularly utilise two or more (i.e. 2, 3, 5, 5, 7, 8, 9, 10, 11, 12, 13, 14, 15, 16, 17, 18, 19, 20, 21, 22, 23, 24, 25 or 26) markers that are present within the validated 18-repeat panel of Example 1 and/or the validated 17-repeat panel of Example 2.

The 18-marker panel of Example 1 and the 17-marker panel of Example 2 have nine markers in common, notably, DEPDC2, AP003532_2, GM7, GM14, LR11, LR36, LR44, LR48 and IM49. This particular combination of markers has been found to be informative in distinguishing MSI-H and MSS tumours in respect of either panel. This particular combination of markers may therefore specifically be used within the context of the invention (or a similar combination, wherein at least one of these markers, e.g. GM14, is omitted). Other markers may also be added.

It is particularly noted that seven of these markers, i.e. GM7, GM14, LR11, LR36, LR44, LR48 and IM49 are newly identified markers for testing MSI status. Any panel that utilises one or more, e.g. two or more, three or more, four or more, five or more, six or more, or all seven of these markers therefore is encompassed by the invention. This particular combination of markers may therefore specifically be used within the context of the invention (or a similar combination, wherein at least one of these markers, e.g. GM14, is omitted). Other markers may also be added.

It is also noted that Example 2 identified an additional 8 small (7-9 bp) markers that were particularly informative i.e. GM9, GM11, GM17, LR20, LR24, LR49, IM16 and IM66. Each of these markers are is a newly identified marker for testing MSI status. Any panel that utilises one or more, e.g. two or more, three or more, four or more, five or more, six or more, seven or more, or all eight of these markers therefore is encompassed by the invention (e.g. use of a combination of GM09, GM11, LR49, IM16, LR20 and LR24, optionally together with other markers, is specifically encompassed). This particular combination of markers is may therefore specifically be used within the context of the invention (or a similar combination, wherein at least one of these markers is omitted). Other markers may also be added.

In accordance with the above, the newly identified markers for determining MSI status that have been validated using the panels of Examples 1 and 2 include GM7, GM14, LR11, LR36, LR44, LR48, IM49, GM9, GM11, GM17, LR20, LR24, LR49, IM16 and IM66. The use of any of these markers for determining MSI status (and/or diagnosing or facilitating diagnosis of MSI-H CRSCS, such as Lynch syndrome; and/or determining the presence of a mismatch repair defect) is therefore encompassed by the invention, whether the markers is used in isolation, or in combination with other known markers, or in combination with one or more of the new markers identified herein.

As used herein, the terms "microsatellite loci", or "repeat" and "marker" are used interchangeably where the context allows.

As used herein, the terms "GM07" and "GM7" are used interchangeably herein. Similarly, the terms "AP003532_2" and "AP0035322" are also interchangeable.

Aspects of the invention are demonstrated by the following non-limiting examples.

EXAMPLES

The examples describe how genome wide analysis of instability in CRC tumours was used to identify unstable short microsatellites. Particular focus was given to identifying repeats linked to high frequency SNPs to facilitate deconvolution of sequence error and instability. One hundred and twenty 7-12 bp markers were identified. The inventors then assessed the panel of one hundred and twenty 7-12 bp markers defined by this screen for sequence based typing. The initial 120 of the identified mononucleotide repeats were analysed on a small panel of tumours in two studies to confirm that these repeats could be used as markers for identifying MSI. The first study identified a panel of 18 repeats that were particularly informative (Example 1). The second study focused on repeats of short length (7-9 bp) and identified 8 additional markers that were particularly informative. These 8 markers were combined with the most informative 9 markers of example 1 to generate a new 17 marker panel (Example 2). A larger panel of colorectal tumours were then analysed using some of the most informative repeats and it was shown that the two panels of 18 and 17 repeats respectively are highly susceptible to deletions in MSI-H tumours, and could be used to differentiate between MSI-H and MSS tumours.

The invention therefore provides a plurality of markers that can be used to differentiate between MSI-H and MSS tumours. Specific panels of 18 and 17 markers are provided. However, any combination of the particularly informative markers within these panels may also be used. The methods and kits of the invention may therefore ultilise two or more markers (as identified in Table A and/or Table B), and may particularly utilise two or more markers that are present within the validated 18-repeat panel of Example 1 and/or the validated 17-repeat panel of Example 2.

Examples 1 to 3 describe ways in which the method of the invention may be implemented using an assay that requires individual PCR amplification of each repeat for every sample and subsequent pooling for sequencing.

Example 4 provides details of how the method of the invention may be implemented using a multiplexed sequencing based assay using single molecule-molecular inversion probe (smMIP) technology. As is well known, multiplexing reduces the overall cost and complexity of such methods. smMIPs allow for simultaneous targeting, capture and PCR amplification of all the markers of interest in the DNA sample. This negates the need of pooling amplified DNA sequences of every marker for each sample and hence: streamlines laboratory workflow, reduces cost, requires less quantity of input DNA sample, reduces risk of sample mixup and reduces turnaround time of the assay. The inventors have designed and tested smMIPs for a large panel of markers of interest as outlined in Example 4 below.

Example 1

Selection of a Panel of Mononucleotide Repeats Prioritising Short Repeats

To investigate the stability or variability of short mononucleotide repeats in tumours with mismatch repair (MMR) defects at the genome level, whole genome sequence data from MSI-H colorectal cancers was mined to identify new homopolymers that are highly variable in MSI-H tumours.

A total of 218,181 variable 7-12 bp homopolymers were identified from the whole genome analysis. 216495 A/T mononucleotide repeats with indels (insertions or deletions) were identified, but only 1686 C/G mononucleotide repeats. Finding more unstable A/T mononucleotide repeats than G/C mononucleotide repeats is consistent with data reported in cell lines by Yoon et al. (2013). To validate specific repeats for MSI detection, some of the most unstable homopolymers identified in the whole genome analysis were selected for further analysis. The list of 218,181 variable 7-12 bp homopolymers was narrowed down by filtering for repeats with a read depth ≥20× in each group (MSI-H, matched normal for the MSI-H samples, and MSS samples). Repeats with common polymorphisms (dbSNP version 173, hg19) were excluded. 7-10 bp repeats were selected if they had a variant read fraction of 10% or higher in the MSI high sample group and no variant reads in the controls. For the 11-12 bp repeats were selected if they had an alternate allele fraction of 15% or higher in the MSI-H samples and a variant read fraction of ≤5% in the controls. A variant read fraction of ≤5% in 11-12 bp repeats was presumed to be caused by sequencing and PCR error. Homopolymers with low indel frequencies in the control samples were desired because it would be easier to cope with repeats with a low background error rate. It is presumed that variation in background errors could to some extent be attributed to sequence context.

Homopolymers were selected to ensure the inclusion of SNPs with a high minor allele frequency within 30 bp were selected. The Perl script AnnotateCloseSNPs.pl was used to annotate SNPs within 30 bp of the start of repeats. If there were more than one SNP detected within 30 bp of a repeat, the minor allele frequencies were added together as a quick method to assess the value of the SNPs. Repeats were only selected if there were SNPs within 30 bp of the repeat with minor allele frequencies, which summed up to least a frequency of 0.2. In total 529 A/T homopolymers fitted these criteria. Because of there were few G/C homopolymers in the data set the criteria for including SNPs within 30 bp of the repeat was omitted and the requirement for a read depth ≤20× in each group was relaxed. This resulted in a data set of 33 G/C homopolymers.

The UCSC Genome browser (Kent et al., 2002) was used to assess the possibility of creating primers for the homopolymers that passed the above criteria. Many of the 529 A/T homopolymers and 33 G/C homopolymers that met the selection criteria above were situated in regions of low complexity such as LINES and SINES, which limited the number of repeats where primers could be produced without the risk of miss priming. The 120 most variable repeats for which suitable primers could be produced were selected to assess the utility of these specific mononucleotides for sequence based detection of MSI repeat length variation. These are shown in Table A below.

TABLE A

A list of the 120 mononucleotide repeats sequenced. This list contains the designated repeat names, the length and location of each mononucleotide repeat, and the rs numbers of neighbouring SNPs.

| Repeat Name | Repeat Size | Repeat Position | SNP1 | SNP2 | SNP3 |
| --- | --- | --- | --- | --- | --- |
| GM04 | 7 bp | chr13:92677561 | rs9560900 | | |
| GM19 | 7 bp | chr11:114704378 | rs142833335 | rs190597109 | rs10502196 |
| GM24 | 7 bp | chr10:117432196 | rs2532728 | | |
| GM25 | 7 bp | chr3:110871917 | rs74593281 | rs6437953 | rs188039266 |
| GM27 | 7 bp | chr11:85762247 | rs669813 | rs181565251 | rs146406522 |
| GM30 | 7 bp | chr14:53111542 | rs12880534 | | |
| IM13 | 7 bp | chr2:235497098 | rs6721256 | rs183025093 | rs187312036 |
| IM14 | 7 bp | chr7:80104530 | rs11760281 | | |
| IM19 | 7 bp | chr9:82475000 | rs72736428 | rs186539440 | rs4877153 |
| IM20 | 7 bp | chr13:57644695 | rs6561918 | | |
| IM22 | 7 bp | chr7:90135495 | rs10487118 | rs10487117 | rs139214151 |
| IM23 | 7 bp | chr6:72729530 | rs557365 | | |
| IM26 | 7 bp | chr3:166053586 | rs2863375 | | |
| IM27 | 7 bp | chr7:35079238 | rs4723393 | rs112516918 | |
| IM43 | 7 bp | chr21:32873760 | rs9981507 | | |
| IM55 | 7 bp | chr3:143253844 | rs13099818 | | |
| IM61 | 7 bp | chr12:73576422 | rs34696106 | | |
| IM66 | 7 bp | chr17:48433966 | rs147847688 | rs141474571 | rs4794136 |
| IM67 | 7 bp | chr7:22290894 | rs67082587 | rs57484333 | |
| IM69 | 7 bp | chr9:92765722 | rs1036699 | | |
| LR04 | 7 bp | chr1:4677109 | rs113646106 | rs2411887 | |
| LR06 | 7 bp | chr18:20089449 | rs501714 | | |
| LR08 | 7 bp | chr11:56546205 | rs181578273 | rs7117269 | |
| LR13 | 7 bp | chr8:21786971 | rs2127206 | | |
| LR15 | 7 bp | chr8:92077209 | rs56084507 | | |
| LR25 | 7 bp | chr16:63209545 | rs76192782 | rs79880398 | rs4949112 |
| LR45 | 7 bp | chr2:226938121 | rs180896305 | rs1522818 | rs144175764 |
| LR47 | 7 bp | chr10:20506728 | rs11597326 | rs12256106 | |
| LR49 | 7 bp | chr15:93619047 | rs80323298 | rs201097746 | rs12903384 |
| LR50 | 7 bp | chr2:76556320 | rs925991 | rs144630203 | |
| LR51 | 7 bp | chr10:51026724 | rs8474 | | |

TABLE A-continued

A list of the 120 mononucleotide repeats sequenced. This list contains
the designated repeat names, the length and location of each mononucleotide
repeat, and the rs numbers of neighbouring SNPs.

| Repeat Name | Repeat Size | Repeat Position | SNP1 | SNP2 | SNP3 |
| --- | --- | --- | --- | --- | --- |
| GM03 | 8 bp | chr4:120206446 | rs17050454 | rs10032299 | |
| GM08 | 8 bp | chr21:36575085 | rs2834837 | rs115025058 | |
| GM09 | 8 bp | chr20:6836976 | rs6038623 | | |
| GM16 | 8 bp | chr6:100743595 | rs7765823 | | |
| GM20 | 8 bp | chr7:142597494 | rs6961869 | rs6961877 | |
| IM15 | 8 bp | chr6:91455181 | rs1231482 | | |
| IM21 | 8 bp | chr1:215136389 | rs181787229 | rs1901621 | rs1901620 |
| IM25 | 8 bp | chr12:24568356 | rs10771087 | | |
| IM39 | 8 bp | chr2:103233866 | rs76771828 | rs190979688 | rs187315716 |
| IM40 | 8 bp | chr4:84074813 | rs10516683 | | |
| IM41 | 8 bp | chr6:147948940 | rs1944640 | rs112075239 | |
| IM57 | 8 bp | chr3:81210016 | rs35085583 | | |
| IM59 | 8 bp | chr8:108359000 | rs10156232 | | |
| IM63 | 8 bp | chr3:115816065 | rs34764455 | | |
| IM68 | 8 bp | chr12:129289692 | rs10847692 | | |
| LR02 | 8 bp | chr4:134947775 | rs189671825 | rs192703656 | rs1494978 |
| LR18 | 8 bp | chr1:220493934 | rs191265856 | rs199830128 | rs74940412 |
| LR19 | 8 bp | chr12:29508668 | rs10843391 | rs186762840 | |
| LR20 | 8 bp | chr1:64029633 | rs146973215 | rs191572633 | rs217474 |
| LR27 | 8 bp | chr4:72877514 | rs55894427 | rs74733006 | |
| LR31 | 8 bp | chr3:62995577 | rs183248146 | rs2367592 | |
| LR46 | 8 bp | chr20:10660084 | rs143884078 | rs182346625 | rs6040079 |
| GM05 | 9 bp | chr2:216770762 | rs6704859 | | |
| GM06 | 9 bp | chr16:77496517 | rs6564444 | rs143453795 | rs145573459 |
| GM10 | 9 bp | chr1:59891623 | rs946576 | rs182557762 | |
| GM11 | 9 bp | chr5:166099890 | rs347435 | | |
| GM15 | 9 bp | chr7:97963736 | rs6465672 | | |
| GM17 | 9 bp | chr11:95551110 | rs666398 | | |
| GM21 | 9 bp | chr3:142695338 | rs185182 | | |
| GM23 | 9 bp | chr5:11345920 | rs184237728 | rs32123 | |
| GM28 | 9 bp | chr5:29209380 | rs4130799 | | |
| IM16 | 9 bp | chr18:1108766 | rs114923415 | rs73367791 | rs59912715 |
| IM17 | 9 bp | chr13:31831504 | rs932749 | | |
| IM42 | 9 bp | chrX:96502620 | rs1409192 | | |
| IM44 | 9 bp | chr12:9797065 | rs201750704 | rs4763716 | |
| LR05 | 9 bp | chr2:10526616 | rs111286197 | rs13431202 | |
| LR10 | 9 bp | chr1:81591387 | rs111814302 | rs1768398 | rs1768397 |
| LR14 | 9 bp | chr17:69328494 | rs9895642 | | |
| LR21 | 9 bp | chr15:50189464 | rs182900605 | rs80237898 | rs2413976 |
| LR24 | 9 bp | chr1:153779428 | rs192329538 | rs1127091 | |
| LR28 | 9 bp | chr12:81229785 | rs185642078 | rs28576612 | rs10862196 |
| LR34 | 9 bp | chr3:115377097 | rs187521190 | rs192106258 | rs9883515 |
| LR40 | 9 bp | chr2:13447469 | rs6432372 | | |
| GM01 | 10 bp | chr11:28894428 | rs7951012 | | |
| GM22 | 10 bp | chr14:43401009 | rs58274313 | | |
| GM26 | 10 bp | chr14:49584750 | rs187027795 | rs11628435 | |
| GM29 | 10 bp | chr3:70905559 | rs2687195 | | |
| IM07 | 10 bp | chr6:100701947 | rs189035042 | rs6915780 | |
| IM12 | 10 bp | chr8:23602937 | rs389212 | | |
| IM33 | 10 bp | chr8:25731926 | rs202225742 | rs35644463 | rs113180202 |
| IM34 | 10 bp | chr7:83714718 | rs1524881 | | |
| IM35 | 10 bp | chr11:84425221 | rs67283158 | rs10792775 | rs116387070 |
| IM37 | 10 bp | chr17:50813569 | rs2331498 | | |
| LR26 | 10 bp | chr16:80050257 | rs4889066 | rs187883346 | |
| LR29 | 10 bp | chr6:78198348 | rs1778257 | | |
| LR30 | 10 bp | chr11:105445091 | rs7933640 | | |
| LR32 | 10 bp | chr19:37967219 | rs7253091 | | |
| LR35 | 10 bp | chr8:130384501 | rs4733547 | | |
| LR39 | 10 bp | chr17:66449341 | rs2302784 | | |
| GM02 | 11 bp | chr1:116246109 | rs10802173 | rs148789685 | |
| GM07 | 11 bp | chr7:93085747 | rs2283006 | | |
| GM13 | 11 bp | chr12:107492626 | rs34040859 | rs77265275 | rs201488736 |
| GM14 | 11 bp | chr3:177328817 | rs6804861 | | |
| IM28 | 11 bp | chr9:5122910 | rs10815163 | | |
| IM32 | 11 bp | chr18:42045500 | rs8087346 | | |
| IM45 | 11 bp | chr4:99545419 | rs189419054 | rs2178216 | |
| IM52 | 11 bp | chr21:22846823 | rs74462385 | rs9982933 | rs2155801 |
| IM53 | 11 bp | chr9:20662629 | rs182630429 | rs140426089 | rs12352933 |
| IM54 | 11 bp | chr21:33710014 | rs13046776 | | |
| IM65 | 11 bp | chr13:25000863 | rs7324645 | rs9511253 | |
| LR01 | 11 bp | chr13:97387479 | rs1924584 | rs4771258 | |
| LR11 | 11 bp | chr2:217217870 | rs13011054 | rs147392736 | rs139675841 |
| LR12 | 11 bp | chr14:47404235 | rs187434561 | rs144159314 | |
| LR16 | 11 bp | chr3:8522416 | rs148171413 | rs6770049 | |

TABLE A-continued

A list of the 120 mononucleotide repeats sequenced. This list contains the designated repeat names, the length and location of each mononucleotide repeat, and the rs numbers of neighbouring SNPs.

| Repeat Name | Repeat Size | Repeat Position | SNP1 | SNP2 | SNP3 |
| --- | --- | --- | --- | --- | --- |
| LR17 | 11 bp | chr14:55603030 | rs79618905 | rs77482253 | rs1009977 |
| LR23 | 11 bp | chr2:142013941 | rs434276 | rs146141768 | |
| LR33 | 11 bp | chr4:138498649 | rs200714826 | rs4637454 | rs111688169 |
| LR48 | 11 bp | chr12:77988096 | rs11105832 | | |
| GM18 | 12 bp | chr10:8269565 | rs113251670 | rs189036006 | rs533236 |
| IM47 | 12 bp | chr21:22734436 | rs2588655 | rs149325240 | rs232496 |
| IM49 | 12 bp | chr3:56682065 | rs7642389 | | |
| IM50 | 12 bp | chr20:37048155 | rs1739651 | rs145870165 | |
| IM51 | 12 bp | chr5:128096988 | rs4836397 | | |
| IM64 | 12 bp | chr16:14216095 | rs201451896 | rs112858435 | rs75477279 |
| LR36 | 12 bp | chr4:98999722 | rs182020262 | rs17550217 | |
| LR41 | 12 bp | chr4:34074106 | rs190518698 | rs6852667 | |
| LR43 | 12 bp | chr5:86199060 | rs201282399 | rs10051666 | rs6881561 |
| LR44 | 12 bp | chr10:99898285 | rs78876983 | rs7905388 | rs7905384 |
| LR52 | 12 bp | chr16:63861440 | rs2434849 | | |

To assess the utility of specific mononucleotides for sequence based detection of MSI repeat length variation were analysed in a small panel of primary tumours and control tissues using Illumina sequencing. The selected 120 unstable mononucleotide repeats (7-12 bp) were amplified from FFPE tissue and sequenced using the Illumina MiSeq. Repeats within 30 bp of SNPs with a high minor allele frequency were selected. PCR was used instead of a capture based approach for two reasons. It is easier to obtain a good coverage of all regions from degraded DNA using PCR then pooling amplicons a roughly equimolar concentration. Using a capture based approach also risks having a high drop out rate of desired mononucleotide repeat sequences because many of the mononucleotide repeats are in regions of high homology which can lead to mispriming of probes and the capture of undesired sequences.

Primers were designed using Primer3 (Rozen and Skaletsky, 2000) or manually if Primer3 returned no suitable oligos. Primers designed manually had a Tm of 57° C.-60° C. The Tm was calculated as follows: Tm=4×(G+C)+2×(A+T). Primers were designed to create amplicons of ~300-350 bp. All primers were checked for common SNPs using SNP Check (https://ngrl.manchester.ac.uk/SNPCheckV2/snp-check.htm), off target binding using BLAST (http://blast.ncbi.nlm.nih.gov/Blast.cgi) or BLAT (Kent, 2002), and appropriate melting temperatures and absence of secondary structures using OligoCalc (http://www.basic.northwestern.edu/biotools/oligocalc.html) or Primer3. The primers were produced by either Metabion (Metabion International AG, Steinkirchen, Germany) or Biobasic (Bio Basic Inc., Markham, Canada) and purified by desalting. A list of all primers can be found in Table B below. The primers in this panel were tagged with overhang oligonucleotides to facilitate and reduce the cost of the downstream library preparation.

TABLE B

List containing amplicon/repeat name, amplicon position (genome build hg19), primers, and SNP rs numbers for SNPs in close proximity to mononucleotide repeats.

| Amplicon Name | Repeat length (bp) | Repeat Unit | Amplicon position | Forward Primer | Reverse Primer | SNP1 | SNP2 | SNP3 |
|---|---|---|---|---|---|---|---|---|
| CYP2C9 | N/A | N/A | chr10: 96740990-96741143 | TGCATGCAAGACAGGAGCC (SEQ ID NO: 1) | GGAGAACAAACTTACCTTGGGAA (SEQ ID NO: 2) | | | |
| BAT26 | 26 | A | chr2: 47641351-47641743 | CTTTAGAACTGGATCCAGTGG (SEQ ID NO: 3) | AAAAAGTGGAGTGGAGGAGG (SEQ ID NO: 4) | | | |
| Axin2 | 7 | C | chr17: 63532406-63532719 | AACCCAGTTTCTTTCCTTCTG (SEQ ID NO: 5) | GCCTCAACCTAGGACCCTTC (SEQ ID NO: 6) | rs35415678 | | |
| AL590078 | 8 | A | chr9: 26468834-26469145 | TCACCACTGGGGACTTTTTC (SEQ ID NO: 7) | TGAGCACCAAGTCATTCTG (SEQ ID NO: 8) | rs10967352 | | |
| MX1 | 8 | C | chr21: 42825925-42826244 | TAGAGGCAGCAGGCTCTCAG (SEQ ID NO: 9) | ACCCCACAAACCATGAAATC (SEQ ID NO: 10) | rs35138081 | | |
| HPS1 | 8 | C | chr10: 100186775-100187078 | CACAGCCCATTCCTGGAC (SEQ ID NO: 11) | GCCATTGCTTACATCTCATGG (SEQ ID NO: 12) | rs12571249 | rs12571245 | |
| IL1R2 | 8 | C | chr2: 102626258-102626576 | AGGACTCTGGCACCTACGTC (SEQ ID NO: 13) | TCGCAAGGAAAACTACAGCAG (SEQ ID NO: 14) | rs2282747 | | |
| DEPDC2 | 8 | C | chr8: 68926559-68926888 | TCTGGGAAAAAGCCCATAAC (SEQ ID NO: 15) | ACAACACCCTCTCACCCAAC (SEQ ID NO: 16) | rs4610727 | | |
| APBB2 | 8 | C | chr4: 41034386-41034688 | TGACTATGACAGGAGCTTAAAACTG (SEQ ID NO: 17) | CCCACACCACATTGTATGTAGAC (SEQ ID NO: 18) | rs4861359 | | |
| SLC4A3 | 8 | C | chr2: 220493959-220494271 | GGCACACCAGGAGAAAGAGG (SEQ ID NO: 19) | GCCCCGACCTACCATACAG (SEQ ID NO: 20) | rs597306 | | |
| AC079893 | 9 | A | chr7: 109669372-109669697 | CGTTTTTGTGGAAGCATACG (SEQ ID NO: 21) | CCAAATGGCAAATAAAAGAAGG (SEQ ID NO: 22) | rs4591959 | | |
| AL390295 | 9 | A | chr13: 35354677-35355008 | CATGATATGCCCATGTAGGG (SEQ ID NO: 23) | ATTGGTGAAGGAACCAGCAG (SEQ ID NO: 24) | rs9572382 | | |
| AL359238 | 9 | A | chr14: 83421969-83422285 | CAGCTGAAACCGAAGTGAAG (SEQ ID NO: 25) | TTGATGATCCTTTTGACACCAC (SEQ ID NO: 26) | rs72703572 | | |

TABLE B-continued

List containing amplicon/repeat name, amplicon position (genome build hg19), primers, and SNP rs numbers for SNPs in close proximity to mononucleotide repeats.

| Amplicon Name | Repeat length (bp) | Repeat Unit | Amplicon position | Forward Primer | Reverse Primer | SNP1 | SNP2 | SNP3 |
|---|---|---|---|---|---|---|---|---|
| AP003532_2 | 9 | A | chr11: 127624900-127625216 | CCCTTTACACCACATCAATGC (SEQ ID NO: 27) | GCAGGGCCCATCATACAG (SEQ ID NO: 28) | rs10893736 | | |
| TTK | 9 | A | chr6: 80751710-80752026 | TTCCAACTGTAAGAACAAGAGAG (SEQ ID NO: 29) | CACTTCAGAGTGATGTTGTCTTCA (SEQ ID NO: 30) | rs17254634 | | |
| C4orf6 | 9 | A | chr4: 5526980-5527306 | TCTTCCTTATGACAACCCACAC (SEQ ID NO: 31) | GAGCACCTTCCGACTCACTC (SEQ ID NO: 32) | rs886532 | rs113971480 | |
| AL954650 | 9 | C | chr1: 191926696-191927019 | TGCCAATATTTCAATTTTTCTCC (SEQ ID NO: 33) | AGACTATGCCTTGCCCAGAG (SEQ ID NO: 34) | rs77489859 | | |
| AL355154 | 10 | A | chr13: 82018382-82018682 | TCCAATAGGAAACTGAGAGCTATTC (SEQ ID NO: 35) | TGGAGCAGAGCAATAGAGAGG (SEQ ID NO: 36) | rs545694 | | |
| AVIL | 10 | A | chr12: 58202332-58202663 | CTGCAGAGCCACCATTC (SEQ ID NO: 37) | AGATGAACCAAGCCAGAAGC (SEQ ID NO: 38) | rs2277326 | | |
| ASTE1 | 11 | A | chr3: 130732912-130733215 | TGGAGGCCTCACTATGTTCC (SEQ ID NO: 39) | CTGGTGCACGGACTATGC (SEQ ID NO: 40) | rs58470539 | | |
| MRPL2 | 12 | C | chr6: 43021823-43022132 | GTGGGGACAGACCCAGTG (SEQ ID NO: 41) | GGGCAAGAGGCCTAACAGTG (SEQ ID NO: 42) | | | |
| EGFR | 13 | A | chr7: 55273419-55273760 | CACAGACTGTTTTGCAACG (SEQ ID NO: 43) | CTTGTGCTCCTTGCCTCACAG (SEQ ID NO: 44) | | | |
| FBXO46 | 14 | A | chr19: 46214532-46214834 | CTCCAGCGAGAAAGAATTGG (SEQ ID NO: 45) | ATTGATCCCTCACCGGAAC (SEQ ID NO: 46) | rs34505186 | | |
| FTO | 15 | A | chr16: 54147638-54147956 | TTTGTTATATCCCATTAGGTGCC (SEQ ID NO: 47) | ATCACGAGGTTGAGATCGAG (SEQ ID NO: 48) | rs77984007 | rs11348169 | |
| GM01 | 10 | A | chr11: 28894282-28894553 | TCAAGGCCAGGCAATTAATCAG (SEQ ID NO: 49) | ACTTGCTGAATGTCCAAGGTG (SEQ ID NO: 50) | rs7951012 | | |
| GM02 | 11 | A | chr1: 116245990-116246244 | GTGCTACATGAGATAGCTGGGA (SEQ ID NO: 51) | CTCTTCTGGCCAGTTCTATGTGT (SEQ ID NO: 52) | rs10802173 | rs148789685 | |
| GM03 | 8 | A | chr4: 120206298-120206557 | TGGAGTAAGACCCTTTAGGCAG (SEQ ID NO: 53) | AGACTCTGGAAGCAAATGGCA (SEQ ID NO: 54) | rs17050454 | rs10032299 | |
| GM04 | 7 | A | chr13: 92677409-92677684 | CCTTTTGGCCAGAGAATATGCC (SEQ ID NO: 55) | GGCATGAGGAAGTGAAGGGA (SEQ ID NO: 56) | rs9560900 | | |

TABLE B-continued

List containing amplicon/repeat name, amplicon position (genome build hg19), primers, and SNP rs numbers for SNPs in close proximity to mononucleotide repeats.

| Amplicon Name | Repeat length (bp) | Repeat Unit | Amplicon position | Forward Primer | Reverse Primer | SNP1 | SNP2 | SNP3 |
|---|---|---|---|---|---|---|---|---|
| GM05 | 9 | A | chr2: 216770642-216770900 | AGGTGTCAAGCAAGGACTCAG (SEQ ID NO: 57) | AGGCGTTTCACGTTGGAGG (SEQ ID NO: 58) | rs6704859 | | |
| GM06 | 9 | A | chr16: 77496387-77496667 | AGAGGCAGAATGTGAAAAGTC (SEQ ID NO: 59) | GCATTCTCCCACAGCACAAT (SEQ ID NO: 60) | rs6564444 | rs143453795 | rs145573459 |
| GM07 | 11 | A | chr7: 93085548-93085828 | GGAGGGACATGTGTTTCCAAAT (SEQ ID NO: 61) | CACAATGAGCCAAGTCTCACA (SEQ ID NO: 62) | rs2283006 | | |
| GM08 | 8 | A | chr21: 36574923-36575189 | AGCAACCTCTTAAATCCAGTACT (SEQ ID NO: 63) | TGGGCTTCTTGACTTTGGA (SEQ ID NO: 64) | rs2834837 | rs115025058 | |
| GM09 | 8 | A | chr20: 6836843-6837099 | TTTTCAGGACAAAGAGCAAGGT (SEQ ID NO: 65) | CTGGGTTCCATCTTGTGGGG (SEQ ID NO: 66) | rs6038623 | | |
| GM10 | 9 | A | chr1: 59891529-59891795 | ATCAGCTGACTCCTTACCCT (SEQ ID NO: 67) | TGGGGTGAGAGATGGACATG (SEQ ID NO: 68) | rs946576 | rs182557762 | |
| GM11 | 9 | A | chr5: 166099809-166100081 | CTCATGGTTAATACAATTAGGCACA (SEQ ID NO: 69) | ACATGGTGTGCTACCTTTCA (SEQ ID NO: 70) | rs347435 | | |
| GM13 | 11 | A | chr12: 107492450-107492711 | TTCTTCAGGGCCCATTATTGT (SEQ ID NO: 71) | TGAGGAATGTGCAGTTGACAC (SEQ ID NO: 72) | rs34040859 | rs77265275 | rs201488736 |
| GM14 | 11 | A | chr3: 177328721-177329014 | AGCTTGGCCATATTTGTGCA (SEQ ID NO: 73) | ACTTGATAGGGTTAAATGTCCGT (SEQ ID NO: 74) | rs6804861 | | |
| GM15 | 9 | A | chr7: 97963570-97963830 | TGCCTTCGAGTTTAAATGCCT (SEQ ID NO: 75) | GCCTCGTTATTTTGTGTGCC (SEQ ID NO: 76) | rs6465672 | | |
| GM16 | 8 | A | chr6: 100743524-100743782 | GCCACACTGACTTTGAACCTT (SEQ ID NO: 77) | ACAGCTTCTTCCTCACTCTACT (SEQ ID NO: 78) | rs7765823 | | |
| GM17 | 9 | A | chr11: 95550977-95551231 | TCCCTAGAAAGAGAACGATTGTAAAA (SEQ ID NO: 79) | AAATGCCCACCAAGATTGTAAAA (SEQ ID NO: 80) | rs666398 | | |
| GM18 | 12 | A | chr10: 8269462-8269727 | GGGGAGAAGACGGTTGAACT (SEQ ID NO: 81) | ACTGGTTCACTGGCCTTTTG (SEQ ID NO: 82) | rs113251670 | rs189036006 | rs533236 |
| GM19 | 7 | A | chr11: 114704247-114704523 | AGGTAAAGTCAGACACAATCCCA (SEQ ID NO: 83) | ACCCTCATGTTTCCCACCTCA (SEQ ID NO: 84) | rs142833335 | rs190597109 | rs10502196 |
| GM20 | 8 | A | chr7: 142597420-142597679 | GCAATCACATTTGCATTGGTTTT (SEQ ID NO: 85) | TGACTATGAGCTCCACAAACGTA (SEQ ID NO: 86) | rs6961869 | rs6961877 | |

TABLE B-continued

List containing amplicon/repeat name, amplicon position (genome build hg19), primers, and SNP rs numbers for SNPs in close proximity to mononucleotide repeats.

| Amplicon Name | Repeat length (bp) | Repeat Unit | Amplicon position | Forward Primer | Reverse Primer | SNP1 | SNP2 | SNP3 |
|---|---|---|---|---|---|---|---|---|
| GM21 | 9 | A | chr3: 142695286-142695560 | TTCTCCATTGGAAGTATTTGGGA (SEQ ID NO: 87) | TGTGTATTCAGGGTCCAGGG (SEQ ID NO: 88) | rs185182 | | |
| GM22 | 10 | A | chr14: 43400950-43401207 | TCATAACCAAGAGACCACCT (SEQ ID NO: 89) | TGTGATAGGGAAACACACGA (SEQ ID NO: 90) | rs58274313 | | |
| GM23 | 9 | A | chr5: 11345800-11346075 | CAGCATAAATCCAATGGCTATG (SEQ ID NO: 91) | TCAGATTGCAAAGGGGTACA (SEQ ID NO: 92) | rs184237728 | | |
| GM24 | 7 | A | chr10: 117432031-117432299 | AAACATTTCGACTGTGTGCAA (SEQ ID NO: 93) | TTCTTCTTTCCCCAAATGA (SEQ ID NO: 94) | rs2532728 | | |
| GM25 | 7 | A | chr3: 110871894-110872161 | TGGGATTAGGGAAGGGAGAG (SEQ ID NO: 95) | GGCCCCTCCCCAACTAAAAT (SEQ ID NO: 96) | rs74593281 | | |
| GM26 | 10 | A | chr14: 49584656-49584913 | CCTTCCTTTGATCCGCAAGC (SEQ ID NO: 97) | CTGCCACTTAGGAACTGGAG (SEQ ID NO: 98) | rs187027795 | rs11628435 | |
| GM27 | 7 | A | chr11: 85762061-85762349 | TTTTTGTTGCCCATTTCCTC (SEQ ID NO: 99) | AGGGTACTGACCCTAGCTCCA (SEQ ID NO: 100) | rs669813 | rs181565251 | rs146406522 |
| GM28 | 9 | A | chr5: 29209275-29209526 | CTCAGACAAAGACATACGAAGCC (SEQ ID NO: 101) | TTGGTTCTACAGTAATTGTGCTTCT (SEQ ID NO: 102) | rs4130799 | | |
| GM29 | 10 | A | chr3: 70905468-70905731 | CCCTCCCAAATGTCAAGTGT (SEQ ID NO: 103) | CCCACCCACACTCTTTTGTT (SEQ ID NO: 104) | rs2687195 | | |
| GM30 | 7 | A | chr14: 53111446-53111710 | TCAATGCTATTGGCCTATAAAGAGT (SEQ ID NO: 105) | ATGCATTTCCTTCTGGCCTA (SEQ ID NO: 106) | rs12880534 | | |
| IM07 | 10 | A | chr6: 100701756-100702050 | TCACCATCATCACCATGCTT (SEQ ID NO: 107) | TCTGGCAAACTCTTCACTGG (SEQ ID NO: 108) | rs189035042 | rs6915780 | |
| IM12 | 10 | A | chr8: 23602751-23603036 | AGTGGAGAAAACGGTTGTGG (SEQ ID NO: 109) | GAAGGCAGACAAGGGATTCA (SEQ ID NO: 110) | rs389212 | | |
| IM13 | 7 | A | chr2: 235496873-235497180 | GTGACCGCACAAAGTCACAC (SEQ ID NO: 111) | TCCAACAATACAGTCCATGA (SEQ ID NO: 112) | rs6721256 | rs183025093 | rs187312036 |
| IM14 | 7 | A | chr7: 80104285-80104624 | TCAAGACTCAGCCATTTCCA (SEQ ID NO: 113) | GGAAGCTGAGAGCAGGTTTT (SEQ ID NO: 114) | rs117760281 | | |
| IM15 | 8 | A | chr6: 91455016-91455307 | TCGTCAGGCTCTGCAACTAC (SEQ ID NO: 115) | CGATGGGATTGAATTGGAT (SEQ ID NO: 116) | rs1231482 | | |

TABLE B-continued

List containing amplicon/repeat name, amplicon position (genome build hg19), primers, and SNP rs numbers for SNPs in close proximity to mononucleotide repeats.

| Amplicon Name | Repeat length (bp) | Repeat Unit | Amplicon position | Forward Primer | Reverse Primer | SNP1 | SNP2 | SNP3 |
|---|---|---|---|---|---|---|---|---|
| IM16 | 9 | A | chr18: 1108609-1108894 | AGGACCTCGAGCTTCTCTTT (SEQ ID NO: 117) | TTCTTTTGCTTCCGTGTGTG (SEQ ID NO: 118) | rs114923415 | rs73367791 | rs59912715 |
| IM17 | 9 | A | chr13: 31831349-31831705 | TGCAACCAGAGGTTTTAAATCG (SEQ ID NO: 119) | CTCAATTCAGCAACAGGTCA (SEQ ID NO: 120) | rs932749 | | |
| IM19 | 7 | A | chr9: 82474924-82475277 | CAACCACAGTTTGCCAGCTA (SEQ ID NO: 121) | TCCTTGCTATCATTTGGAGAGA (SEQ ID NO: 122) | rs72736428 | rs186539440 | rs4877153 |
| IM20 | 7 | A | chr13: 57644542-57644833 | CCAGTTTCACATTTCGCTTGT (SEQ ID NO: 123) | TGGCAACAAAACAGTAACAGGA (SEQ ID NO: 124) | rs6561918 | | |
| IM21 | 8 | A | chr1: 215136329-215136605 | AGTGAATGGGCTTTTGGACTG (SEQ ID NO: 125) | AACTGGAGTGGTGGTGAACCTG (SEQ ID NO: 126) | rs181787229 | rs1901621 | rs1901620 |
| IM22 | 7 | A | chr7: 90135380-90135698 | CACCAGCTTTTCTCCCTTCA (SEQ ID NO: 127) | TGGCACTCAATACCAAACTGG (SEQ ID NO: 128) | rs10487118 | rs10487117 | rs139214151 |
| IM23 | 7 | A | chr6: 72729441-72729714 | GGTTTCTGTGCTGAATCTTGG (SEQ ID NO: 129) | AACCCCAGTTTTCTGCCTCT (SEQ ID NO: 130) | rs557365 | | |
| IM25 | 8 | A | chr12: 24568297-24568575 | CCATGGTACCACTGTGGAGT (SEQ ID NO: 131) | TAGAGGGGGCTTGAATGTTG (SEQ ID NO: 132) | rs10771087 | | |
| IM26 | 7 | A | chr3: 166053374-166053712 | GGGCTCGACTTGATTTACGA (SEQ ID NO: 133) | GGGAAGCAATCTCATGGCTA (SEQ ID NO: 134) | rs2863375 | | |
| IM27 | 7 | A | chr7: 35079029-35079302 | ACGCATGGAAAAAGAGGTTC (SEQ ID NO: 135) | CAAGGCTGGTATGGGTCAAT (SEQ ID NO: 136) | rs4723393 | rs112516918 | |
| IM28 | 7 | A | chr9: 5122829-5123102 | TGTGAATCCCTCCTGAAAT (SEQ ID NO: 137) | CCGCTGGTGGACTTTTACTC (SEQ ID NO: 138) | rs10815163 | | |
| IM32 | 11 | A | chr18: 42045361-42045640 | GCCAAAATGCCTAACTCCAA (SEQ ID NO: 139) | GGACTCGGATGGAAGACAAA (SEQ ID NO: 140) | rs8087346 | | |
| IM33 | 11 | A | chr8: 25731833-25732120 | AGGGTATGATTTGGGGTGT (SEQ ID NO: 141) | GTGGACCAAAGGAGCAGAAG (SEQ ID NO: 142) | rs202225742 | rs35644463 | rs113180202 |
| IM34 | 10 | A | chr7: 83714549-83714816 | TGAGGGTGGATGCTTCATTT (SEQ ID NO: 143) | CAGGATATTCCTCAGTTCCAGTTCC (SEQ ID NO: 144) | rs1524881 | | |
| IM35 | 10 | A | chr11: 84425027-84425322 | TCAAATGCAGACTCAACATGA (SEQ ID NO: 145) | AGCAGGAGGAGCCATCAATTC (SEQ ID NO: 146) | rs67283158 | rs10792775 | rs116387070 |

TABLE B-continued

List containing amplicon/repeat name, amplicon position (genome build hg19), primers, and SNP rs numbers for SNPs in close proximity to mononucleotide repeats.

| Amplicon Name | Repeat length (bp) | Repeat Unit | Amplicon position | Forward Primer | Reverse Primer | SNP1 | SNP2 | SNP3 |
|---|---|---|---|---|---|---|---|---|
| IM37 | 10 | A | chr17: 50813421-50813720 | CAGGCACACACACTTTCGTT (SEQ ID NO: 147) | TTCTCATGCAGTCAACCATTG (SEQ ID NO: 148) | rs2331498 | | |
| IM39 | 8 | A | chr2: 103233602-103233932 | AGAGTCCAAAGGTCGCTAA (SEQ ID NO: 149) | CCCTCACTGCCTGTAAACCT (SEQ ID NO: 150) | rs76771828 | rs190979688 | rs187315716 |
| IM40 | 8 | A | chr4: 84074695-84074985 | ATCACAAAAACAGGGGCCTA (SEQ ID NO: 151) | CCTTGTCTGGCTCAATCACC (SEQ ID NO: 152) | rs10516683 | | |
| IM41 | 8 | A | chr6: 147948700-147949027 | CTGCTCCACATTCCCATTCT (SEQ ID NO: 153) | TGGCAGGAAACATCTGTTCA (SEQ ID NO: 154) | rs1944640 | rs112075239 | |
| IM42 | 9 | A | chrX: 96502491-96502781 | TGGCTGAGTAAAATGGTGACA (SEQ ID NO: 155) | GCTTGGGGGAATTTCTTGAT (SEQ ID NO: 156) | rs1409192 | | |
| IM43 | 7 | A | chr21: 32873526-32873866 | CAGAAGGTCAGGACCACACA (SEQ ID NO: 157) | ATTTGGTGGGTTCCAGTGAG (SEQ ID NO: 158) | rs9981507 | | |
| IM44 | 9 | A | chr12: 9796844-9797182 | CCTCCTAGCATTCCATAGCAC (SEQ ID NO: 159) | TGCAACCTCGTAAGCTCATTT (SEQ ID NO: 160) | rs201750704 | rs4763716 | |
| IM45 | 11 | A | chr4: 99545274-99545564 | GCCACATTTGCTGGTATTCA (SEQ ID NO: 161) | TTTTTCCTCTGGGAAACCAT (SEQ ID NO: 162) | rs189419054 | rs2178216 | |
| IM47 | 12 | A | chr21: 22734257-22734517 | TGGTTCAGACATACACGTACAGG (SEQ ID NO: 163) | ATAACAGGCACAAGGGTGGA (SEQ ID NO: 164) | rs2588655 | rs149325240 | rs232496 |
| IM49 | 12 | A | chr3: 56681883-56682149 | CCTGGCAAATGATGCTTTAGA (SEQ ID NO: 165) | CCTCCCTCCTAGGCTCAAGT (SEQ ID NO: 166) | rs7642389 | | |
| IM50 | 12 | A | chr20: 37047920-37048224 | CGAGGCGGGTATTTACTTGA (SEQ ID NO: 167) | GGAGTTGGGGCAAAAATCAC (SEQ ID NO: 168) | rs1739651 | rs145870165 | |
| IM51 | 12 | A | chr5: 128096936-128097255 | CAAACCCCCCAGAGACACAC (SEQ ID NO: 169) | AACGTGGCTCTTTTATCCCATT (SEQ ID NO: 170) | rs4836397 | | |
| IM52 | 11 | A | chr21: 22846659-22846944 | GATGGAGGGCCCTTTAATTT (SEQ ID NO: 171) | CGATGAAGTGTTGATGTGAG (SEQ ID NO: 172) | rs74462385 | rs9982933 | rs2155801 |
| IM53 | 11 | A | chr9: 20662482-20662766 | GACAACTCCGAAGGGCAATA (SEQ ID NO: 173) | AGTTTGGGTTGCAAGACGTT (SEQ ID NO: 174) | rs182630429 | rs140426089 | rs12352933 |
| IM54 | 11 | A | chr21: 33709922-33710213 | GCAACATTGAAATGCTGGAA (SEQ ID NO: 175) | TAACATTTGGGAGGGGGAAT (SEQ ID NO: 176) | rs13046776 | | |

TABLE B-continued

List containing amplicon/repeat name, amplicon position (genome build hg19), primers, and SNP rs numbers for SNPs in close proximity to mononucleotide repeats.

| Amplicon Name | Repeat length (bp) | Repeat Unit | Amplicon position | Forward Primer | Reverse Primer | SNP1 | SNP2 | SNP3 |
|---|---|---|---|---|---|---|---|---|
| IM55 | 7 | A | chr3: 143253627-143253930 | GCTGAATAGCGGGATCAAAA (SEQ ID NO: 177) | GGAATTAGGTACCAGATCTCCTTT (SEQ ID NO: 178) | rs13099818 | | |
| IM57 | 8 | A | chr3: 81209863-81210156 | GATTATCAGCCCAGGGAGGT (SEQ ID NO: 179) | ATGGCAGCACTTGGGAAATTA (SEQ ID NO: 180) | rs35085583 | | |
| IM59 | 8 | A | chr8: 108358809-108359137 | TATGGCTGCAGCATTACCAG (SEQ ID NO: 181) | GCCAGAGTCCACAGACTCAA (SEQ ID NO: 182) | rs10156232 | | |
| IM61 | 7 | A | chr12: 73576301-73576606 | GAGCAAGGCATTTGAATCTG (SEQ ID NO: 183) | ATATGAGGCGCTCTCTCTCG (SEQ ID NO: 184) | rs34696106 | | |
| IM63 | 8 | A | chr3: 115815913-115816216 | TGCCTTTGGTTGTACCTTTG (SEQ ID NO: 185) | TCAAGTGAGCCTTGTGGAAA (SEQ ID NO: 186) | rs34764455 | | |
| IM64 | 12 | A | chr16: 14215981-14216240 | CCTTCCCGTTCTTTCTCTT (SEQ ID NO: 187) | AAGGTAGGTGACCGGCTGAT (SEQ ID NO: 188) | rs201451896 | rs112858435 | rs75477279 |
| IM65 | 11 | A | chr13: 25000797-25001149 | GCATCTCAAACTGTGCCTGT (SEQ ID NO: 189) | CACGGGTCTAACTGTCCTCA (SEQ ID NO: 190) | rs7324645 | rs9511253 | |
| IM66 | 7 | C | chr17: 48433883-48434148 | CCACTCCAGCAAGTCTCCAG (SEQ ID NO: 191) | CAAGGGCCTGCTGTATGTCA (SEQ ID NO: 192) | rs147847688 | rs141474571 | rs4794136 |
| IM67 | 7 | C | chr7: 22290637-22290990 | AGCCCATGTTTTCACAGAA (SEQ ID NO: 193) | TACCAGTGCCCTAAACAGG (SEQ ID NO: 194) | rs67082587 | rs57484333 | |
| IM68 | 8 | C | chr12: 129289515-129289789 | TTCTAGACACAGACCGCACACG (SEQ ID NO: 195) | GGGACTGCCACTAGTAGCTCA (SEQ ID NO: 196) | rs10847692 | | |
| IM69 | 7 | C | chr9: 92765658-92765989 | TGGGGCAGTTTCTATTCTG (SEQ ID NO: 197) | ATCAGTTTTCGATGGGGAGA (SEQ ID NO: 198) | rs1036699 | | |
| LR01 | 11 | A | chr13: 97387292-97387567 | TTGGATGCTGGATTTTGACA (SEQ ID NO: 199) | CTCATATCCCCCTCCCAGAA (SEQ ID NO: 200) | rs1924584 | rs4771258 | |
| LR02 | 8 | C | chr4: 134947615-134947875 | TATTGGCCAGGAATTTTTGC (SEQ ID NO: 201) | GGAGCTCACGCTAATGACCT (SEQ ID NO: 202) | rs189671825 | rs192703656 | rs1499878 |
| LR04 | 7 | C | chr1: 4676948-4677234 | CCCCAAGCTGTTTCCTCCAT (SEQ ID NO: 203) | GCTGGGGCAAGAAATTCAGC (SEQ ID NO: 204) | rs113646106 | rs2411887 | |
| LR05 | 9 | C | chr2: 10526489-10526814 | GAGCTGCCTACTCCGCTGACT (SEQ ID NO: 205) | GCCACTGATGATGACAACCTCCT (SEQ ID NO: 206) | rs111286197 | rs13431202 | |

TABLE B-continued

List containing amplicon/repeat name, amplicon position (genome build hg19), primers, and SNP rs numbers for SNPs in close proximity to mononucleotide repeats.

| Amplicon Name | Repeat length (bp) | Repeat Unit | Amplicon position | Forward Primer | Reverse Primer | SNP1 | SNP2 | SNP3 |
|---|---|---|---|---|---|---|---|---|
| LR06 | 7 | C | chr18: 20089314-20089588 | CATCTAGCATTCTCTCATTTCAGC (SEQ ID NO: 207) | TGCCAAAACCAAAGACAAGG (SEQ ID NO: 208) | rs501714 | | |
| LR08 | 7 | C | chr11: 56546008-56546315 | GGCTGCTTAAGGGAAAGTGC (SEQ ID NO: 209) | CGTGTTTTGGTCAAAGTTGTG (SEQ ID NO: 210) | rs181578273 | rs7117269 | |
| LR10 | 9 | A | chr1: 81591297-81591555 | ATGTTTGGTGCATGAAATCTG (SEQ ID NO: 211) | TGAGTTCCACATGGCTCTTG (SEQ ID NO: 212) | rs111814302 | rs1768398 | rs1768397 |
| LR11 | 11 | A | chr2: 217217726-217218005 | TATTCCCCTTGTGTGGGAGA (SEQ ID NO: 213) | CAAAGAGAATGGGTGGGAGT (SEQ ID NO: 214) | rs13011054 | rs147392736 | rs139675841 |
| LR12 | 11 | A | chr14: 47404086-47404346 | GGTGAGGAAAGCACAAGGTC (SEQ ID NO: 215) | CCGTGGAATTTCTTCTGCAC (SEQ ID NO: 216) | rs187434561 | rs144159314 | |
| LR13 | 7 | A | chr8: 21786845-21787107 | TCCTCGTCCTCTCAGATGTGT (SEQ ID NO: 217) | TCAGGACTTAGCACCAGGAAA (SEQ ID NO: 218) | rs2127206 | | |
| LR14 | 9 | A | chr17: 69328365-69328640 | CCCGTTTTCAGACCAAGTGT (SEQ ID NO: 219) | TTGGAACAGGATGGGTGAAT (SEQ ID NO: 220) | rs9895642 | | |
| LR15 | 7 | A | chr8: 92077118-92077383 | TGATTCGGGCTTGGACTTAG (SEQ ID NO: 221) | GTCAATCACTTTGCCTGCTC (SEQ ID NO: 222) | rs56084507 | | |
| LR16 | 11 | A | chr3: 8522305-8522590 | GTTTGATCTCTGGGCCCTGTC (SEQ ID NO: 223) | GCCTCCTTAATCTCCTCCATC (SEQ ID NO: 224) | rs148171413 | rs6770049 | |
| LR17 | 11 | A | chr14: 55602913-55603194 | AGACCACCCCTTAGGCAAAC (SEQ ID NO: 225) | AGTGCAGCAAGGCAGATGAG (SEQ ID NO: 226) | rs79618905 | rs77482253 | rs1009977 |
| LR18 | 8 | A | chr1: 220493800-220494106 | TGGGGAGGGAACCTCATTAC (SEQ ID NO: 227) | CAGTGCCTGTTGAGTAGAACC (SEQ ID NO: 228) | rs191265856 | rs199830128 | rs74940412 |
| LR19 | 8 | A | chr12: 29508532-29508843 | TGAGTGCTGCTCATATTTTCC (SEQ ID NO: 229) | GGGGCTTCAGTCTCAGGATAG (SEQ ID NO: 230) | rs10843391 | rs186762840 | |
| LR20 | 8 | A | chr1: 64029521-64029836 | TCAGCCTATGAAGATCCTCTG (SEQ ID NO: 231) | AAGGAAGACGGGAAGACTG (SEQ ID NO: 232) | rs146973215 | rs191572633 | rs217474 |
| LR21 | 9 | A | chr15: 50189339-50189607 | TGGGTACAAAGTCAAGTCAAC (SEQ ID NO: 233) | TCTCCAAAGGCTTCTCCTTG (SEQ ID NO: 234) | rs182900605 | rs80237898 | |
| LR23 | 11 | A | chr2: 142013847-142014151 | TGTAGCCTAGGTAAAGAGGACAA (SEQ ID NO: 235) | CATTTAGCATTTTGCCATTCC (SEQ ID NO: 236) | rs434276 | rs146141768 | rs2413976 |

TABLE B-continued

List containing amplicon/repeat name, amplicon position (genome build hg19), primers, and SNP rs numbers for SNPs in close proximity to mononucleotide repeats.

| Amplicon Name | Repeat length (bp) | Repeat Unit | Amplicon position | Forward Primer | Reverse Primer | SNP1 | SNP2 | SNP3 |
|---|---|---|---|---|---|---|---|---|
| LR24 | 9 | A | chr1: 153779290-153779565 | TATGCCTTCTGGAGGAGTGG (SEQ ID NO: 237) | TGGAATAGCGGTAAGCTTG (SEQ ID NO: 238) | rs192329538 | rs1127091 | |
| LR25 | 7 | A | chr16: 63209414-63209676 | TTAACCTGCCAGCTCAGTTC (SEQ ID NO: 239) | GCTTCCACTCATTTGCATTG (SEQ ID NO: 240) | rs76192782 | rs79880398 | rs4949112 |
| LR26 | 10 | A | chr16: 80050164-80050433 | TGCATAGGCAGACCTTCAAAAC (SEQ ID NO: 241) | GAAAGCCTGATGTTTGACACC (SEQ ID NO: 242) | rs4989066 | rs187883346 | |
| LR27 | 8 | A | chr4: 72877320-72877604 | TTTGTCATTGCTGTCATGG (SEQ ID NO: 243) | CAACAAGGAATTGAATGATGC (SEQ ID NO: 244) | rs55894427 | rs74733006 | |
| LR28 | 9 | A | chr12: 81229619-81229925 | TGAGTCCCTTTTGAAATGTTG (SEQ ID NO: 245) | GCCAACCAATGGAGTTTTAAG (SEQ ID NO: 246) | rs185642078 | rs28576612 | rs10862196 |
| LR29 | 10 | A | chr6: 78198189-78198498 | CAATGTTTGATTAACCATGACG (SEQ ID NO: 247) | GCACTTTTCTCACACAATTTGG (SEQ ID NO: 248) | rs1778257 | | |
| LR30 | 10 | A | chr11: 105444906-105445201 | GCAGGAATTCATTCTGAAGC (SEQ ID NO: 249) | AACGCAGTGAGGAACAAAGG (SEQ ID NO: 250) | rs7933640 | | |
| LR31 | 8 | A | chr3: 62995387-62995657 | TGGATTTGCATCTGTGAATTG (SEQ ID NO: 251) | TTTTGATGGCTTTACTTTTCC (SEQ ID NO: 252) | rs183248146 | rs2367592 | |
| LR32 | 10 | A | chr19: 37967035-37967313 | CTGCCTATGCCAAACAAATG (SEQ ID NO: 253) | AGCACAAAGCCTTTTGTCAGC (SEQ ID NO: 254) | rs7253091 | | |
| LR33 | 11 | A | chr4: 138498516-138498782 | GAATAGCGGGAAGAACTGGA (SEQ ID NO: 255) | TGCATTCGAATCAGGAATGA (SEQ ID NO: 256) | rs200714826 | rs4637454 | rs111688169 |
| LR34 | 9 | A | chr3: 115376990-115377261 | CCCATCCTTAGACCCCAGAC (SEQ ID NO: 257) | GAAAATGAGACGCGAAAAGG (SEQ ID NO: 258) | rs187521190 | rs192106258 | rs9883515 |
| LR35 | 10 | A | chr8: 130384312-130384584 | AAAGCTTGTGGGTGATGGAG (SEQ ID NO: 259) | TGCTTGGAATAGGATGCTTTG (SEQ ID NO: 260) | rs4733547 | | |
| LR36 | 12 | A | chr4: 98999555-98999845 | TCCCCAGGACCCTAGTCTTC (SEQ ID NO: 261) | GGTGGCAAGCACTTTTGTAAG (SEQ ID NO: 262) | rs182020262 | rs17550217 | |
| LR39 | 10 | A | chr17: 66449171-66449485 | AGCATGGGAATAACGACAGG (SEQ ID NO: 263) | TCGTTGTGTTGGAGGTAGAGC (SEQ ID NO: 264) | rs2302784 | | |
| LR40 | 9 | A | chr2: 13447304-13447570 | AAAATGAACACTATGCATGTCAGG (SEQ ID NO: 265) | TTGCCTCTTGCAACTGATTG (SEQ ID NO: 266) | rs6432372 | | |

TABLE B-continued

List containing amplicon/repeat name, amplicon position (genome build hg19), primers, and SNP rs numbers for SNPs in close proximity to mononucleotide repeats.

| Amplicon Name | Repeat length (bp) | Repeat Unit | Amplicon position | Forward Primer | Reverse Primer | SNP1 | SNP2 | SNP3 |
|---|---|---|---|---|---|---|---|---|
| LR41 | 12 | A | chr4: 34073929-34074197 | CATGGACCGCTGATCTCTG (SEQ ID NO: 267) | GGAGGGATCTAGCCACCAC (SEQ ID NO: 268) | rs190518698 | rs6852667 | |
| LR43 | 12 | A | chr5: 86198899-86199207 | GGCAACAGCCTCATAACTGC (SEQ ID NO: 269) | GCTGTCTCCTGGCTCTAACC (SEQ ID NO: 270) | rs201282399 | rs10051666 | rs6881561 |
| LR44 | 12 | A | chr10: 99898182-99898454 | TTTGGCTGGGCCTGGTAG (SEQ ID NO: 271) | CAGAGTGCACCTCAGTGACC (SEQ ID NO: 272) | rs78876983 | rs7905388 | rs7905384 |
| LR45 | 7 | A | chr2: 226937965-226938246 | TGCAGAAGAGATACAGAAAGC (SEQ ID NO: 273) | TGCAAAAATCCCAGATTGAAG (SEQ ID NO: 274) | rs180896305 | rs1522818 | rs144175764 |
| LR46 | 8 | A | chr20: 10659968-10660261 | GAGTGTGGGAGAAGTCCTACG (SEQ ID NO: 275) | TTCAGGAGATGAAAAGGCTTG (SEQ ID NO: 276) | rs143884078 | rs182346625 | rs6040079 |
| LR47 | 7 | A | chr10: 20506574-20506830 | TCCCTGAAGGAAGAAAAATC (SEQ ID NO: 277) | GTGATTGTGAAGTTGGATTTGC (SEQ ID NO: 278) | rs11597326 | rs12256106 | |
| LR48 | 11 | A | chr12: 77988002-77988288 | ATTACCCATGGGGGATGTTG (SEQ ID NO: 279) | AGTTGGGAACATTCCTTCC (SEQ ID NO: 280) | rs11105832 | | |
| LR49 | 7 | A | chr15: 93618885-93619163 | ATCTGTAAGGATCGGGCTGA (SEQ ID NO: 281) | CAACACAACGCCATACTGCT (SEQ ID NO: 282) | rs80323298 | rs201097746 | rs12903384 |
| LR50 | 7 | A | chr2: 76556173-76556470 | TTCCCATTTGATGATCCTG (SEQ ID NO: 283) | AGAGTTTTCCCCACTCAGCA (SEQ ID NO: 284) | rs925991 | rs144630203 | |
| LR51 | 7 | A | chr10: 51026570-51026831 | TGAATATGCCTCAAGCACCA (SEQ ID NO: 285) | AATGCAAACCTCCTAGGTTAAAA (SEQ ID NO: 286) | rs8474 | | |
| LR52 | 12 | A | chr16: 63861273-63861586 | GTGCTCTGCATCTCATACGC (SEQ ID NO: 287) | CCTCCTTGGCTAACTTGCTC (SEQ ID NO: 288) | rs2434849 | | |

Analysis of the Sequence Data for the 120 Repeats to Select the Best Caller for Analysing Indels in Mononucleotide Repeats.

The FFPE tissues consisted of a selection of 6 Lynch Syndrome tumours, matching normal mucosa for 5 of these tumours, and 6 MSS tumours (Table 1). For the matched normal tissue there was too little material to enable the sequencing of all 120 repeats so this material was only used for a selection of repeats. For the other samples the amount of available DNA was also in a limited supply. ~300 bp amplicons were produced using the high fidelity Pfu-based Herculase II Fusion DNA polymerase and 35 PCR cycles. Amplicons were quantified using Qiagen QIAxcel, then pooled at a roughly equimolar concentration. Agencourt AMPure XP beads were used for PCR clean-up. After PCR clean-up the amplicon pools were diluted to a concentration of 0.2 ng before Library Prep using the Illumina Nextera XT kit (Illumina, San Diego, Calif., United States of America).

TABLE 1

Tissue samples consisting of Lynch Syndrome tumours, matching normal tissue for the Lynch Syndrome tumours and MSS tumours.

| Samples | Sample Type | Lynch Syndrome Patients Number |
|---|---|---|
| U029 Tumour | Lynch Syndrome Tumour | U029 |
| U096 Tumour | Lynch Syndrome Tumour | U096 |
| U179_H03 Tumour | Lynch Syndrome Tumour | U179 |
| U179_H12 Tumour | Lynch Syndrome Tumour | U179 |
| U303 Tumour | Lynch Syndrome Tumour | U303 |
| U312 Tumour | Lynch Syndrome Tumour | U312 |
| U029 Normal | Normal Mucosa | U029 |
| U096 Normal | Normal Mucosa | U096 |
| U179 Normal | Normal Mucosa | U179 |
| U312 Normal | Normal Mucosa | U312 |
| 169259 | MSS tumour | n/a |
| 169736 | MSS tumour | n/a |
| 169836 | MSS tumour | n/a |
| 170146 | MSS tumour | n/a |
| 170402 | MSS tumour | n/a |
| 171223 | MSS tumour | n/a |

The initial screen of 120 homopolymers with neighbouring SNPs, identified from whole genome data, showed a high level of instability in five MSI tumours sequenced. The results showed 40% of the short 7 bp-9 bp A/T repeats, 80% of the longer 10 bp-12 bp A/T repeats and 33% of the G/C repeats showing instability in at least one tumour. Markers were defined as unstable if a marker had a deletion frequency >5% and a deletion frequency of at least twice that of any of the control samples for the 7-9 bp repeats, or 1.5 that of any of the control samples for the 10-12 bp repeats.

Using heterozygous SNPs located within 30 bp of the repeats the inventors were also able to show that there was an excess of repeats showing allelic bias of reads with deletions in the MSI-H samples.

10 markers from whole genome analysis, which were classed as unstable in at least 60% of the MSI-H samples and also had an area under the curve (AUC) of at least 0.9 were chosen for further investigation. 10 markers taken from the literature, which showed instability were also selected for further analysis giving 20 markers in total (as shown in table 2).

TABLE 2

Area under the receiver operating characteristic curve (AUC) for each marker in the final panel of repeats. This table shows the length of each repeat, the repeat unit, and the ability of each repeat to discriminate between MSI-H and MSS samples expressed as the area under the receiver operating characteristic curve.

| Marker Name | Size (bp) | Repeat Base | Number of Samples Sequenced | AUC |
|---|---|---|---|---|
| DEPDC2 | 8 | C | 36 | 0.645 |
| LR46 | 8 | A | 58 | 0.825 |
| AL359238 | 9 | A | 53 | 0.806 |
| AL954650 | 9 | C | 29 | 0.639 |
| AP003532_2 | 9 | A | 58 | 0.896 |
| TTK | 9 | A | 46 | 0.733 |
| AL355154 | 10 | A | 33 | 0.915 |
| AVIL | 10 | A | 39 | 0.927 |
| GM29 | 10 | A | 57 | 0.883 |
| LR32 | 10 | A | 57 | 0.910 |
| ASTE1 | 11 | A | 41 | 0.957 |
| GM07 | 11 | A | 58 | 0.968 |
| GM14 | 11 | A | 58 | 0.873 |
| LR11 | 11 | A | 55 | 0.919 |
| LR48 | 11 | A | 56 | 0.988 |
| IM49 | 12 | A | 58 | 0.958 |
| LR36 | 12 | A | 58 | 0.919 |
| LR44 | 12 | A | 58 | 0.994 |
| EGFR | 13 | A | 12 | 0.900 |
| FBX046 | 14 | A | 23 | 0.722 |

A larger number of tumours were required to define thresholds for calling instability and determine if the chosen panel of repeats is sufficient for differentiating between MSI-H and MSS tumours. A total of 92 tumour samples were obtained.

DNA from the 92 tumours was first assessed to identify how many tumours had a sufficient quantity and quality of DNA to produce amplicons of ~300 bp in length for a panel of 20 markers. The size of the panel was chosen because 20 markers should be sufficient to differentiate between MSI-H and MSS tumours and there was insufficient DNA for many of the tumours to amplify a larger panel. For 3 tumours there was too little starting material to be able to amplify 20 repeats. Out of the remaining 89 tumour DNA samples it was possible to amplify 58 of the samples using amplicons of ~300 bp.

The ability of each repeat to discriminate between the MSI-H samples and the MSS samples was assessed using the area under the receiver operating characteristic curve (AUC).

Receiver operating characteristic curves are a method of measuring true positive and false positive rates. In this case the AUC is a measure of how well a given homopolymer can differentiate between the MSI-H and MSS samples. An AUC of 1 is achieved if all the MSI-H samples have a higher deletion frequency than the MSS samples for a given repeat. Any randomly chosen MSI-H sample from the data set would in this case have a 100% chance of having a higher deletion frequency than any randomly chosen MSS sample from the data set. An AUC value of 0.5 would mean that a repeat has no discrimination power because there would be 50-50 chance that any randomly chosen MSI-H sample would have a higher deletion frequency than any randomly chosen MSS sample.

The AUC values for all the homopolymers in the final panel are shown in Table 2. On average, the AUC increases with repeat length up to a repeat length of 12 bp. This means that the longer repeats, up to a length of 12 bp, are better at discriminating between the MSI-H samples and MSS samples. This was expected because longer microsatellites are more prone to microsatellite instability events than shorter repeats. For the shorter repeats there will therefore be more repeats in MSI-H samples that have not been affected by a mutation, decreasing the ability of those repeats to discriminate between MSI-H samples and MSS samples. The 13 bp and 14 bp repeat have an AUC of 0.9 and 0.722 respectively. These are lower AUC values than seen in all the 12 bp and all but one of the 11 bp repeats (see Table 2). This could indicate that sequencing and PCR error are so high in these repeats that using the frequency of all deletions as a measure of instability is no longer as good for discriminating between MSI-H and MSS samples as it is for the shorter 11 bp and 12 bp repeats. On the other hand it could be that the chosen 13 bp and 14 bp repeat are less prone to MSI due to sequence context and there may be many other 13 bp and 14 bp repeat in the genome that are more unstable than these two.

For the 14 bp repeat FBX046 a low AUC could also be due to the presence of a sequence length polymorphism in some of the controls. One of the tumours had a sequence length polymorphism for this repeat which indicates there is a possibility that FBX046 could be polymorphic in some samples. FBX046 was removed from the preferred panel.

The inventors have determined that sequencing error is dependent to some degree on the length of the homopolymer. Therefore different thresholds for calling instability will be needed for different homopolymer lengths. Thresholds for calling a marker unstable can be determined for each repeat length by assessing the sensitivity and specificity of each of the individual markers. Sensitivity and specificity are used to measure test accuracy. Sensitivity is measured as the fraction of patients who have a condition and have a positive test result for it. Specificity is the fraction of patients who don't have a condition and have a negative for that condition. Therefore sensitivity and specificity can be summarised as:

Sensitivity=True Positives/(True Positives+False Negatives)

Specificity=True Negatives/(True Negatives+False Positives)

For this work a tumour was defined as MSI-H if it had previously been classed as MSI-H using a standard Promega MSI test (MSI Analysis System, Version 1.2: Promega, Madison, Wis., United States of America). Tumours were classed as MSS if no instability had been detected in any of the five markers from the Promega MSI test. For each of the short mononucleotide repeats sequenced, sensitivity and specificity curves were produced. Each of the sensitivity and specificity curves has the frequency of reads containing deletions on the x-axis. The y-axis of each sensitivity curve is the fraction of MSI-H samples. The sensitivity curve shows the fraction of MSI-H samples (y-axis) that have a deletion frequency of or below the deletion frequency shown on the x-axis, which is the sensitivity at each given deletion frequency. The x-axis of the specificity curve is the fraction of MSS samples. The specificity curve shows the fraction of MSS samples (y-axis) that have a deletion frequency of or above the frequency shown on the y-axis which is the specificity at each given deletion frequency.

Of the 8 bp repeats, LR46 (extracted from the whole genome analysis) has a higher sensitivity than DEPDC2 (taken from the literature) for deletion frequencies up to 40%. Both repeats have a 100% specificity or no false positives at a deletion frequency of 4.1%. At this deletion frequency LR46 has a sensitivity of 42.9% with 12 out of the 28 MSI-H samples detected, and DEPDC2 has a sensitivity of 26.1% with 6 out of the 23 sequenced MSI-H samples detected.

All of the 9 bp repeats have 100% specificity for a 5.5% deletion frequency and above. At a deletion frequency of 5.5% the two repeats AP003532_2 and TTK have the highest sensitivity with 57.1% and 43.5% respectively. The two repeats AL954650 and AL359238 have a sensitivity of 42.1% and 21.7% at this deletion frequency.

All of the 10 bp repeats have a 100% specificity at a deletion frequency of ≥14.2%. For a deletion frequency of 14.2% the repeat LR32 has a sensitivity of 82.1%, which is the highest for any of the 10 bp repeats at this deletion frequency. The other 10 bp repeats AVIL, AL3551554, GM29 have a sensitivity of 71.4%, 35.3% and 25.9% respectively.

For the 11 bp repeats, the repeat ASTE1 had the highest frequency of deletions in the control samples with a deletion frequencies ranging between 11.9%-19.75%. All of the 11 bp repeats have a 100% specificity at a deletion frequency of ≥9.8%.

All of the 12 bp repeats have a 100% specificity at a deletion frequency of ≥19.4%. At a deletion frequency of 19.4% the repeats LR44, LR36 and IM49 have a specificity of 92.9%, 75% and 64.3% respectively.

The 13 bp marker EGFR had a high dropout rate within the sequence data and was only sequenced in 12 of the 58 tumours. Only two out of the 12 tumours that this marker was sequenced in were MSS tumours. EGFR has a 100% specificity at a deletion frequency of ≥24%, but as this is only based on data from 2 MSS samples it is not considered dependable and thus it was determined that this need not be included in the final panel.

The presence of a polymorphism in the tumour PR10654/14 meant that the marker is less suitable for the use in an MSI test as the marker being potentially polymorphic means that a high deletion frequency is not necessarily an indication of MSI. It was therefore not included in the preferred final panel.

The final preferred panel of 18 markers was therefore taken as DEPDC2, LR46, AL359238, AL954650, AP003532_2, TTK, AL355154, AVIL, GM29, LR32, ASTE1, GM07, GM14, LR11, LR48, IM49, LR36, LR44 (loci further defined in table A and table B).

Optimisation of Thresholds Based for Differentiating Tumours by MSI Status

To assess the performance of the repeats for differentiating between MSI-H tumours and MSS tumours the preferred panel of 18 microsatellite loci or repeats was evaluated using different deletion frequencies as cut-offs. The preferred panel consisted of eighteen 8 bp-12 bp mononucleotide repeats, namely; DEPDC2, LR46, AL359238, AL954650, AP003532_2, TTK, AL355154, AVIL, GM29, LR32, ASTE1, GM07, GM14, LR11, LR48, IM49, LR36, LR44 (loci further defined in table A and table B).

Different thresholds were set for each repeat size.

Using the deletion frequency thresholds shown in Table 3 below the number of repeats passing the threshold for each tumour was plotted using a bar chart.

Using these thresholds, every MSI-H tumour had five or more repeats that met the threshold for calling instability. For the MSS samples there were up to three repeats which met the threshold for calling instability. Using these thresholds it is therefore possible to separate the MSI-H tumour and MSS tumours because the panel of 18 repeats is able to correctly classify every MSS and MSI-H cancer using a cut-off of 4 or 5 unstable repeats to classify a sample as MSI-H.

TABLE 3

Thresholds for each repeat size that minimise the number of misclassified repeats. This table shows the deletion frequency thresholds that give a minimum number of errors for each repeat size. For each threshold the table shows the number of errors, the false positive error rate, the false negative rate, and the percentage of errors for a panel of tumours consisting of 85% MSS tumours and 15% MSI-H tumours.

| Repeat Length | Deletion Frequency Threshold | Minimum No of Errors | FPR | FNR | % False Positive Errors (assuming 85% MSS) | % False Negative Errors (assuming 15% MSI-H) |
|---|---|---|---|---|---|---|
| 8 bp | 0.016 | 23 | 0.256 | 0.235 | 21.7 | 3.5 |
| 9 bp | 0.041 | 50 | 0.011 | 0.527 | 0.9 | 7.9 |
| 10 bp | 0.142 | 42 | 0.000 | 0.452 | 0.0 | 6.8 |
| 11 bp | 0.121 | 40 | 0.130 | 0.169 | 11.1 | 2.5 |
| 12 bp | 0.164 | 18 | 0.033 | 0.179 | 2.8 | 2.7 |

FPR = false positive error rate,
FNR = false negative error rate.

The sensitivity of the marker panel could easily be adjusted by adding more repeats. The specificity is more important because false positives can accumulate. Individual repeats being classed as unstable in MSS samples is therefore more of a problem than individual repeats being classed as stable in MSI-H samples. In fact because replication errors in MSI-H samples occur randomly it is expected that some of the repeats in MSI-H samples will not be affected by replication errors and will therefore remain stable. To better reflect this, different weighting can be placed on false positive and false negative errors. Different weightings of errors were assessed to see how they would affect the false positive and false negative error rates for the sequenced panel of tumours, and the number of unstable repeats in MSI-H and MSS tumour samples.

The weighting of different errors was adjusted so that a false positive error is 1.5× worse than a false negative error and the deletion frequency thresholds for calling a repeat unstable were adjusted to reflect this different cost of the two types of errors. The deletion frequency thresholds were set so that the cost of errors was minimised. This changed the thresholds for the 11 bp and 12 bp repeats reducing the false positive error rates for these repeats (see Table 4).

TABLE 4

Thresholds for each repeat size that minimise the cost of misclassified repeats given that a false positive error is 1.5× worse than a false negative error. This table shows the deletion frequency thresholds that give a minimum cost of errors for each repeat size. For each threshold the table shows the false positive error rate, the false negative rate, and the percentage of errors for a panel of tumours consisting of 85% MSS tumours and 15% MSI-H tumours.

| Repeat Length | Deletion Frequency Threshold | FPR | FNR | % False Positive Errors (assuming 85% MSS) | % False Negative Errors (assuming 15% MSI-H) |
|---|---|---|---|---|---|
| 8 bp | 0.016 | 0.256 | 0.235 | 21.7 | 3.5 |
| 9 bp | 0.041 | 0.011 | 0.527 | 0.9 | 7.9 |
| 10 bp | 0.142 | 0.000 | 0.452 | 0.0 | 6.8 |
| 11 bp | 0.174 | 0.051 | 0.277 | 4.3 | 4.2 |
| 12 bp | 0.194 | 0.000 | 0.226 | 0.0 | 3.4 |

FPR = false positive error rate,
FNR = false negative error rate.

The new deletion frequency thresholds (see Table 4) were then used to calculate how many repeats passed the thresholds for each tumour sample. Using the new thresholds all the MSI-H tumours still have 5 or more repeats that are classified as unstable while none of the MSS tumours have more than 2 unstable repeats. The panel of 18 repeats is therefore able to correctly classify every MSS and MSI-H cancer correctly using a cut-off of 3-5 unstable repeats to classify a sample as MSI-H. By weighting false positive errors as 1.5 times more costly than false negative errors the panel of 18 repeats is better able to differentiate between the MSI-H and MSS samples.

The weighting of different errors was adjusted further so that a false positive error is two times worse than a false negative error. The deletion frequency thresholds were adjusted so that cost of errors was minimised. As a result the thresholds for calling a repeat unstable were increased for both the 8 bp and 11 bp repeats (see Table 5). For the 10 bp -12 bp repeats there are no false positive errors using the current deletion frequency thresholds (see Table 5).

TABLE 5

Thresholds for each repeat size that minimise the cost of misclassified repeats given that a false positive error is 2× worse than a false negative error. This table shows the deletion frequency thresholds that give a minimum cost of errors for each repeat size. For each threshold the table shows the false positive error rate, the false negative rate, and the percentage of errors for a panel of tumours consisting of 85% MSS tumours and 15% MSI-H tumours.

| Repeat Length | Deletion Frequency Threshold | FPR | FNR | % False Positive Errors (assuming 85% MSS) | % False Negative Errors (assuming 15% MSI-H) |
|---|---|---|---|---|---|
| 8 bp | 0.037 | 0.023 | 0.608 | 2.0 | 9.1 |
| 9 bp | 0.041 | 0.011 | 0.527 | 0.9 | 7.9 |
| 10 bp | 0.142 | 0.000 | 0.452 | 0.0 | 6.8 |
| 11 bp | 0.198 | 0.000 | 0.369 | 0.0 | 5.5 |
| 12 bp | 0.194 | 0.000 | 0.226 | 0.0 | 3.4 |

FPR = false positive error rate,
FNR = false negative error rate.

The new deletion frequency thresholds found in Table 5 were used to analyse the panel of tumours. Using these thresholds reduced the number of repeats classed as unstable in the MSS tumours to two repeats. One repeat for the tumour 22_S11 and one repeat for the tumour 64_S34. All of the MSI-H tumours have 2 or more repeats which are classed as unstable. The panel of 18 repeats is therefore able to correctly classify all MSS and MSI-H tumours if a cut-off of 2 unstable repeats is used to classify a sample as MSI-H.

If the weighting of different errors is adjusted so that a false positive error is more than 5 times worse than a false negative error, then the resulting thresholds result in no false positive errors for any repeat size (see Table 6). At these thresholds the false negative error rate for the MSI-H samples is between 22.6% for the 12 bp repeats and 64.7% for the 8 bp repeats. For a panel of tumours which conform to division of 15% MSI-H tumours and 85% MSS tumours the error rate would be between 3.4% and 9.7% for each marker size. All of these errors are false negative errors. Because all 18 markers would be used together for classifying samples as MSI-H the false negative error rate for the full panel of repeats will be much lower than the false negative rate for individual repeat sizes.

TABLE 6

Thresholds for each repeat size that minimise the cost of misclassified repeats given that a false positive error is >5× worse than a false negative error. This table shows the deletion frequency thresholds that give a minimum cost of errors for each repeat size. For each threshold the table shows the false positive error rate, the false negative rate, and the percentage of errors for a panel of tumours consisting of 85% MSS tumours and 15% MSI-H tumours.

| Repeat Length | Deletion Frequency Threshold | FPR | FNR | % False Positive Errors (assuming 85% MSS) | % False Negative Errors (assuming 15% MSI-H) |
|---|---|---|---|---|---|
| 8 bp | 0.041 | 0.000 | 0.647 | 0.0 | 9.7 |
| 9 bp | 0.055 | 0.000 | 0.581 | 0.0 | 8.7 |
| 10 bp | 0.142 | 0.000 | 0.452 | 0.0 | 6.8 |
| 11 bp | 0.198 | 0.000 | 0.369 | 0.0 | 5.5 |
| 12 bp | 0.194 | 0.000 | 0.226 | 0.0 | 3.4 |

FPR = false positive error rate,
FNR = false negative error rate.

When the panel of 28 MSI-H tumours and 30 MSS tumours is analysed using the deletion frequency thresholds found in Table 6, there are 2 or more repeats classed as unstable in all of the MSI-H tumours. Because the thresholds for each repeat length have been set so that there are no false positive errors the panel of 18 repeats is able to correctly classify all MSS and MSI-H tumours if a cut-off of 1-2 unstable repeats is used to classify a sample as MSI-H.

In summary, the number of mononucleotide repeats was refined down to a panel of eighteen 8 bp-12 bp repeats consisting of repeats taken from the literature and repeats identified through the whole genome analysis. The panel comprises DEPDC2, LR46, AL359238, AL954650, AP003532_2, TTK, AL355154, AVIL, GM29, LR32, ASTE1, GM07, GM14, LR11, LR48, IM49, LR36, LR44. Looking at deletion frequencies in this panel of repeats was sufficient to distinguish between MSI-H and MMS tumours with a 100% sensitivity and specificity in a sample of 58 tumours (28 MSI-H tumours and 30 MSS tumours). The most practical set of thresholds were the ones that allowed no false positive markers in the MSS tumour group. The reason for this is that if thresholds are set so that unstable repeats are expected in the MSS samples then there is the risk that in some tumours the numbers of repeats classed as unstable can accumulate. Using these thresholds there were 2-17 unstable repeats in each of the MSI-H tumours. For an MSI test, a cut-off of 2 unstable repeats to call a tumour MSI-H should be used with this system because the odd unstable repeat can be found in MSS tumours (Yoon et al., 2013).

There were no polymorphisms as of dbSNP build 173 for the 18 markers of the final MSI testing panel, and no repeats showed potential polymorphism in the MSS tumours used to test these repeats. All repeats should therefore be monomor- phic, which means that the panel of repeats can be used without the need for a comparison between tumour and normal tissue. However, it is possible that polymorphisms in some of these repeats may be discovered in the future. This is another reason why a cut-off of 2 unstable repeats for calling a tumour MSI-H would be wise. It is however conceivable that it may not be possible to define a clear cut-off for identifying all MSI-H tumours because at the lower end of the spectrum there may be a continuum of instability levels between MSI-H, MSI-L and MSS tumours.

Another advantage of the MSI test in this example is that the test can be automated, reducing the need to use valuable staff time determine the MSI status of tumours. The monomolecular nature of next generation sequencing provides a quantitative approach to measuring deletion frequencies allowing automation. The approach of using deletion frequencies as thresholds for calling unstable markers lends itself well to automation, in contrast to the current tests where fragment analysis traces are subjectively analysed.

Example 2

Selection of an Alternative Panel of Mononucleotide Repeats

In parallel with the study described in Example 1, a second study was performed to assess and analyse the 120 7-12 bp markers shown in Table A for their potential use as sequence typed MSI markers. This second study initially focused on shorter markers (7-9 bp).

A batch of 25 short (7-9 bp in length) mononucleotide markers were tested using a cohort composed of 55 CRCs to identify the most informative markers among them. Eight markers were found as the most informative in terms of discrimination between MSI-high (MSI-H) and microsatellite stable (MSS) cases (GM9, GM11, GM17, LR20, LR24, LR49, IM16 and IM66—data not shown). To establish a system for calling instability, these 8 markers were combined together with the nine most informative markers of the panel in Example 1 (i.e. DEPDC2, AP003532_2, GM07, GM14, LR11, LR36, LR44, LR48 and IM49, all 8-12 bp in length) and were tested across a large cohort composed of 141 Spanish CRCs. A system was established (the weighted scoring system described in Example 1) for calling instability using the 17 markers with a sensitivity and specificity of 96% and 100%, respectively. The weighted scoring system was validated using an independent cohort of 70 CRCs referred from Edinburgh. The validation assay showed that the weighted scoring system was perfectly efficient in discrimination between MSI-H and MSS cases with a sensitivity and specificity of 100% for both.

The inventors have tested the utility of short mononucleotide repeats to assess the clonal characteristics of MSI-H cases and to have insight into the evolutionary history of the tested tumours. It was possible to establish the clonal characteristics and construct phylogenetic trees for the tested tumours (data not shown). Results from this assay support the feasibility of using short mononucleotide repeats to investigate the intratumour heterogeneity in MSI-H CRCs.

The panel of 17 markers is shown in table 7 below. As noted above, some of the markers showed commonality with the panel in Example 1.

TABLE 7

| Amplicon/marker | Homopolymer | Start | End | Homopolymer Start | Product Size | SNP | Chrom |
|---|---|---|---|---|---|---|---|
| LR49 | 7 (T) | 93618994 | 93619116 | 93,619,048 | 123 | rs80323298 | 15 |
| IM66 | 7 (GC) C | 48433923 | 48434025 | 48,433,967 | 103 | rs143225448 | 17 |
| LR20 | 8 (T) | 64029549 | 64029704 | 64,029,634 | 156 | rs217474 | 1 |
| GM11 | 9 (T) | 166099845 | 166099965 | 166,099,891 | 121 | rs347435 | 5 |
| LR24 | 9 (A) | 153779392 | 153779496 | 153,779,429 | 105 | rs192329538 | 1 |
| IM16 | 9 (T) | 1108732 | 1108867 | 1,108,767 | 136 | rs73367791 | 18 |
| GM17 | 9 (T) | 95551064 | 95551249 | 95,551,111 | 186 | rs666398 | 11 |
| GM9 | 8 (T) | 6836938 | 6837051 | 6,836,977 | 114 | rs79878287 | 20 |
| GM7 | 11 (A) | 93085649 | 93085797 | 93,085,748 | 149 | rs2283006 | 7 |
| LR36 | 12 (A) | 98999679 | 98999817 | 98,999,723 | 139 | rs187455164 | 4 |
| LR44 | 12 (A) | 99898232 | 99898370 | 99,898,286 | 139 | rs7905388 | 10 |
| LR48 | 11 (A) | 77988007 | 77988147 | 77,988,097 | 141 | rs11105832 | 12 |
| LR11 | 11 (A) | 217217787 | 217217903 | 217,217,871 | 117 | rs13011054 | 2 |
| AP003532_2 | 9 (T) | 127624984 | 127625150 | 127,625,067 | 167 | rs10893736 | 11 |
| DEPDC2 | 8 (G) | 68926646 | 68926777 | 68,926,683 | 132 | rs4610727 | 8 |
| GM14 | 11 (A) | 177328763 | 177328864 | 177,328,818 | 102 | rs6804861 | 3 |
| IM49 | 12 (A) | 56681995 | 56682136 | 56,682,066 | 142 | rs7642389 | 3 |

Exemplary forward and reverse primers for amplifying the markers along with associated SNP are shown in table 8a (forward primers) and 8b (reverse primers) below.

TABLE 8a

| Amplicon | FP |
|---|---|
| LR49 | TCGTCGGCAGCGTCAGATGTGTATAAGAGACAGGAGACCCCAGTCTTGCGAC (SEQ ID NO: 289) |
| IM66 | TCGTCGGCAGCGTCAGATGTGTATAAGAGACAGCAGGAGGTGCTGGAAATCC (SEQ ID NO: 290) |
| LR20 | TCGTCGGCAGCGTCAGATGTGTATAAGAGACAGGGCATTGCCCCTATATACTGT (SEQ ID NO: 291) |
| GM11 | TCGTCGGCAGCGTCAGATGTGTATAAGAGACAGCCTACGTATCTAAGTATTCTCCAGC (SEQ ID NO: 292) |
| LR24 | TCGTCGGCAGCGTCAGATGTGTATAAGAGACAGGGTAACCAAAGCAGGAAAACATT (SEQ ID NO: 293) |
| IM16 | TCGTCGGCAGCGTCAGATGTGTATAAGAGACAGGAATCAGCAGTGTTCATACCTTC (SEQ ID NO: 294) |
| GM17 | TCGTCGGCAGCGTCAGATGTGTATAAGAGACAGAGAAGTCAGTGCATGTGTCTT (SEQ ID NO: 295) |
| GM9 | TCGTCGGCAGCGTCAGATGTGTATAAGAGACAGTCCGTATTCCAGGAGTAAGAGT (SEQ ID NO: 296) |
| GM7 | TCGTCGGCAGCGTCAGATGTGTATAAGAGACAGGGTGGCTTGTTTTCATTTTGTC (SEQ ID NO: 297) |
| LR36 | TCGTCGGCAGCGTCAGATGTGTATAAGAGACAGGTGGTGACCCTGAACGTTAA (SEQ ID NO: 298) |
| LR44 | TCGTCGGCAGCGTCAGATGTGTATAAGAGACAGGAGGCCAAGAGTTCAAGACCA (SEQ ID NO: 299) |
| LR48 | TCGTCGGCAGCGTCAGATGTGTATAAGAGACAGGGGAGGAAGTATCTGGTCTTCT (SEQ ID NO: 300) |
| LR11 | TCGTCGGCAGCGTCAGATGTGTATAAGAGACAGTCCTGTGGTCTGTGAAGCTA (SEQ ID NO: 301) |
| AP0035322 | TCGTCGGCAGCGTCAGATGTGTATAAGAGACAGACTGTGGTTTTAATTTGCATTTCCC (SEQ ID NO: 302) |
| DEPDC2 | TCGTCGGCAGCGTCAGATGTGTATAAGAGACAGGTTCACACACATGCAAGCTG (SEQ ID NO: 303) |
| GM14 | TCGTCGGCAGCGTCAGATGTGTATAAGAGACAGCCCAGGCTAAAAGACCAAGA (SEQ ID NO: 304) |
| IM49 | TCGTCGGCAGCGTCAGATGTGTATAAGAGACAGGGTAGTTGGATCGCTTCAGG (SEQ ID NO: 305) |

TABLE 8b

| Amplicon | RP |
|---|---|
| LR49 | GTCTCGTGGGCTCGGAGATGTGTATAAGAGACAGAAGTCCCCACTTTGAAGATGTC (SEQ ID NO: 306) |
| IM66 | GTCTCGTGGGCTCGGAGATGTGTATAAGAGACAGCATCAGCCGCGTCGTAGG (SEQ ID NO: 307) |
| LR20 | GTCTCGTGGGCTCGGAGATGTGTATAAGAGACAGTTCCCAGTTCTGAATCTAGAAAGA (SEQ ID NO: 308) |
| GM11 | GTCTCGTGGGCTCGGAGATGTGTATAAGAGACAGACAGTGGGTTTCAAATGTCACTTC (SEQ ID NO: 309) |
| LR24 | GTCTCGTGGGCTCGGAGATGTGTATAAGAGACAGCCCTCTCTCCCTGGAATAAGT (SEQ ID NO: 310) |
| IM16 | GTCTCGTGGGCTCGGAGATGTGTATAAGAGACAGTTGTTCACTTTAGTAGGAACTGGT (SEQ ID NO: 311) |
| GM17 | GTCTCGTGGGCTCGGAGATGTGTATAAGAGACAGCCCACCAAGATTGTAAAATGTGA (SEQ ID NO: 312) |
| GM9 | GTCTCGTGGGCTCGGAGATGTGTATAAGAGACAGCTCAGAGGGAAGGTGGCA (SEQ ID NO: 313) |
| GM7 | GTCTCGTGGGCTCGGAGATGTGTATAAGAGACAGCATATGGGGTTTGGTCACATTTT (SEQ ID NO: 314) |
| LR36 | GTCTCGTGGGCTCGGAGATGTGTATAAGAGACAGCCTGGGTGTAAATGATGGGAA (SEQ ID NO: 315) |
| LR44 | GTCTCGTGGGCTCGGAGATGTGTATAAGAGACAGGATGAGAATTAGCATACCTTCCA (SEQ ID NO: 316) |
| LR48 | GTCTCGTGGGCTCGGAGATGTGTATAAGAGACAGGCACATTTACTTAAGCCCTGG (SEQ ID NO: 317) |
| LR11 | GTCTCGTGGGCTCGGAGATGTGTATAAGAGACAGGTGCATTTGAACATCGCCTC (SEQ ID NO: 318) |
| AP0035322 | GTCTCGTGGGCTCGGAGATGTGTATAAGAGACAGTGTGCCTTTAAAGTGACCTT (SEQ ID NO: 319) |

TABLE 8b-continued

| Amplicon | RP |
|---|---|
| DEPDC2 | GTCTCGTGGGCTCGGAGATGTGTATAAGAGACAGGAAG GGTAGGGAGATGCAGA (SEQ ID NO: 320) |
| GM14 | GTCTCGTGGGCTCGGAGATGTGTATAAGAGACAGCAGC AAAGGATAAACATTGTGGA (SEQ ID NO: 321) |
| IM49 | GTCTCGTGGGCTCGGAGATGTGTATAAGAGACAGCAGC CTCTTGAGTAGCTTGG (SEQ ID NO: 322) |

The panel was tested and showed 96% sensitivity and 100% specificity in a Spanish cohort of 141 CRC samples and the scoring scheme (developed to standardise the assay) showed a sensitivity and specificity of 100% in an independent cohort (provided from collaborators in Edinburgh)

Inclusion of SNPs to Distinguish Amplification and Sequence Error from True MSI

As can be seen from the examples above, the inventors have overcome the problems of calling indels in repetitive sequences where levels of PCR and sequence error may be high, by using linked single nucleotide repeats SNPs as a means of distinguishing between PCR and sequence error and indels caused by MSI.

The following Perl scripts were written to parse data, and perform two-tailed Fisher's exact tests.

FisherTest_AllDeletions.pl: Using output generated by COPReC, this script identifies repeats that are heterozygous for a neighbouring SNP and performs a two-tailed Fisher's exact test to determine if the fraction of deletions are significantly different between the two alleles. Repeats are defined as heterozygous if there are ≥100 paired end reads spanning both SNP and repeat for each allele, and one allele does not have less than 10% of the total read count. This script calculates the number of reads that contain a deletion and the number of reads that do not contain a deletion for each allele, and then uses these values to perform a Fisher's exact test. The Fisher's exact test calculations were performed using an external module integrated into the Perl script (Pedersen T., https://metacpan.org/pod/Text::NSP::Measures::2D::Fisher::twotailed).

FisherTest_IndividualIndels.pl: Using output generated by COPReC, this script identifies repeats that are heterozygous for a neighbouring SNP and perform a two-tailed Fisher's exact test to determine if the fraction individual indels is significantly different between the two alleles. Repeats are defined as heterozygous if there are ≥100 paired end reads spanning both SNP and repeat for each allele, and one allele does not have less than 10% of the total read count. For each allele this script categorises reads as; reads containing the indel size under investigation, or reads that do not contain the indel size under investigation. Next, this script calculates the number of reads in each category for both alleles and uses this as the input in the Fisher's exact test 2×2 contingency table. The two-tailed Fisher's exact test calculations were performed using an external open source module integrated into the Perl script (Pedersen T., https://metacpan.org/pod/Text::NSP::Measures::2D::Fisher::twotailed).

The inventors have identified that a sequence based approach can also enable allelic origin of instability to be investigated through the analysis of single nucleotide repeats (SNPs) located close to the repeat—typically 'close to' means within 100 base pairs, preferably within 70 base pairs, more preferably within 50 base pairs, most preferably within 30 base pairs of the mononucleotide repeat. Including these SNPs means that in heterozygous individuals it is possible to identify which allele homopolymer length variants belong to on reads that span both SNP and homopolymer. It should therefore be possible to determine if a specific indel is more prevalent on one allele than the other. If microsatellite instability is caused by random errors in microsatellite replication, which are not corrected by a cells compromised MMR system, then instability events are unlikely to affect both alleles of a short homopolymer. This is because short homopolymers have a low susceptibility to replication errors in vivo and two errors in the same position on both chromosomes are therefore less likely to occur. Sequencing amplicons which include both SNPs and microsatellite loci/mononucleotide repeat loci are therefore useful as it can provide a method by which instability can be distinguished from error, as PCR or sequencing error is unlikely to be allele specific because this type of error is likely to occur several times during a PCR reaction and both alleles will be susceptible.

In example 1 above all A/T repeats and most of the G/C repeats sequenced had neighbouring SNPs with a high minor allele frequency. Homopolymers with these neighbouring SNPs with a high minor allele frequency were chosen to enable the study of allelic bias for these homopolymers. The following data relates to example 1.

In FIG. 1 there are some examples of allelic bias in MSI-H tumours. For the 7 bp and 8 bp repeats, the reads containing a 1 bp deletion are mostly present on one allele (see FIG. 1 panels A-B). For the 11 bp repeat IM65 in the U029 tumour sample there is an imbalance between the two alleles both for the 1 bp deletion (Fisher's exact test: p-value<$10^{-100}$) and for the 3 bp deletion (Fisher's exact test: p-value $3.1 \times 10^{-72}$) (see FIG. 1 panel D). This suggests this repeat has had two separate replication mistakes, which have not been rectified by the compromised mismatch repair system. For the 12 bp repeat LR36 in the U303 tumour sample there are significantly more reads containing a 2 bp deletion on the allele with an A at the SNP site than the allele with a T (Fisher's exact test: p-value $4.22 \times 10^{-36}$).

To investigate allelic bias across all samples and all heterozygous repeats the Peri scripts FisherTest_AllDeletions.pl and FisherTest_IndividualIndels.pl were written. The Perl scripts identify repeats that are heterozygous for a neighbouring SNP and perform a Fisher's exact test to determine if the fraction of variant reads is significantly different between the two alleles. Repeats were defined as heterozygous if there were 100 paired end reads spanning both SNP and repeat for each allele and one allele did not have less than 10% of the total read count. The criteria of a minimum of 100 paired end reads per allele was used to prevent a misrepresentation of variant frequencies caused by PCR duplicates. The criteria that repeats were not analysed if one allele has less than 10% of the total read count was used because such an extreme allele imbalance might indicate sample contamination. The script FisherTest_AllDeletions6.pl calculates the fraction of reads that contain a deletion and the fraction of reads that do not contain a deletion for each allele and performs a Fisher's exact test to see if there is a significant difference in deletion distribution between the two alleles. The script FisherTest_IndividualIndels.pl calculates the fraction of reads that correspond to each individual insertion and deletion size, then calculates if there is a significant difference between the two alleles for each separate indel size.

Figure 2:
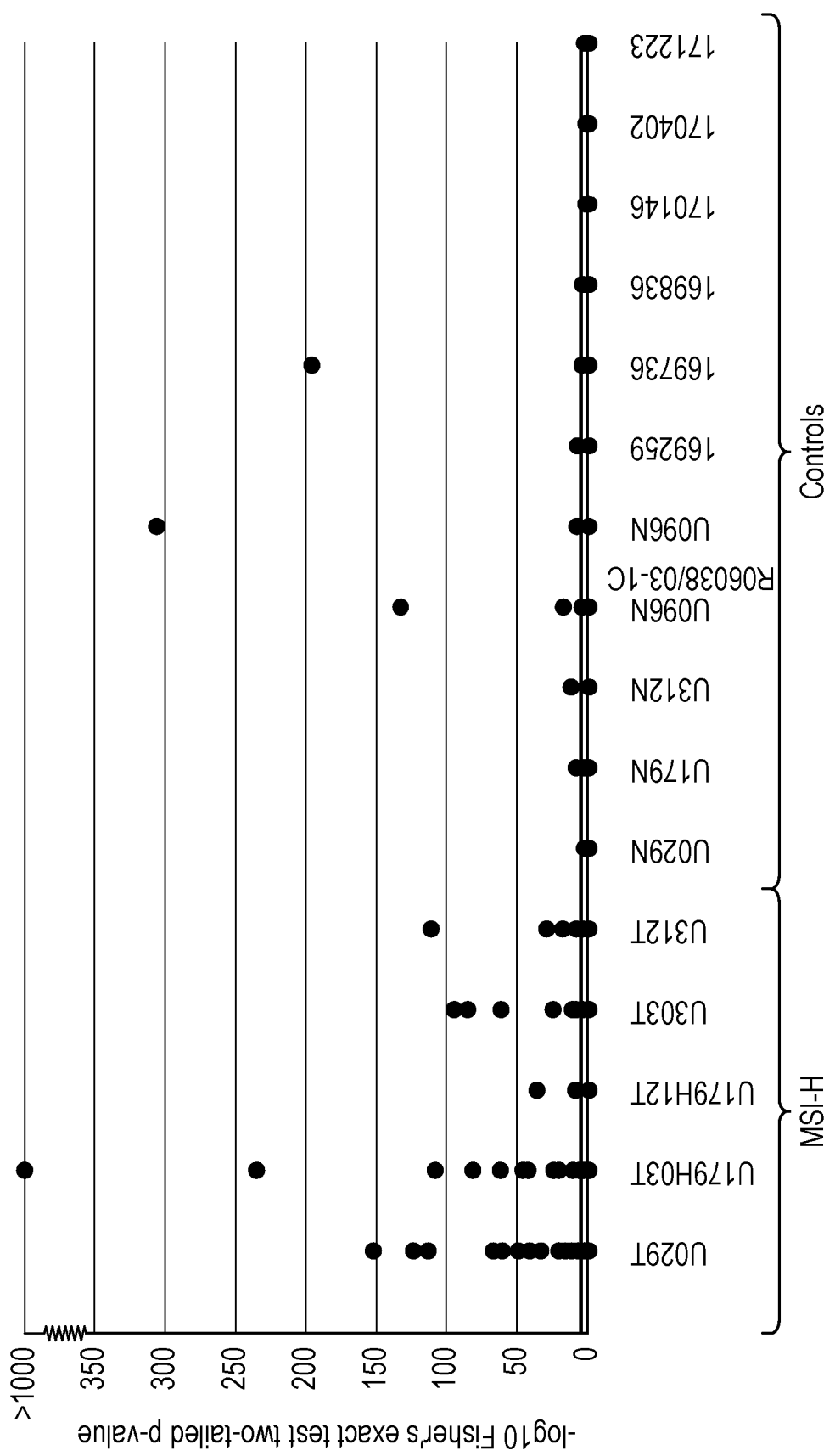
FIG. 2 shows allelic bias in deletion frequency for MSI-H samples and MSS samples measured using the p-value of a two tailed Fisher's exact test. The samples on the left=MSI-H samples, and the samples on the right=are the MSS (control) samples. The line corresponds to a Bonferroni corrected p-value of 0.01.

FIG. 2 shows the results for the Fisher's exact test where the significance of differences in total deletion frequencies between the two alleles of repeats were calculated. The repeats plotted in FIG. 2 include only repeats where the neighbouring SNP was classified as heterozygous. In some cases, a repeat had more than one neighbouring heterozygous SNP and in these cases, all heterozygous SNP repeat combinations were plotted. This method was chosen because different SNPs would have a different number of reads spanned both SNP and repeat. Therefore, different repeat and SNP combinations could provide different levels of significance for allelic bias. The results of the two-tailed Fisher's exact test indicate that there is more allelic bias in the MSI-H samples compared to the MSS samples (see FIG. 2). To Bonferroni correct a p-value of 0.01, this p-value was divided by the number of heterozygous SNP repeat combinations ($0.01/519=1.9\times10^{-5}$). A table containing the number of repeats with a statistically significant p-value can be found in Table 9. There were 52 repeats with a statistically significant p-value in the MSI-H samples compared to 12 in the controls. There are three mononucleotide repeats in control samples that have an allelic bias with a p-value below $10^{-20}$ (see FIG. 2). These include both U096 samples where there is a large bias between the alleles for the repeat LR16. As mentioned before the LR16 repeat is almost certainly polymorphic in patient U096 and this would explain the level of bias in deletion frequency seen between the two alleles of this repeat. The third repeat with a p-value below $10^{-20}$ is LR23 in the MSS tumour 169736. This is also a potential polymorphism.

TABLE 9

The number of repeat with a Bonferroni corrected p-value of 0.01 ($0.01/519 = 1.9 \times 10^{-5}$) for each tumour sample.

| Tumour sample | Sample Type | Number of repeats with a significant allelic bias (p-value ≤ $1.9 \times 10 - 5$) |
|---|---|---|
| U029T | MSI-H Tumour | 16 |
| U179H03T | MSI-H Tumour | 16 |
| U179H12T | MSI-H Tumour | 4 |
| U303T | MSI-H Tumour | 8 |
| U312T | MSI-H Tumour | 8 |
| U029N | Normal Mucosa | 0 |
| U179N | Normal Mucosa | 1 |
| U312N | Normal Mucosa | 1 |
| U096N R06038/03-1C | Normal Mucosa | 3 |
| U096N | Normal Mucosa | 2 |
| 169259 | MSS Tumour | 4 |
| 169736 | MSS Tumour | 1 |
| 169836 | MSS Tumour | 0 |
| 170146 | MSS Tumour | 0 |
| 170402 | MSS Tumour | 0 |
| 171223 | MSS Tumour | 0 |

Repeats with a neighbouring heterozygous SNP were also analysed to determine the significance of bias between the two alleles for individual indel sizes using the script FisherTest_IndividualIndels.pl. This was done using a two-tailed Fisher's exact test where the frequency of each individual indel size was interrogated. For each allele the reads were classed as containing the indel size under investigation or does not contain the indel size under investigation. For each repeat, the indel with the lowest p-value was recorded (Table 10). If there were multiple heterozygous SNPs neighbouring a repeat then the SNP where the lowest p-value was obtained was used.

The MSI-H samples have the highest number of heterozygous repeats with an indel event which is significantly biased between the two alleles. Up to a significance level of $p\text{-value}<10^{-10}$ there are a higher number of repeats in the MSI-H samples (see Table 10). However, the number of repeats sequenced differs between samples and the number of heterozygous repeats also differ between samples. For the MSI-H samples the fraction of the heterozygous repeats that contain allelic imbalance for individual indel sizes is generally higher than seen in the controls. The U179_H03 tumour sample has an allelic imbalance at a significance level of $p\text{-value}<10^{-10}$ for 46% of the heterozygous repeats, U029 tumour for 45% of the heterozygous repeats, U303 tumour for 21% of the heterozygous repeats, U179_H12 tumour for 10% of the heterozygous repeats, and the U312 tumour for 11% of the heterozygous repeats. The fraction of the heterozygous repeats that contain allelic imbalance for individual indel sizes is also high in the U096 controls. For the U096 sample from block R06038/03-1C there is an allelic imbalance at a significance level of $p\text{-value}<10^{-10}$ for 10% of the heterozygous repeats and for the other U096 sample (CAPP2 wax block label: U096 normal 23.12.02) an allelic imbalance in 17% of the repeats.

The U096 patient sample from block R06038/03-1C had three repeats with an allelic bias for 1 bp deletions of a significance level of $p\text{-value}<10^{-10}$. These three repeats were LR16 ($p\text{-value}<10^{-100}$), LR27 (p-value $2.9\times10^{-17}$), and LR51 (p-value $2.1\times10^{-18}$). LR16 is suspected to be polymorphic in patient U096. The U096 sample (U096 normal 23.12.02) shows allelic bias for a 1 bp deletion in the repeat LR16 which is believed to be a polymorphism.

TABLE 10

The number of repeats with allelic bias for individual indels sizes measured using the p-value of a two tailed Fisher's exact test.

| Status | Sample | Repeats with 2 alleles | p-value < 1E−10 | p-value < 1E−7 | p-value < 1E−5 | p-value < 1E−3 | p-value < 0.05 |
|---|---|---|---|---|---|---|---|
| Lynch Tumour | U029T | 42 | 19 | 19 | 19 | 20 | 25 |
| Lynch Tumour | U179T H03 | 37 | 17 | 19 | 19 | 20 | 24 |
| Lynch Tumour | U179T H12 | 41 | 4 | 6 | 6 | 9 | 13 |

TABLE 10-continued

The number of repeats with allelic bias for individual indels sizes measured using the p-value of a two tailed Fisher's exact test.

| Status | Sample | Repeats with 2 alleles | p-value < 1E−10 | p-value < 1E−7 | p-value < 1E−5 | p-value < 1E−3 | p-value < 0.05 |
|---|---|---|---|---|---|---|---|
| Lynch Tumour | U303T | 38 | 8 | 8 | 9 | 10 | 17 |
| Lynch Tumour | U312T | 45 | 5 | 7 | 9 | 10 | 17 |
| Normal Mucosa | U029N | 17 | 0 | 0 | 0 | 0 | 3 |
| Normal Mucosa | U179N | 20 | 0 | 1 | 2 | 4 | 9 |
| Normal Mucosa | U312N | 18 | 1 | 1 | 1 | 1 | 4 |
| Normal Mucosa | U096N R06038/03-1C | 29 | 3 | 3 | 3 | 4 | 10 |
| Normal Mucosa | U096N (23.12.02) | 6 | 1 | 2 | 2 | 2 | 3 |
| MSS Tumour | 169259 | 49 | 0 | 0 | 1 | 6 | 10 |
| MSS Tumour | 169736 | 39 | 1 | 1 | 1 | 3 | 9 |
| MSS Tumour | 169836 | 16 | 0 | 0 | 0 | 1 | 3 |
| MSS Tumour | 170146 | 19 | 0 | 0 | 0 | 0 | 2 |
| MSS Tumour | 170402 | 33 | 0 | 0 | 0 | 0 | 0 |
| MSS Tumour | 171223 | 37 | 0 | 0 | 0 | 0 | 5 |

Example 3

The inventors have investigated different ways of analyzing the data generated using the 17 marker panel of Example 2 in order to optimize the accuracy and sensitivity of discriminating between MMR proficient and deficient tumours using this panel. An optimized scoring procedure that incorporates the allelic distribution of the mutant repeats, and analysis of two series of tumours totaling 209 samples is described in this Example. The inventors confirm that, using this scoring procedure, the 17 marker panel is able to discriminate between MMR proficient and deficient tumours, even when constitutional DNA is not available. In the first series the method achieved 100% concordance with fragment analysis, while in the second 4 discordant samples were observed (corresponding to 97% concordance). Of these 2 showed discrepancies between fragment analysis and immunohistochemistry and one was reclassified after retesting using fragment analysis. These results indicate that the approach offers the option of a reliable, scalable routine test for MSI.

Figure 3:
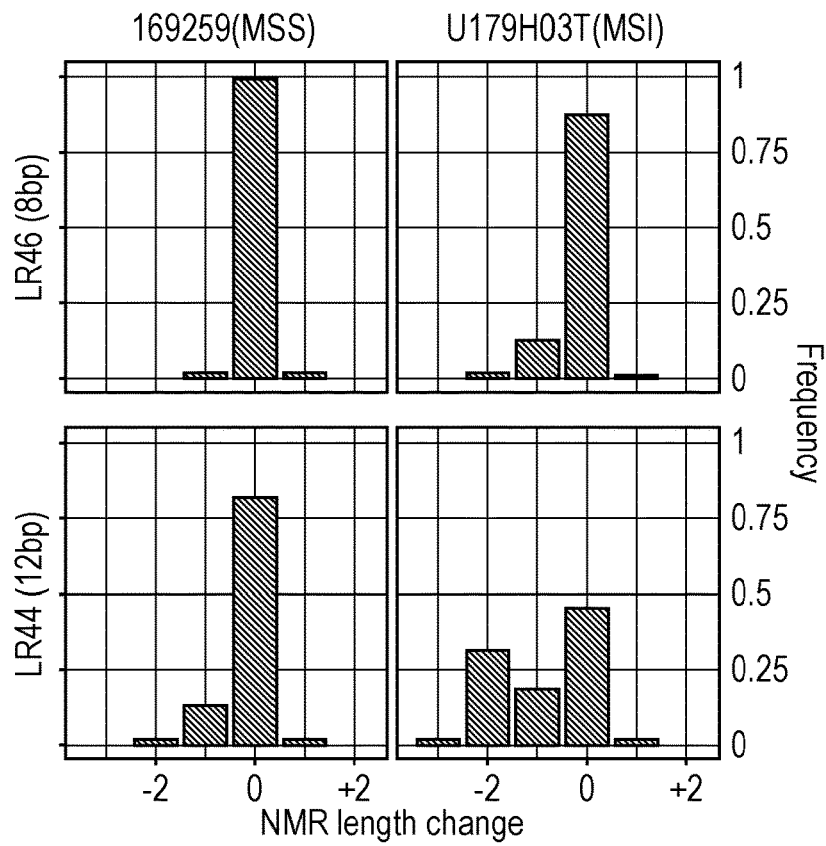
FIG. 3 shows example distributions of read frequencies. Relative frequencies of reads classified according to length are shown for MNRs LR46 (an 8 bp long poly-A tract) and LR44 (12 bp poly-A) in an MSS sample (169259) and MSI sample (U179H03T). The abscissa represents the deviation from the reference sequence length (hg19).

Experimental Assessment of Candidate NMRs and Delineation of a 17 Marker Panel:

As described in Examples 1 and 2, to eliminate potentially uninformative repeats, amplicons were designed for all 120 MNRs, and initially tested on FFPE material from 6 tumours from patients with Lynch syndrome, and 11 control samples consisting of 5 normal mucosa samples and 6 samples from sporadic microsatellite stable tumours (see Example 1). Amplicons were pooled, indexed, and sequenced to a target depth of 10,000 reads. Only results for amplicons represented by at least 100 paired end reads were analysed, and representative results are shown in FIG. 3.

FIG. 3A shows the relative frequencies of reads for two MNRs in an MMR proficient (MSS) and an MMR deficient (MSI) sample. A small fraction of insertion reads (+1 value in the abscissa) are observed in both MSI and MSS samples, but the frequency of deletions (−1, −2 and −3 values) differs between the two. However, for the longer repeat shown, reads representing deletions of more than one base pair are also observed in the MSS sample, while a second peak can be observed corresponding to a 2 bp deletion in the MSI sample. In all analyses, the sum of the frequencies of reads representing all deletions were used.

To illustrate levels of allelic variation observed, results from a single marker (LR46) are shown in FIG. 3B. The read distribution for each allele is plotted separately for an MSI and an MSS sample heterozygous for the flanking SNP. While the distribution for both the G and A alleles in the MSS sample is similar, reads representing a one base pair deletion are predominantly found in the G allele of the MSI sample.

From this initial assessment, MNRs were retained for further analysis only if they exhibited a deletion frequency >5% in 1 or more MSI sample, and these frequencies were also >1.5× higher than frequencies observed in all normal mucosa samples. 49 MNRs satisfied these criteria. Two previously described MNRs adjacent to SNPs (one in DEPDC2 (Alhopuro et al., 2008) and one in the intergenic repeat AL954650 (Sammalkorpi et al., 2007)) were also added to the analysis at this stage. These 51 NMRs were each typed in a minimum of 28 MSI and 30 MSS tumours, and ROC curves were generated to assess the ability of each to discriminate between MSI and MSS samples. This was performed by estimating the area under the curve (AUC) using the frequency of reads representing MNR deletion as the classification criterion (see methods), and classifying samples with a frequency above each threshold as MSI and below each threshold as MSS.

Figure 4A:
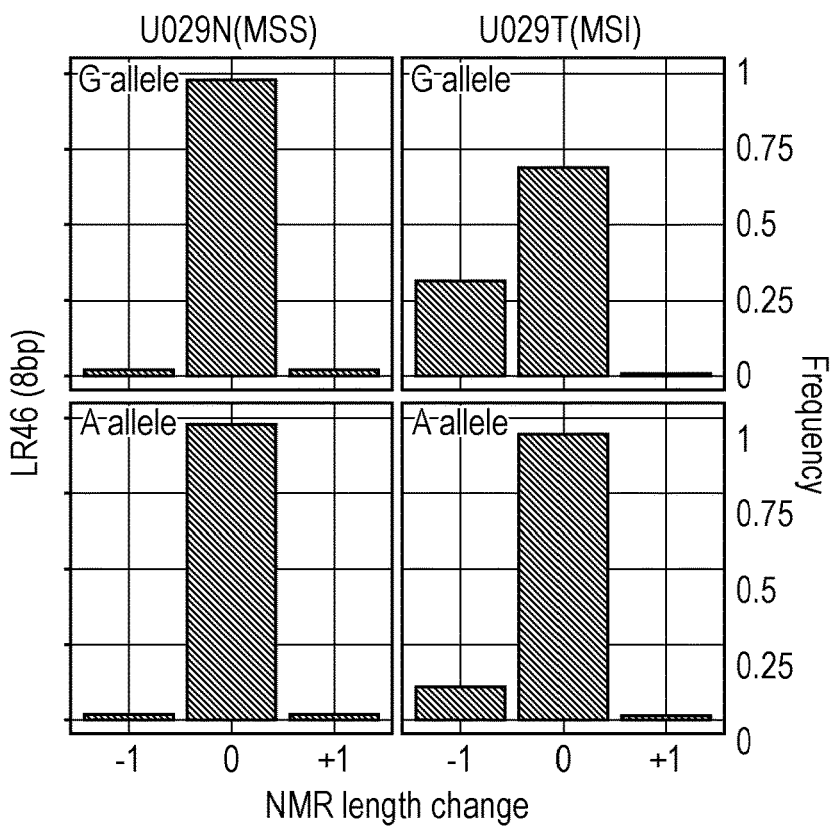
FIG. 4A shows an example of allelic bias. Allele specific read frequencies and sizes are shown for LR46 in two samples from a patient who is heterozygous for a flanking SNP (r56040079). U029N=normal somatic tissue, U029T=microsatellite unstable tumour.
Figure 4B:
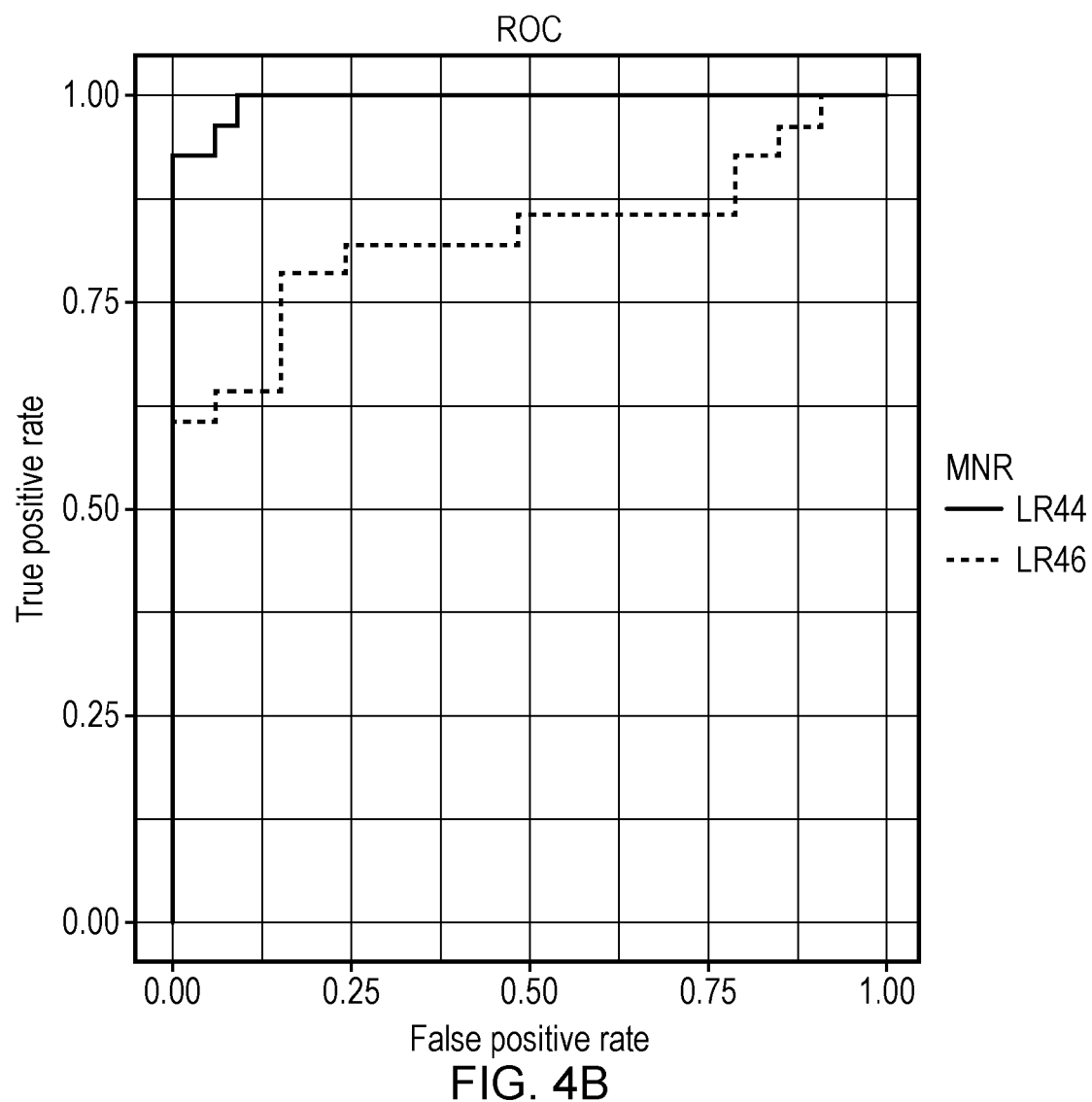
FIG. 4B shows classification of samples using single MNRs.

Representative examples of this analysis are shown in FIG. 4B which shows the ROC curves for the two poly-A MNRs; LR46 (8 bp) and LR44 (12 bp) used in FIG. 3. The AUC for LR46 was 0.83 (95% confidence interval 0.71-0.84) and 0.99 (0.98-0.99) for LR44.

Using the AUC as a criterion, 15 poly-A MNR repeats were selected and together with the two poly-C MNR with the largest AUC formed the final panel. As described in the methods sections, the primers for this panel were redesigned to produce shorter amplicons (primer sequences are available in Table 8a and 8b).

Tumour Classification Using the Selected Panel of Short MNRs

Figure 5:
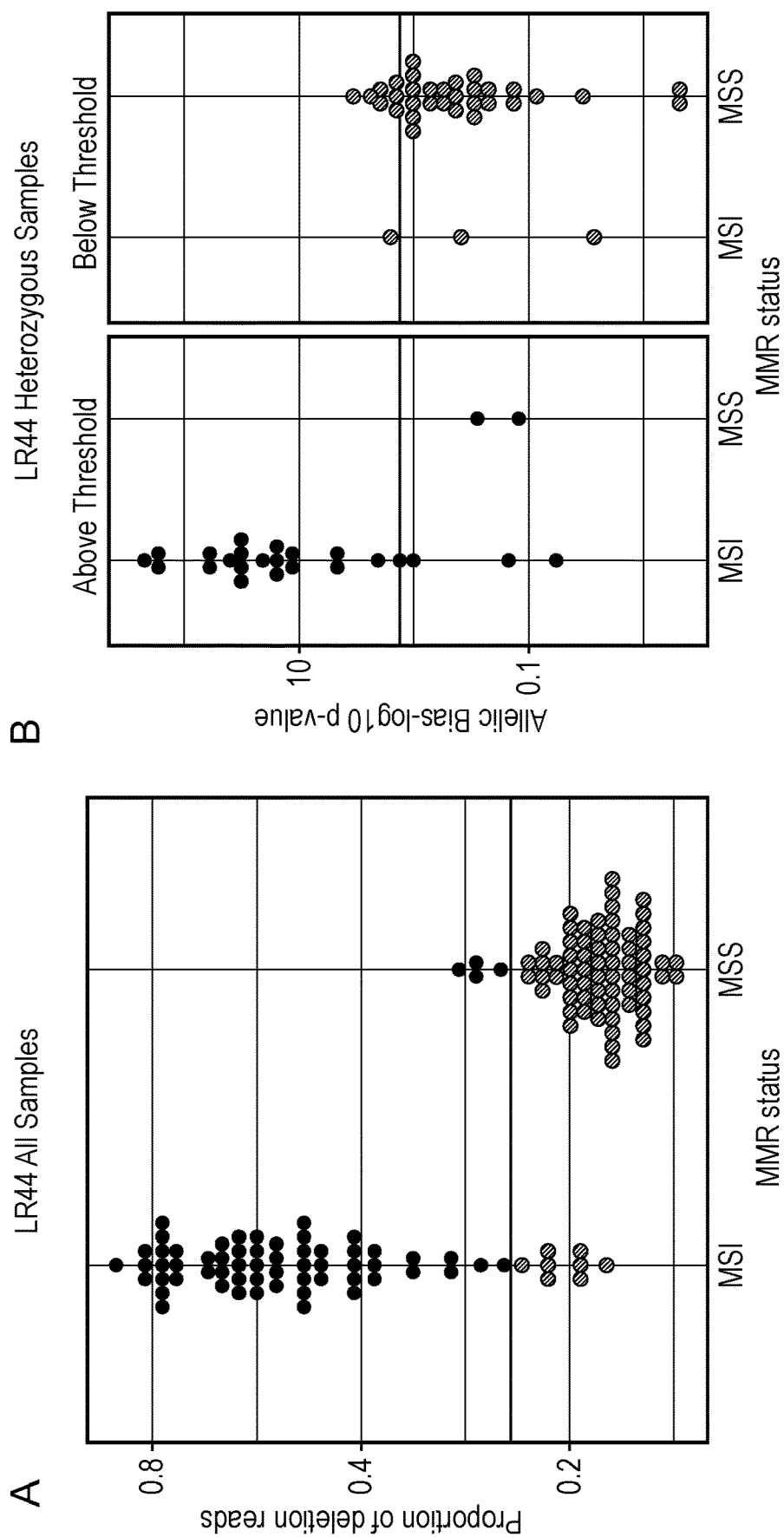
FIG. 5 shows a relative frequency of reads carrying a deletion in MSI and MSS samples for the MNR LR44. B. Analysis of allelic bias at the MNR LR44 for MSI and MSS samples stratified according to the proportion of reads showing deletions (see FIG. 3 and text).

Establishing the analysis parameters for an MSI test: To establish the parameters required by the classification procedure, the seventeen MNRs included in the final panel were typed in a set of 139 samples, of which 67 had been classified as MSI by fragment analysis (see material section). The deletion frequencies and allelic biases observed in these samples were used to establish thresholds for each marker and to estimate the probabilities described in the methods section for MSI and MSS samples. To illustrate this step, results for LR44, a 12 bp poly-A MNR, are presented in FIG. 5. FIG. 5A depicts the distribution of the relative frequencies of reads showing deletions in LR44. As expected, the deletion frequency is higher in MSI tumours. The horizontal line represents a threshold of 0.24 (see methods for the choice of threshold). The deletion frequency was higher than the threshold in 58 of the 66 MSI samples for which data were available for this marker, but only in 4 of the 72 MSS samples.

Of the 139 samples depicted in FIG. 5A, 60 samples (26 MSI and 34 MSS) were heterozygous for a SNP flanking the repeat, and the distribution of allelic bias for these samples is presented in FIG. 5B. Fisher's exact test was used to assess whether deletion reads were evenly distributed between both alleles. The Figure represents the resulting p-values in a $-\log_{10}(p)$ scale. The left hand panel shows the heterozygous samples that are above the threshold in FIG. 5A, the right hand panel those that are below. Overall, 21 MSI and 4 MSS samples had values above the threshold (i.e. had a bias significant at the 5% level; see methods for threshold choice). This corresponds to our expectation that allelic bias will be more common among MSI samples.

It is noteworthy that only 2 of the 4 MSS samples above the frequency threshold in FIG. 5A were heterozygous, and neither showed significant bias. In contrast, 27 out of the 32 MSI samples which were heterozygous showed a bias above the threshold (FIG. 5B). This difference is significant (p=0.03 two sided test), while the corresponding test for samples that do not reach the frequency threshold (panel B) does not suggest any difference between MSS and MSI samples (p=0.39). This is consistent with our assumption that allelic bias can help to discriminate between MSI and MSS samples.

For allelic bias and deletion frequencies, thresholds and relative numbers of samples above the respective threshold were determined for each of the 17 MNRs.

Analysis of a validation set: The parameters determined in first set of samples were then used to test the procedure in an independent data set consisting of 70 CRC samples, 36 of which had previously been classified as MSI and 34 as MSS.

Figure 6:
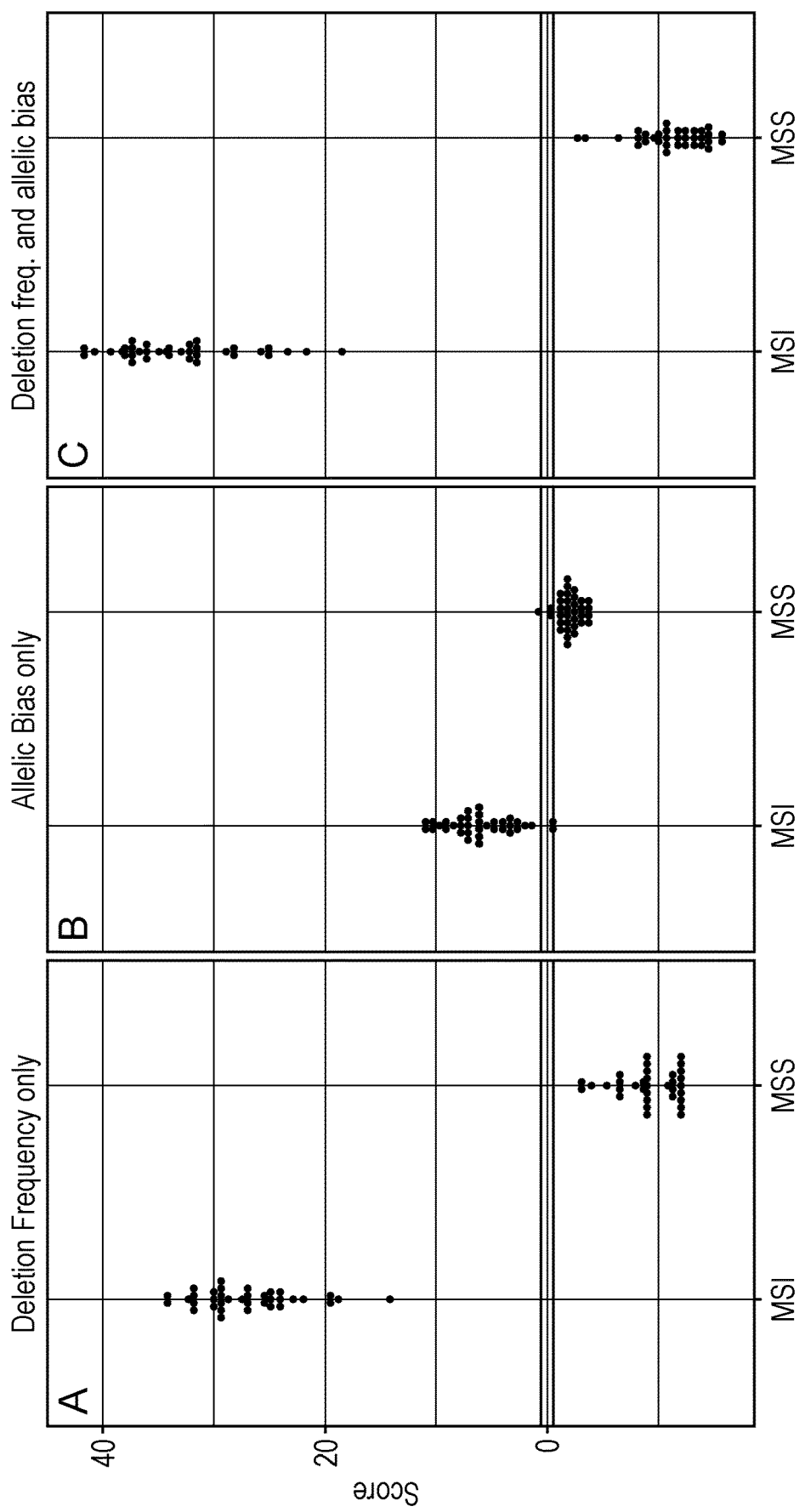
FIG. 6 shows classification of test samples using only deletion frequency data (A), only allelic bias data; (B) and both parameters combined (C).

FIG. 6 presents the contribution made to tumour classification by MNR length variation (panel A) and MNR allelic bias (panel B). This illustrates that while both contribute to the separation of the groups; changes in MNR length provide the main contribution. The final combined classification (panel C) is concordant with fragment analysis, achieving 100% sensitivity and specificity (95% confidence intervals 87%-100% and 90%-100% respectively) when fragment analysis is used as the reference technique.

Figure 7:
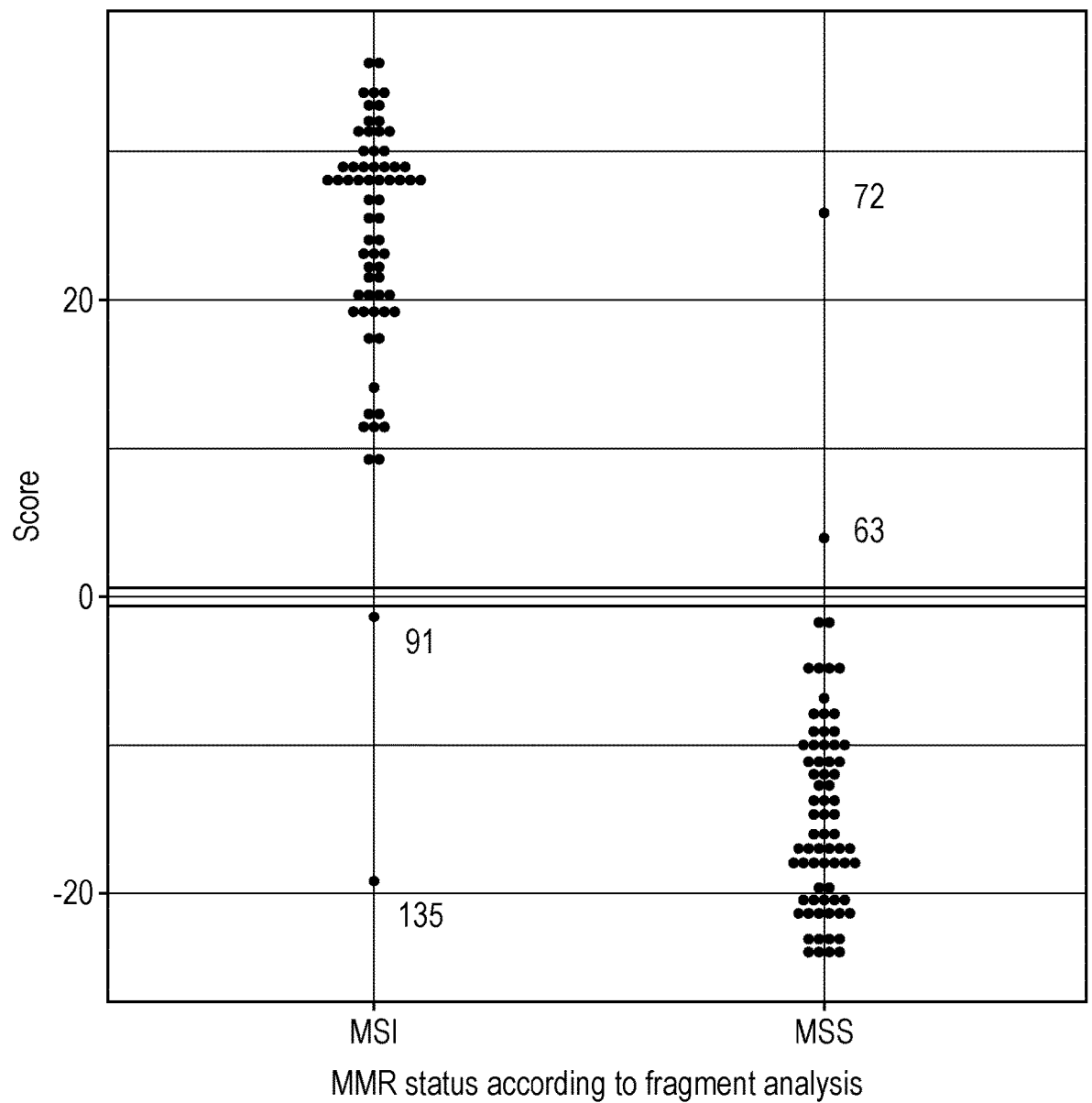
FIG. 7 shows classification of the training set.

Finally, the data from the second dataset was used to estimate the parameters and classify the samples in the first dataset. The results are represented in FIG. 7.

Four samples gave discordant results relative to fragment analysis (samples 63, 72, 91 and 135). Immunohistochemistry for sample 63 was checked and found to be consistent with reported MSS status. However, DNA from sample 72 was reanalysed by fragment analysis and microsatellite instability was detected, while immuno-histochemical analysis of samples 91 and 135 revealed no alteration in expression for MSH2, MLH1, MSH6 and PMS2. This raises the possibility that immunohistochemistry and fragment analysis are inconsistent for these 3 samples. Overall, there was a 92% concordance between fragment analysis and immunohistochemistry, as assessed by staining for MSH2, MLH1, MSH6 and PMS2. For this analysis, the concordance between our results and fragment analysis is 97% and the estimates for sensitivity and specificity are both 97% (95% confidence intervals: 89%-99% and 90%-99% respectively) when results from fragment analysis are used as reference. Interestingly, reclassification using the first data set for both parameter estimation and for testing the classification resulted in misclassification of the same four samples. Combining both sets of results led to a sensitivity of 98% (95% confidence intervals: 92%-99%) and specificity of 98% (93%-99%).

The method presented here allows sequence-based discrimination between MSI and MSS tumours using a limited number of loci, without the requirement for paired germline DNA as a reference. A multi-step process was used to select a panel of MNRs involving analysis of genomic sequence data to identify the most promising markers, and two rounds of amplicon assessment. Although, this does not ensure that the optimal set of MNRs was identified, the performance of the panel is comparable to that of fragment analysis.

The inventors chose relatively short MNR for our test to diminish the probability of PCR artefacts and to reduce the likelihood of encountering germline variation affecting MNR length, a potential confounding factor in cases where no normal material is available. However, somatic instability is also lower meaning that genuine mutations will tend to affect only one allele. Therefore even allowing for PCR errors, mutant reads should concentrate on one allele. The inventors showed that this can be assessed using flanking heterozygous SNPs and can be used to improve classification. It is worth noting that even in situations where mutations have occurred in both alleles, each allele is likely to be affected in a different proportion of cells in a sample since, during clonal evolution, there will be a time interval between the occurrence of the two mutations, and this time interval is expected to be larger for shorter microsatellites.

To the inventors knowledge, this is the first method for assessing MSI that uses allelic information. Although it only uses allelic data to assess bias in the distribution of mutant reads, it can also help to distinguish between somatic and germline variation, in particular in situations where no normal material is available, but the tumour is expected to contain normal tissue contamination. MNRs showing germline variants can be excluded from the analysis although it would also be possible to treat each allele separately. Allelic analysis however is only possible for MNRs heterozygous for flanking SNPs in a particular sample. In principle, it would be feasible to restrict the score calculation to such MNRs. However, such a procedure would disregard information from many of the amplicons used, and require larger marker panels, increasing assay costs.

The inventors used thresholds on the frequency of reads representing mutated MNRs because they wanted to dichotomise the data. Other approaches would be possible; however using a threshold that is above the frequency observed in the majority of the MSS samples is consistent with the approaches followed by other authors who aim to set their thresholds so that variation reflecting PCR artefacts is excluded (e.g. Salipante et al., 2014). The formalism presented here could be used without defining thresholds, but this would require specifying the whole deletion frequency distribution. Similarly the inventors used a threshold, the p-value of 0.05 in Fisher's exact test, to dichotomise allelic bias. Using the statistically significance of the bias seems natural although the precise choice of the threshold is arbitrary.

Since the inventors' test aims to detect MSI, it seems reasonable to use fragment analysis as the reference technique. However, MSI detection is usually a means for assessing MMR proficiency. It is noteworthy that in 3 out of 4 cases where there were discrepancies between the results generated by the inventors new method and the results from fragment analysis, there where also discrepancies between fragment analysis and immunohistochemistry results.

MNR Based Classification Deletion Frequency and Allelic Bias

In this example, the aim was to develop a classification procedure to separate samples into two classes: MSI and MSS, the latter includes samples classified by fragment analysis as showing low levels of instability (MSI-L). The classifier was designed to include information both on changes in MNR length, and on the distribution of the variant reads across both alleles. Since discrimination between alleles is only possible for samples heterozygous for a flanking SNP, not all samples can be assessed for biased distribution of variant reads across both alleles. However, lack of data should not favour either classification.

A naïve Bayes approach for the classification procedure was used (Gelman, 2014). The underlying idea is to compare the probabilities of belonging to one of two classes, i.e. MSI(H) or MSS, given the observations at each of the MNR markers used. In the following equations MSI(H) is further shortened to MSI.

If a set of MNRs is considered and, for a particular sample, the observed frequency of reads is represented showing deletion for each of them with O, the probability that the sample is microsatellite unstable with $p(MSI|O)$, and the probability that the sample is microsatellite stable with $p(MSS|O)$, then the ratio $$\frac{p(MSI \mid O)}{p(MSS \mid O)} = \frac{p(O \mid MSI)}{p(O \mid MSS)} \cdot \frac{p(MSI)}{p(MSS)}$$

can be used as the discrimination criterion. Here $p(MSI)$ and $p(MSS)$ designate the a priori probability of a sample being MMR deficient or proficient An observation consists of the read count data at the different MNRs; i.e. $O=(O_1, \ldots, O_N)$, where N designates the number of MNRs assessed in the essay.

Assuming that, for a given mismatch repair status, mutations at the different markers occur independently from each other then $$\frac{p(O \mid MSI)}{p(O \mid MSS)} = \prod_{i=1}^{N} \frac{p(O_i \mid MSI)}{p(O_i \mid MSS)}$$

For a microsatellite i in each individual, an observation $O_i$ is described by two values, $D_i$ and $B_i$, i.e. $O_i=(D_i, B_i)$ and $p(O_i)=p(D_i)p(B_i|D_i)$, where $D_i=1$ if the number of reads representing a deletion is above a pre-specified threshold and 0 otherwise, and $B_i=1$ if significant bias was observed and 0 otherwise. Therefore $$\frac{p(O_i \mid MSI)}{p(O_i \mid MSS)} = \frac{p(D_i, B_i \mid MSI)}{p(D_i, B_i \mid MSS)} = \frac{p(D_i \mid MSI)}{p(D_i \mid MSS)} \cdot \frac{p(B_i \mid D_i, MSI)}{p(B_i \mid D_i, MSS)}$$

In cases where the bias cannot be computed, for example when there are no heterozygous flanking polymorphic sites, we set $(O_i|MSI)=p(D_i|MSI)$, $p(O_i|MSS)=p(D_i|MSS)$ and the factor $$\frac{p(B_i \mid D, MSI)}{p(B_i \mid D, MSS)}$$

can be omitted.

A threshold for each microsatellite was chosen, such that 95% of all MSS samples have frequencies below the threshold. To estimate $p(D_i|MSS)$ and $p(D_i|MSI)$, the exact numbers of MSS and MSI samples with frequencies above the threshold were used.

To estimate $p(B_i|D_i, MSI)$ and $p(B_i|D_i, MSS)$, samples heterozygous at a flanking SNP marker, and for which the frequency of reads with deletions exceeded the MNR specific thresholds, were used. Bias was considered to be present when the association between the presence of a deletion and the genotype at the flanking SNP was significant at the 0.05 level using Fishers' exact test. If there were multiple heterozygous SNPs neighbouring a repeat then the SNP with the lowest p-value was used. When the deletion frequency was below the threshold, $p(B_i|D_i, MSI)$ and $p(B_i|D_i, MSS)$ were set to 1. This is equivalent to assuming that in such cases there is insufficient evidence for an MNR mutation and therefore bias is not meaningful.

The results are presented as a score $$S = \log_{10} \frac{P(MSI \mid O)}{P(MSS \mid O)}.$$

Here a set of samples was used to determine, for each MNR, the following parameters used in the classification: a) A threshold for the frequency of reads showing a deletion (for the choice of thresholds see previous paragraph and discussion above for an illustration); b) The proportion of MSI samples with a deletion frequency above this threshold; c) The proportion of MSS samples with a deletion frequency above the threshold, d) The proportion of MSI samples showing a deletion and significant allelic imbalance and e) The proportion of MSS samples showing a deletion and significant allelic imbalance. The frequencies of MSS and MSI tumours were assumed to be 0.85 and 0.15 respectively (Boland and Goel, 2010), i.e. $p(MSS)=0.85$ and $p(MSI)=0.15$.

These parameters were then used to calculate the score for each tumour in a second, independent set of samples. Samples with a score below 0 were classified as MSS and those above as MSI.

Example 4

To establish whether the amplification reaction can be multiplexed, molecular inversion probes (MIP) were designed for 15 markers (see table 11) and used to analyse 96 samples. After ligation and amplification (following the protocol published by Hiatt et al. 2013), the products were sequenced.

The table summarises the number of reads mapping to each of the markers across the 94 individuals.

TABLE 11 molecular inversion probes (MIP) designed for 15 markers

| Marker | MIP Sequence | Number of reads Median | Range |
|---|---|---|---|
| AP0035322 | GCACATTATGTTGTAGTCAAGCTTCAGCTTCCCGATA TCCGACGGTAGTGTNNNNNNNGTTTATTGGCCATTTG TATATATT (SEQ ID NO: 323) | 509 | 23-1739 |
| DEPDC2 | GTCTTTGACTCACCTGTGTAGTGTCTGCACTTCAGCT TCCCGATATCCGACGGTAGTGTNNNNNNATGTTCAC ACACATGC (SEQ ID NO: 324) | 2000 | 68-4899 |
| GM07 | CCAAACCCCATATGTGTGGTTGCCTTCAGCTTCCCGA TATCCGACGGTAGTGTNNNNNNTGGGCCCTTTTAGG CATATAG (SEQ ID NO: 325) | 3944 | 116-8831 |
| GM09 | GCATAAGGCTAGGATCATTTCATTCAAGACTTCAGCT TCCCGATATCCGACGGTAGTGTNNNNNNNCACAAAAA TCAATGCT (SEQ ID NO: 326) | 1788 | 31-6173 |
| GM11 | GAATACTTAGATACGTAGGTGATACTGAACTTCAGCT TCCCGATATCCGACGGTAGTGTNNNNNNCAAAAAAG TACAGTGG (SEQ ID NO: 327) | 2589 | 70-6775 |
| GM17 | GCAAGGGCCTGCATTGTGGTAAGTTTGTCTTCAGCTT CCCGATATCCGACGGTAGTGTNNNNNNGCTATAAAT ATCCAGTG (SEQ ID NO: 328) | 4183 | 138-11160 |
| IM16 | TTTTGAAGATGCTTGCATAGCTATCTACCTTCAGCTT CCCGATATCCGACGGTAGTGTNNNNNNGCTGAGTAA TATATGGG (SEQ ID NO: 329) | 3634 | 105-9427 |
| IM49 | GCACGCCTGTAATCCCAAGCTTCAGCTTCCCGATATC CGACGGTAGTGTNNNNNNGGATCGCTTCAGGCCAGG AGTTCAA (SEQ ID NO: 330) | 703.5 | 21-1869 |
| LR11 | CCTCACATTTTATAAAGACTTTCAACAATCTTCAGCT TCCCGATATCCGACGGTAGTGTNNNNNNCATTTCCT GTGCCTTT (SEQ ID NO: 331) | 2126 | 35-5978 |
| LR20 | GCAACTATTCAATTACAGTATATAGGGGCCTTCAGCT TCCCGATATCCGACGGTAGTGTNNNNNNTATCATGA AATTCTAT (SEQ ID NO: 332) | 990 | 32-2820 |
| LR24 | GTGGGAAAAATACTTATTCCAGGGAGAGCTTCAGCTT CCCGATATCCGACGGTAGTGTNNNNNNTTTTAAAGG GGAAAGGA (SEQ ID NO: 333) | 644 | 16-2099 |
| LR36 | AGAGTGCAAAGATAAATGTGCCTTCAGCTTCCCGATA TCCGACGGTAGTGTNNNNNNAGTGGCTGGCACTTGT GGT (SEQ ID NO: 334) | 3622 | 130-8400 |
| LR44 | CACTTTTGTTCCTTGACTGTTTTTACTCTTCAGCTT CCCGATATCCGACGGTAGTGTNNNNNNCTGAGGTAG GCTCATTT (SEQ ID NO: 335) | 882 | 18-2176 |
| LR48 | GCCCAATTATTTCAACCAGTTTCCACTGACTTCAGCT TCCCGATATCCGACGGTAGTGTNNNNNNAGAAGATT CACTCAAA (SEQ ID NO: 336) | 6690 | 199-15980 |
| LR49 | GGAGAAATGTCTGAGGCTGAATTTGGCTTCAGCTTCC CGATATCCGACGGTAGTGTNNNNNNTGGCTGCCTTT TTAGGAGG (SEQ ID NO: 337) | 3100 | 82-6649 |

These results indicate that that the amplification reaction can be multiplexed, i.e. a single reaction per patient would be sufficient.

General Materials and Methods:

Samples:

Unless stated otherwise, tumour and tissue samples were obtained from the Pathology department and Northern Genetics Service, Newcastle Hospitals NHS Foundation Trust after ethical review (REC reference 13/LO/1514). Lynch Syndrome tumours tissue and matched normal tissue from patients enrolled in the CAPP2 study were obtained after ethical review (REC reference MREC/98/3/24). The MSI status of all tumours had previously been established using the MSI Analysis System, Version 1.2 (Promega, Southampton, UK). All samples were received as either FFPE tissue or as DNA extracted from FFPE tissue.

One hundred and thirty two tumour and tissue samples were obtained, either as formalin fixed paraffin embedded (FFPE) tissues or as DNA extracted from FFPE tissues, from the Northern Genetics Service, Newcastle Hospitals NHS Foundation Trust after ethical review (REC reference 13/LO/1514). The MSI status of all tumours had previously been established using the MSI Analysis System, Version 1.2 (Promega, Southampton, UK).

A second set of 141 samples was obtained as extracted DNA from the Genetics Service of the Complejo Hospitalario de Navarra and the Oncogenetics and Hereditary Cancer Group, IDISNA (Biomedical Research Institute of Navarra, Spain). These samples were used to identify classification parameters. They had previously been MSI tested using the MSI Analysis System, Version 1.2 (Promega, Southampton, UK). Immunohistochemical analysis expression was performed using (BD biomedical Tech, New Jersey, USA) antibodies for MLH1 at 1:10; MSH6 at 1:120; and PMS2 at 1:100, and (Oncogene Ltd Middlesex, UK) antibody for MSH2 at 1:100 as ethically approved by the correspondent Medical Research and Ethics Committee (CEIC Navarra Government), and data were available for 124 of the samples.

A third set of 70 anonymised colorectal tumour DNA samples was obtained from the Department of Molecular Pathology, University of Edinburgh. Mismatch repair status had been tested for clinical service use using the Promega system.

In silico selection of MNRs: Whole genome sequences consisting of MSI colorectal cancers, matched normals, and MSS stable cancers were obtained from The Cancer Genome Atlas (TCGA) project (Cancer Genome Atlas Network, 2012), http://cancergenome.nih.gov/; access identifier: phs000178.v8.p7 DAR: 17798, request date 2012-11-13; Study accession phs000544.v1.p6; parent study: phs000178.v7.p6; 35 samples). BAM files were converted to fastq files using bam2fastq (version 1.1.0) (bam2fastq software [http://gsl.hudsonalpha.org/information/software/bam2fastq]). Sequence alignment was performed using BWA (version 0.6.2)(Li and Durbin, 2009), indexing and sorting of BAM files was done using samtools (version 0.1.18)(Li et al., 2009), duplicates were removed using PICARD (version 1.75, [http://picard.sourceforge.net]). GATK (version 2.2.9)(DePristo et al., 2011) was used to produce a combined BAM file for all samples and to realign around indels. The GATK (version 2.2.9) UnifiedGenotyper was used to produce a raw variant call file which was annotated using the TandemRepeatAnnotator for indel identification in mononucleotide repeats. Mononucleotide repeats of lengths 7 bp-12 bp were selected, and repeats encompassing common sequence variants (dbSNP version 173, hg19) (Sherry et al., 2001) removed. SNPs listed in dbSNP within 30 bp of the repeats were annotated using Perl scripts. Because of the low pass nature of the sequence data, all reads from MSI tumours were combined in one group, while reads from MSS and MSI-L tumours and from normal samples were combined in a second group as controls.

MNR amplification: Primers were designed using Primer3 (Rozen et al., 2000) or manually if Primer3 returned no suitable oligonucleotides. Primers designed manually had a Tm of 57° C.-60° C. All primers were checked for common SNPs using SNP Check (https://ngrl.manchester.ac.uk/SNPCheckV2/snpcheck.htm), off target binding using BLAST (http://blast.ncbi.nlm.nih.gov/Blast.cgi) or BLAT (Kent, 2002), and appropriate melting temperatures and absence of secondary structures using OligoCalc (http://www.basic.northwestern.edu/biotools/oligocalc.html) or Primer3. The primers were produced either by Metabion (Metabion International AG, Steinkirchen, Germany) or by Biobasic (Bio Basic Inc., Markham, Canada). Primers for all MNRs were initially designed to create amplicon of ~300-350 bp.

For the final MNR panel, a second set of primers was designed to generate 100-150 bp amplicons with 5' adapters (primer sequences are shown in Table 8a nad 8b). Amplicons were generated using the high fidelity Pfu-based Herculase II Fusion DNA polymerase (Agilent, Santa Clara, Calif., USA) and 35 PCR cycles.

Sequencing: Amplicons were quantified using Qiagen QIAxcel (Qiagen, Manchester UK.), then pooled at roughly equimolar concentrations. Agencourt AMPure XP beads (Beckman-Coulter Life Sciences, Indianapolis, USA) were used for PCR clean up before Library Preparation. For the 300-350 bp amplicons, barcoding and library preparation were performed using the Nextera XT DNA Library Prep kit (Illumina, San Diego, Calif., United States of America), after pooling of the amplification products for each sample, while for the 100-150 bp amplicons the 16S metagenomic sample preparation protocol was followed (http://supportil-lumina.com/documents/documentation/chemistry_documentation/16s/16s-metagenomic-library-prep-guide-15044223-b.pdf). Sequencing was performed on the Illumina MiSeq plattform to a target depth of at least 10,000 reads per amplicon.

Variant and MNR calling: Sequences were aligned using BWA (version 0.6.2) and the hg19 assembly as reference. Samtools was used to sort and index the BAM files, and realignment was done using GATK (3.1.1). Alignment files were converted to SAM format and processed using R scripts. Only features observed on both reads of a pair, i.e. concordant in both orientations, were used in subsequent calculations and only amplicons where the MNR was covered by at least 20 read pairs were analysed. Flanking SNPs were considered to be heterozygous if the least common allele, i.e. the allele supported by the smallest number of reads, was present in at least 20% all the read pairs covering the SNP position.

Construction of MNR specific ROC curves: For each marker, the proportion of reads representing MNR deletion alleles in MSI and MSS samples was analysed separately. A threshold approach to MSI classification was used: samples with a proportion of variant reads above the threshold being classified as MSI, below as MSS. This enabled the relative frequency of true positives (i.e. known MSI samples with a value above the threshold), and of false positives (i.e. known MSS samples with a value above the threshold) to be determined. For each MNR, these two values were then plotted against each other for thresholds between 0 and 1. The resulting curve represents the receiver operating characteristic (ROC) curve and the area under the curve (AUC) was used as a quantitative measure of the ability of the MNR to discriminate between MSI and MSS samples.

It will be understood by those within the art that, in general, terms used herein, and especially in the appended claims are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

It will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

REFERENCES

Burn, J., Gerdes, A. M., Macrae, F., Mecklin, J. P., Moeslein, G., Olschwang, S., Eccles, D., Evans, D. G., Maher, E. R., Bertario, L., Bisgaard, M. L., Dunlop, M. G., Ho, J. W., Hodgson, S. V., Lindblom, A., Lubinski, J., Morrison, P. J., Murday, V., Ramesar, R., Side, L., Scott, R. J., Thomas, H. J., Vasen, H. F., Barker, G., Crawford, G., Elliott, F., Movahedi, M., Pylvanainen, K., Wijnen, J. T., Fodde, R., Lynch, H. T., Mathers, J. C. and Bishop, D. T. 2011. Long-term effect of aspirin on cancer risk in carriers of hereditary colorectal cancer: an analysis from the CAPP2 randomised controlled trial. Lancet, 378, 2081-7.

Cancer Genome Atlas Network. (2012). Comprehensive molecular characterization of human colon and rectal cancer. Nature 487, 330-337.

Li, H. 2014. Toward better understanding of artifacts in variant calling from highcoverage samples. Bioinformatics, 30, 2843-51.

O'Rawe, J., Jiang, T., Sun, G., Wu, Y., Wang, W., Hu, J., Bodily, P., Tian, L., Hakonarson, H., Johnson, W. E., Wei, Z., Wang, K. and Lyon, G. J. 2013. Low concordance of multiple variant-calling pipelines: practical implications for exome and genome sequencing. Genome Med, 5, 28.

Pabinger, S., Dander, A., Fischer, M., Snajder, R., Sperk, M., Efremova, M., Krabichler, B., Speicher, M. R., Zscocke, J. and Trajanoski, Z. 2014. A survey of tools for variant analysis of next-generation genome sequencing data. Brief Bioinform, 15, 256-78.

Houniet, D. T., Rahman, T. J., A L Turki, S., Hurles, M. E., Xu, Y., Goodship, J., Keavney, B. and Santibanez Koref, M. 2015. Using population data for assessing next-generation sequencing performance. Bioinformatics, 31, 56-61.

Minoche, A. E., Dohm, J. C. and Himmelbauer, H. 2011. Evaluation of genomic high-throughput sequencing data generated on Illumina HiSeq and genome analyzer systems. Genome Biol, 12, R112.

Sambrook et al., Molecular Cloning: A Laboratory Manual, 2nd ed., Cold Spring Harbor Press, Plainsview, N.Y. (1989)

Ausubel et al., Current Protocols in Molecular Biology (Supplement 47), John Wiley & Sons, New York (1999)

Sainsbury, Dictionary of Microbiology and Molecular Biology, 2d Ed., John Wiley and Sons, NY (1994)

Hale and Marham, The Harper Collins Dictionary of Biology, Harper Perennial, NY (1991)

de la Chapelle, A., and Hampel, H. (2010). Clinical relevance of microsatellite instability in colorectal cancer. Journal of Clinical Oncology 28, 3380-3387.

Laiho, P., Launonen, V., Lahermo, P., Esteller, M., Guo, M., Herman, J. G., Mecklin, J. P., Jarvinen, H., Sistonen, P., Kim, K. M., et al. (2002). Low-level microsatellite Boyle, T. A., Bridge, J. A., Sabatini, L. M., Nowak, J. A., Vasalos, P., Jennings, L. J., and Halling, K. C. (2014). Summary of microsatellite instability test results from laboratories participating in proficiency surveys: proficiency survey results from 2005 to 2012. Arch Pathol Lab Med 138, 363-370.

Shinde, D., Lai, Y., Sun, F., and Arnheim, N. (2003). Taq DNA polymerase slippage mutation rates measured by PCR and quasi-likelihood analysis:(CA/GT) n and (A/T) n microsatellites. Nucleic acids research 31, 974-980.

Umar, A., Boland, C. R., Terdiman, J. P., Syngal, S., de la Chapelle, A., Ruschoff, J., Fishel, R., Lindor, N. M., Burgart, L. J., Hamelin, R., et al. (2004). Revised Bethesda Guidelines for hereditary nonpolyposis colorectal cancer (Lynch syndrome) and microsatellite instability. Journal of the National Cancer Institute 96, 261-268.

Shia, J. (2008). Immunohistochemistry versus microsatellite instability testing for screening colorectal cancer patients at risk for hereditary nonpolyposis colorectal cancer syndrome. Part I. The utility of immunohistochemistry. The Journal of molecular diagnostics: JMD 10, 293-300.

Zhang, L. (2008). Immunohistochemistry versus microsatellite instability testing for screening colorectal cancer patients at risk for hereditary nonpolyposis colorectal cancer syndrome. Part II. The utility of microsatellite instability testing. The Journal of molecular diagnostics: JMD 10, 301-307.

Niu, B., Ye, K., Zhang, Q., Lu, C., Xie, M., McLellan, M. D., Wendl, M. C., and Ding, L. (2014). MSIsensor: microsatellite instability detection using paired tumor-normal sequence data. Bioinformatics 30, 1015-1016.

Lu, Y., Soong, T. D., and Elemento, O. (2013). A novel approach for characterizing microsatellite instability in cancer cells. PLoS One 8, e63056.

Salipante, S. J., Scroggins, S. M., Hampel, H. L., Turner, E. H., and Pritchard, C. C. (2014). Microsatellite instability detection by next generation sequencing. Clin Chem 60, 1192-1199.

Ananda, G., Walsh, E., Jacob, K. D., Krasilnikova, M., Eckert, K. A., Chiaromonte, F., and Makova, K. D. (2013). Distinct mutational behaviors differentiate short tandem repeats from microsatellites in the human genome. Genome Biol Evol 5, 606-620.

Snowsill, T., Huxley, N., Hoyle, M., Jones-Hughes, T., Coelho, H., Cooper, C., Frayling, I., and Hyde, C. (2014). A systematic review and economic evaluation of diagnostic strategies for Lynch syndrome. Health Technol Assess 18, 1-406. NICE. (2017). Molecular testing strategies for Lynch syndrome in people with colorectal cancer. [https://www.nice.org.uk/guidance/dg27] (accessed 10/04/2017)

Yoon, K., Lee, S., Han, T. S., Moon, S. Y., Yun, S. M., Kong, S. H., Jho, S., Choe, J., Yu, J., Lee, H. J., Park, J. H., Kim, H. M., Lee, S. Y., Park, J., Kim, W. H., Bhak, J., Yang, H. K. and Kim, S. J. 2013. Comprehensive genome- and transcriptome-wide analyses of mutations associated with microsatellite instability in Korean gastric cancers. Genome Res, 23, 1109-17.

Kent, W. J., Sugnet, C. W., Furey, T. S., Roskin, K. M., Pringle, T. H., Zahler, A. M. & Haussler, D. 2002. The human genome browser at UCSC. Genome Res, 12, 996-1006.

Rozen, S. and Skaletsky, H. 2000. Primer3 on the WWW for general users and for biologist programmers. Methods Mol Biol, 132, 365-86.

Alhopuro, P., Phichith, D., Tuupanen, S., Sammalkorpi, H., Nybondas, M., Saharinen, J., Robinson, J. P., Yang, Z., Chen, L. Q., Orntoft, T., et al. (2008). Unregulated smooth-muscle myosin in human intestinal neoplasia. Proceedings of the National Academy of Sciences of the United States of America 105, 5513-5518.

Sammalkorpi, H., Alhopuro, P., Lehtonen, R., Tuimala, J., Mecklin, J. P., Jarvinen, H. J., Jiricny, J., Karhu, A., and Aaltonen, L. A. (2007). Background mutation frequency in microsatellite-unstable colorectal cancer. Cancer Res 67, 5691-5698.

Gelman, A. (2014). Bayesian data analysis.(Boca Raton: CRC Press).

Boland, C. R., and Goel, A. (2010). Microsatellite instability in colorectal cancer. Gastroenterology 138, 2073-2087 e2073.

Hiatt et al. 2013 Genome Research 23(5):843-54. (http://genome.cshlp.org/content/23/5/843.long)

Kent, W. J. (2002). BLAT—the BLAST-like alignment tool. Genome Res 12, 656-664.

bam2fastq software [http://gsl.hudsonalpha.org/information/software/bam2fastq].

Li, H., and Durbin, R. (2009). Fast and accurate short read alignment with Burrows-Wheeler transform. Bioinformatics 25, 1754-1760.

Li, H., Handsaker, B., Wysoker, A., Fennell, T., Ruan, J., Homer, N., Marth, G., Abecasis, G., and Durbin, R. (2009). The Sequence Alignment/Map format and SAMtools. Bioinformatics 25, 2078-2079.

PICARD [http://picard.sourceforge.net].

DePristo, M. A., Banks, E., Poplin, R., Garimella, K. V., Maguire, J. R., Hartl, C., Philippakis, A. A., del Angel, G., Rivas, M. A., Hanna, M., et al. (2011). A framework for variation discovery and genotyping using next-generation DNA sequencing data. Nature genetics 43, 491-498.

Sherry, S. T., Ward, M. H., Kholodov, M., Baker, J., Phan, L., Smigielski, E. M., and Sirotkin, K. (2001). dbSNP: the NCBI database of genetic variation. Nucleic acids research 29, 308-311.

The invention claimed is:

1. A method for determining levels of microsatellite instability in a tumor sample, wherein the method comprises the steps of:
   (a) providing primers for amplifying a plurality of a selected group of at least 15 microsatellite loci of human genomic DNA selected from the group consisting of LR49, IM66, LR20, GM11, LR24, IM16, GM17, GM09, GM07, LR36, LR44, LR48, LR11, AP003532_2, DEPDC2, GM14, and IM49;
   (b) amplifying from the sample the plurality of selected microsatellite mono-nucleotide repeat loci to give microsatellite amplicons;
   (c) sequencing the microsatellite amplicons; and
   (d) comparing the sequences from the microsatellite amplicons to predetermined sequences and determining any deviation, indicative of instability, from the predetermined sequences, thereby determining the level of microsatellite instability in the sample.

2. The method of claim 1, wherein, in step (a) primers are provided for amplifying at least 17 of the selected group of microsatellite loci of human genomic DNA.

3. A method for determining levels of microsatellite instability in a tumor sample, wherein the method comprises the steps of:
   (a) providing primers for amplifying each of the microsatellite loci of human genomic DNA provided in the group consisting of LR49, IM66, LR20, GM11, LR24, IM16, GM17, GM9, GM07, LR36, LR44, LR48, LR11, AP003532_2, DEPDC2, GM14, and IM49;
   (b) amplifying from the sample the plurality of microsatellite mono-nucleotide repeat loci to give microsatellite amplicons;
   (c) sequencing the microsatellite amplicons; and
   (d) comparing the sequences from the microsatellite amplicons to predetermined sequences and determining any deviation, indicative of instability, from the predetermined sequences, thereby determining the level of microsatellite instability in the sample.

4. The method of claim 1, wherein the primers co-amplify the selected microsatellite loci.

5. The method of claim 1, wherein the amplifying from the sample the plurality of selected microsatellite mono-nucleotide repeat loci to give microsatellite amplicons comprises co-amplifying the set of selected loci in a multiplex amplification reaction.

6. The method of claim 1, wherein primer pairs comprising the primers are capable of being used in a multiplex amplification reaction.

7. The method of claim 1, wherein a number of separate microsatellite mono-nucleotide repeat loci are amplified and sequenced as separate reactions.

8. The method of claim 1, wherein the sequencing step of (c) uses high throughput or next generation sequencing.

9. The method of claim 1, wherein the sequencing step of (c) uses sequencing-by-synthesis.

10. The method of claim 1, wherein the sequencing step of (c) uses ion semiconductor sequencing, pyrosequencing, or ion torrent sequencing.

11. The method of claim 1, wherein amplification is by polymerase chain reaction and uses primer pairs comprising the primers, wherein each primer pair comprises a forward primer which is complementary to a portion upstream from a selected microsatellite mono-nucleotide repeat loci, and a reverse primer which is complimentary to a portion downstream from said selected microsatellite mono-nucleotide repeat loci.

12. The method of claim 1, wherein the selected group of microsatellite loci comprises a single nucleotide polymorphism (SNP) within a short distance of the microsatellite loci.

13. The method of claim 1, wherein the selected group of microsatellite loci comprises a single nucleotide polymorphism (SNP) within 100 base pairs of the microsatellite loci.

* * * * *

SEQUENCE LISTING

<160> NUMBER OF SEQ ID NOS: 337

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
tgcatgcaag acaggagcc                                               19

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
ggagaaacaa acttaccttg ggaa                                         24

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
ctttagaact ggatccagtg g                                            21

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
aaaaagtgga gtggaggagg                                              20

<210> SEQ ID NO 5

```
<211> LENGTH: 21
<212> TYPE: DNA
<213> ORGANISM: Artificial Sequence
<220> FEATURE:
<223> OTHER INFORMATION: Primer

<400> SEQUENCE: 5
aacccagttt ctttccttct g                                              21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gcctcaacct aggacccttc                                                20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
tcaccactgg ggactttttc                                                20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
tgagcacacc aagtcattct g                                              21

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tagaggcagc aggctctcag                                                20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
accccacaaa ccatgaaatc                                                20

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
```
cacagcccat tcctggac                                                     18

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
gccattgctt acatctcatg g                                                 21

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
aggactctgg cacctacgtc                                                   20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tcgcaaggaa actacagcag                                                   20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tctgggaaaa agcccataac                                                   20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
acaacaccct ctcacccaac                                                   20

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
tgactatgac aggagcttaa aactg                                             25

<210> SEQ ID NO 18
<211> LENGTH: 23
<212> TYPE: DNA

```
<213> ORGANISM: Artificial Sequence
<220> FEATURE:
<223> OTHER INFORMATION: Primer

<400> SEQUENCE: 18
cccacaccac attgtatgta gac                                          23

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ggcacaccag gagaaagagg                                              20

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
gccccgacct accatacag                                               19

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21 cgttttgtg gaagcatacg                                               20

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ccaaatggca aataaagaa gg                                            22

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
catgatatgc ccatgtaggg                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
attggtgaag gaaccagcag                                              20
```

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cagctgaaac cgaagtgaag                                              20

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ttgatgatcc ttttgacacc ac                                           22

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
ccctttacac cacatcaatg c                                            21

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
gcagggccca tcatacag                                                18

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
ttcccaactg taagaacaag agag                                         24

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
cacttcagag tgatgttgtc ttca                                         24

<210> SEQ ID NO 31
<211> LENGTH: 22
<212> TYPE: DNA
<213> ORGANISM: Artificial Sequence
<220> FEATURE:

<223> OTHER INFORMATION: Primer

<400> SEQUENCE: 31
tcttccttat gacaacccac ac                                               22

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gagcaccttc cgactcactc                                                  20

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
tgccaatatt tcaatttttc tcc                                              23

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
agactatgcc ttgcccagag                                                  20

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
tccaatagga aactgagagc tattc                                            25

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
tggagcagag caatagagag g                                                21

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
ctgcagagcc acccattc                                                    18

```
<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
agatgaacca agccagaagc                                                   20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
tggaggcctc actatgttcc                                                   20

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
ctggtgcacg gactatgc                                                     18

<210> SEQ ID NO 41
<211> LENGTH: 18
<212> TYPE: DNA
<213> ORGANISM: Artificial Sequence
<220> FEATURE:
<223> OTHER INFORMATION: Primer

<400> SEQUENCE: 41
gtggggacag acccagtg                                                     18

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
gggcaagagg cctaacagtg                                                   20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
cacagactgg ttttgcaacg                                                   20

<210> SEQ ID NO 44
<211> LENGTH: 20
<212> TYPE: DNA
<213> ORGANISM: Artificial Sequence
<220> FEATURE:
<223> OTHER INFORMATION: Primer
```

```
<400> SEQUENCE: 44
cttgtgctcc ttgctcacag                                              20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
ctccagcgag aaagaattgg                                              20

<210> SEQ ID NO 46
<211> LENGTH: 19
<212> TYPE: DNA
<213> ORGANISM: Artificial Sequence
<220> FEATURE:
<223> OTHER INFORMATION: Primer

<400> SEQUENCE: 46
attgatccct caccggaac                                               19

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
tttgttatat cccattaggt gcc                                          23

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
atcacgaggt tgagatcgag                                              20

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
tcaaggccag gcaattaatc ag                                           22

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
acttgctgaa tgtccaaggt g                                            21

<210> SEQ ID NO 51
<211> LENGTH: 22
```

-continued

<212> TYPE: DNA
<213> ORGANISM: Artificial Sequence
<220> FEATURE:
<223> OTHER INFORMATION: Primer

<400> SEQUENCE: 51
gtgctacatg agatagctgg ga                                    22

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
ctcttctggc cagttctatg tgt                                   23

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
tggagtaaga ccctttaggc ag                                    22

<210> SEQ ID NO 54
<211> LENGTH: 21
<212> TYPE: DNA
<213> ORGANISM: Artificial Sequence
<220> FEATURE:
<223> OTHER INFORMATION: Primer

<400> SEQUENCE: 54
agactctgga agcaaatggc a                                     21

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55 cctttggcc agaatatgcc                                        20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
ggcatgagga agtgaaggga                                       20

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
aggtgtcaag caaggactca g    21

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
aggcgttttc acgttggagg    20

<210> SEQ ID NO 59
<211> LENGTH: 22
<212> TYPE: DNA
<213> ORGANISM: Artificial Sequence
<220> FEATURE:
<223> OTHER INFORMATION: Primer

<400> SEQUENCE: 59
agaggcagaa tgtggaaaag tc    22

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
gcattctccc acagcacaat    20

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
ggagggacat gtgtttccaa at    22

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
cacaatgagc caagtctcac a    21

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
agcaacctct taaatccagt act    23

<210> SEQ ID NO 64
<211> LENGTH: 20
<212> TYPE: DNA
<213> ORGANISM: Artificial Sequence

```
<220> FEATURE:
<223> OTHER INFORMATION: Primer

<400> SEQUENCE: 64
tgggctttct tgactttgga                                                    20

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
tttctcagga caaagagcaa ggt                                                23

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
ctgggttcca tcttgtgggg                                                    20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
atcagctgac tccttaccct                                                    20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
tggggtgaga gatggacatg                                                    20

<210> SEQ ID NO 69
<211> LENGTH: 25
<212> TYPE: DNA
<213> ORGANISM: Artificial Sequence
<220> FEATURE:
<223> OTHER INFORMATION: Primer

<400> SEQUENCE: 69
ctcatggtta atacaattag gcaca                                              25

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
acatggtgtg ctacctttca                                                    20
```

```
<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
ttcttcaggg cccattattg t                                                 21

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
tgaggaatgt gcagttgaca c                                                 21

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
agcttggcca tatttgtgca                                                   20

<210> SEQ ID NO 74
<211> LENGTH: 23
<212> TYPE: DNA
<213> ORGANISM: Artificial Sequence
<220> FEATURE:
<223> OTHER INFORMATION: Primer

<400> SEQUENCE: 74
acttgatagg gttaaatgtc cgt                                               23

<210> SEQ ID NO 75
<211> LENGTH: 21
<212> TYPE: DNA
<213> ORGANISM: Artificial Sequence
<220> FEATURE:
<223> OTHER INFORMATION: Primer

<400> SEQUENCE: 75
tgccttcgag tttaaatgcc t                                                 21

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
gcctcgttat tttgtgtgcc                                                   20

<210> SEQ ID NO 77
<211> LENGTH: 21
<212> TYPE: DNA
<213> ORGANISM: Artificial Sequence
<220> FEATURE:
<223> OTHER INFORMATION: Primer
```

<400> SEQUENCE: 77
gccacactga ctttgaacct t                                    21

<210> SEQ ID NO 78
<211> LENGTH: 22
<212> TYPE: DNA
<213> ORGANISM: Artificial Sequence
<220> FEATURE:
<223> OTHER INFORMATION: Primer

<400> SEQUENCE: 78
acagcttctt cctcactcta ct                                   22

<210> SEQ ID NO 79
<211> LENGTH: 23
<212> TYPE: DNA
<213> ORGANISM: Artificial Sequence
<220> FEATURE:
<223> OTHER INFORMATION: Primer

<400> SEQUENCE: 79
tccctagaaa gagaacgaca aca                                  23

<210> SEQ ID NO 80
<211> LENGTH: 23
<212> TYPE: DNA
<213> ORGANISM: Artificial Sequence
<220> FEATURE:
<223> OTHER INFORMATION: Primer

<400> SEQUENCE: 80
aaatgcccac caagattgta aaa                                  23

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
ggggagaaga cggttgaact                                      20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
actggttcac tggccttttg                                      20

<210> SEQ ID NO 83
<211> LENGTH: 23
<212> TYPE: DNA
<213> ORGANISM: Artificial Sequence
<220> FEATURE:
<223> OTHER INFORMATION: Primer

<400> SEQUENCE: 83
aggtaaagtc agacacaatc cca                                  23

<210> SEQ ID NO 84

```
<211> LENGTH: 21
<212> TYPE: DNA
<213> ORGANISM: Artificial Sequence
<220> FEATURE:
<223> OTHER INFORMATION: Primer

<400> SEQUENCE: 84
accctcatgt ttcccacctc a                                              21

<210> SEQ ID NO 85
<211> LENGTH: 23
<212> TYPE: DNA
<213> ORGANISM: Artificial Sequence
<220> FEATURE:
<223> OTHER INFORMATION: Primer

<400> SEQUENCE: 85
gcaatcacat ttgcattggt ttt                                            23

<210> SEQ ID NO 86
<211> LENGTH: 23
<212> TYPE: DNA
<213> ORGANISM: Artificial Sequence
<220> FEATURE:
<223> OTHER INFORMATION: Primer

<400> SEQUENCE: 86
tgactatgag ctccacaaac gta                                            23

<210> SEQ ID NO 87
<211> LENGTH: 23
<212> TYPE: DNA
<213> ORGANISM: Artificial Sequence
<220> FEATURE:
<223> OTHER INFORMATION: Primer

<400> SEQUENCE: 87
ttctccattg gaagtatttg gga                                            23

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
tgtgtattca gggtccaggg                                                20

<210> SEQ ID NO 89
<211> LENGTH: 21
<212> TYPE: DNA
<213> ORGANISM: Artificial Sequence
<220> FEATURE:
<223> OTHER INFORMATION: Primer

<400> SEQUENCE: 89
tcataaccaa gagcaccacc t                                              21

<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
```

```
tgtgataggg aaacacacgg a                                              21

<210> SEQ ID NO 91
<211> LENGTH: 22
<212> TYPE: DNA
<213> ORGANISM: Artificial Sequence
<220> FEATURE:
<223> OTHER INFORMATION: Primer

<400> SEQUENCE: 91
cagcataaat ccaatggcta tg                                             22

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
tcagattgca aagggtaca                                                 20

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
aaacatttcg actggtgcaa                                                20

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
ttcttctttc ccccaaatga                                                20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
tgggattagg gaagggagag                                                20

<210> SEQ ID NO 96
<211> LENGTH: 19
<212> TYPE: DNA
<213> ORGANISM: Artificial Sequence
<220> FEATURE:
<223> OTHER INFORMATION: Primer

<400> SEQUENCE: 96
ggccctcccc aactaaaat                                                 19

<210> SEQ ID NO 97
<211> LENGTH: 20
<212> TYPE: DNA
```

<213> ORGANISM: Artificial Sequence
<220> FEATURE:
<223> OTHER INFORMATION: Primer

<400> SEQUENCE: 97
ccttcctttg atccgcaagc                                               20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
ctgccaccta ggaactggag                                               20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
tttttgttgc ccatttcctc                                               20

<210> SEQ ID NO 100
<211> LENGTH: 21
<212> TYPE: DNA
<213> ORGANISM: Artificial Sequence
<220> FEATURE:
<223> OTHER INFORMATION: Primer

<400> SEQUENCE: 100
agggtactga ccctagctcc a                                             21

<210> SEQ ID NO 101
<211> LENGTH: 23
<212> TYPE: DNA
<213> ORGANISM: Artificial Sequence
<220> FEATURE:
<223> OTHER INFORMATION: Primer

<400> SEQUENCE: 101
ctcagacaaa gacatacgaa gcc                                           23

<210> SEQ ID NO 102
<211> LENGTH: 25
<212> TYPE: DNA
<213> ORGANISM: Artificial Sequence
<220> FEATURE:
<223> OTHER INFORMATION: Primer

<400> SEQUENCE: 102
ttggttctac agtaattgtg cttct                                         25

<210> SEQ ID NO 103
<211> LENGTH: 20
<212> TYPE: DNA
<213> ORGANISM: Artificial Sequence
<220> FEATURE:
<223> OTHER INFORMATION: Primer

<400> SEQUENCE: 103
ccctcccaaa tgtcaagtgt                                               20

<210> SEQ ID NO 104
<211> LENGTH: 20
<212> TYPE: DNA
<213> ORGANISM: Artificial Sequence
<220> FEATURE:
<223> OTHER INFORMATION: Primer

<400> SEQUENCE: 104
cccacccaca ctcttttgtt                                                    20

<210> SEQ ID NO 105
<211> LENGTH: 25
<212> TYPE: DNA
<213> ORGANISM: Artificial Sequence
<220> FEATURE:
<223> OTHER INFORMATION: Primer

<400> SEQUENCE: 105
tcaatgctat tggcctataa agagt                                              25

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
atgcatttcc ttctggccta                                                    20

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
tcaccatcat caccatgctt                                                    20

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
tctggcaaac tcttcactgg                                                    20

<210> SEQ ID NO 109
<211> LENGTH: 20
<212> TYPE: DNA
<213> ORGANISM: Artificial Sequence
<220> FEATURE:
<223> OTHER INFORMATION: Primer

<400> SEQUENCE: 109
agtggagaaa acggttgtgg                                                    20

<210> SEQ ID NO 110
<211> LENGTH: 20
<212> TYPE: DNA
<213> ORGANISM: Artificial Sequence
<220> FEATURE:

<223> OTHER INFORMATION: Primer

<400> SEQUENCE: 110
gaaggcagac aagggattca                                                   20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
gtgaccgcac aaagtcacac                                                   20

<210> SEQ ID NO 112
<211> LENGTH: 21
<212> TYPE: DNA
<213> ORGANISM: Artificial Sequence
<220> FEATURE:
<223> OTHER INFORMATION: Primer

<400> SEQUENCE: 112
tccaacaatc acagtccatg a                                                 21

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
tcaagactca gccatttcca                                                   20

<210> SEQ ID NO 114
<211> LENGTH: 21
<212> TYPE: DNA
<213> ORGANISM: Artificial Sequence
<220> FEATURE:
<223> OTHER INFORMATION: Primer

<400> SEQUENCE: 114
ggaagctgag agcaggtttt t                                                 21

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
tcgtcaggct ctgcaactac                                                   20

<210> SEQ ID NO 116
<211> LENGTH: 20
<212> TYPE: DNA
<213> ORGANISM: Artificial Sequence
<220> FEATURE:
<223> OTHER INFORMATION: Primer

<400> SEQUENCE: 116
cgatgggatt gaatttggat                                                   20

```
<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
aggacctcga gcttctcttt                                               20

<210> SEQ ID NO 118
<211> LENGTH: 20
<212> TYPE: DNA
<213> ORGANISM: Artificial Sequence
<220> FEATURE:
<223> OTHER INFORMATION: Primer

<400> SEQUENCE: 118
ttcttttgct tccgtgtgtg                                               20

<210> SEQ ID NO 119
<211> LENGTH: 21
<212> TYPE: DNA
<213> ORGANISM: Artificial Sequence
<220> FEATURE:
<223> OTHER INFORMATION: Primer

<400> SEQUENCE: 119
tgcaaccaga ggttttaatc g                                             21

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
ctcaattcag caacaggtca                                               20

<210> SEQ ID NO 121
<211> LENGTH: 20
<212> TYPE: DNA
<213> ORGANISM: Artificial Sequence
<220> FEATURE:
<223> OTHER INFORMATION: Primer

<400> SEQUENCE: 121
caaccacagt ttgccagcta                                               20

<210> SEQ ID NO 122
<211> LENGTH: 22
<212> TYPE: DNA
<213> ORGANISM: Artificial Sequence
<220> FEATURE:
<223> OTHER INFORMATION: Primer

<400> SEQUENCE: 122
tccttgctat catttggaga ga                                            22

<210> SEQ ID NO 123
<211> LENGTH: 21
<212> TYPE: DNA
<213> ORGANISM: Artificial Sequence
<220> FEATURE:
<223> OTHER INFORMATION: Primer
```

```
<400> SEQUENCE: 123
ccagtttcac atttcgcttg t                                        21

<210> SEQ ID NO 124
<211> LENGTH: 22
<212> TYPE: DNA
<213> ORGANISM: Artificial Sequence
<220> FEATURE:
<223> OTHER INFORMATION: Primer

<400> SEQUENCE: 124
tggcaacaaa acagtaacag ga                                       22

<210> SEQ ID NO 125
<211> LENGTH: 20
<212> TYPE: DNA
<213> ORGANISM: Artificial Sequence
<220> FEATURE:
<223> OTHER INFORMATION: Primer

<400> SEQUENCE: 125
agtgaatggg ctttggactg                                          20

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
aactggagtg ggtgaacctg                                          20

<210> SEQ ID NO 127
<211> LENGTH: 20
<212> TYPE: DNA
<213> ORGANISM: Artificial Sequence
<220> FEATURE:
<223> OTHER INFORMATION: Primer

<400> SEQUENCE: 127
caccagcttt tctcccttca                                          20

<210> SEQ ID NO 128
<211> LENGTH: 21
<212> TYPE: DNA
<213> ORGANISM: Artificial Sequence
<220> FEATURE:
<223> OTHER INFORMATION: Primer

<400> SEQUENCE: 128
tggcactcaa taccaaactg g                                        21

<210> SEQ ID NO 129
<211> LENGTH: 21
<212> TYPE: DNA
<213> ORGANISM: Artificial Sequence
<220> FEATURE:
<223> OTHER INFORMATION: Primer

<400> SEQUENCE: 129
ggtttctgtg ctgaatcttg g                                        21

<210> SEQ ID NO 130
<211> LENGTH: 20
```

-continued

<212> TYPE: DNA
<213> ORGANISM: Artificial Sequence
<220> FEATURE:
<223> OTHER INFORMATION: Primer

<400> SEQUENCE: 130
aaccccagtt ttctgcctct                                                    20

<210> SEQ ID NO 131
<211> LENGTH: 20
<212> TYPE: DNA
<213> ORGANISM: Artificial Sequence
<220> FEATURE:
<223> OTHER INFORMATION: Primer

<400> SEQUENCE: 131
ccatggtacc actgtggagt                                                    20

<210> SEQ ID NO 132
<211> LENGTH: 20
<212> TYPE: DNA
<213> ORGANISM: Artificial Sequence
<220> FEATURE:
<223> OTHER INFORMATION: Primer

<400> SEQUENCE: 132
tagagggggc ttgaatgttg                                                    20

<210> SEQ ID NO 133
<211> LENGTH: 20
<212> TYPE: DNA
<213> ORGANISM: Artificial Sequence
<220> FEATURE:
<223> OTHER INFORMATION: Primer

<400> SEQUENCE: 133
gggctcgact tgatttacga                                                    20

<210> SEQ ID NO 134
<211> LENGTH: 20
<212> TYPE: DNA
<213> ORGANISM: Artificial Sequence
<220> FEATURE:
<223> OTHER INFORMATION: Primer

<400> SEQUENCE: 134
gggaagcaat ctcatggcta                                                    20

<210> SEQ ID NO 135
<211> LENGTH: 20
<212> TYPE: DNA
<213> ORGANISM: Artificial Sequence
<220> FEATURE:
<223> OTHER INFORMATION: Primer

<400> SEQUENCE: 135
acgcatggaa aaagaggttc                                                    20

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136
caaggctggt atgggtcaat                                                   20

<210> SEQ ID NO 137
<211> LENGTH: 20
<212> TYPE: DNA
<213> ORGANISM: Artificial Sequence
<220> FEATURE:
<223> OTHER INFORMATION: Primer

<400> SEQUENCE: 137
tgtggaatcc ctcctgaaat                                                   20

<210> SEQ ID NO 138
<211> LENGTH: 20
<212> TYPE: DNA
<213> ORGANISM: Artificial Sequence
<220> FEATURE:
<223> OTHER INFORMATION: Primer

<400> SEQUENCE: 138
ccgctggtgg acttttactc                                                   20

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
gccaaaatgc ctaactccaa                                                   20

<210> SEQ ID NO 140
<211> LENGTH: 20
<212> TYPE: DNA
<213> ORGANISM: Artificial Sequence
<220> FEATURE:
<223> OTHER INFORMATION: Primer

<400> SEQUENCE: 140
ggactcggat ggaagacaaa                                                   20

<210> SEQ ID NO 141
<211> LENGTH: 20
<212> TYPE: DNA
<213> ORGANISM: Artificial Sequence
<220> FEATURE:
<223> OTHER INFORMATION: Primer

<400> SEQUENCE: 141
agggtatgat ttgggggtgt                                                   20

<210> SEQ ID NO 142
<211> LENGTH: 20
<212> TYPE: DNA
<213> ORGANISM: Artificial Sequence
<220> FEATURE:
<223> OTHER INFORMATION: Primer

<400> SEQUENCE: 142
gtggaccaaa ggagcagaag                                                   20

<210> SEQ ID NO 143
<211> LENGTH: 20
<212> TYPE: DNA
<213> ORGANISM: Artificial Sequence

```
<220> FEATURE:
<223> OTHER INFORMATION: Primer

<400> SEQUENCE: 143
tgagggtgga tgcttcattt                                               20

<210> SEQ ID NO 144
<211> LENGTH: 24
<212> TYPE: DNA
<213> ORGANISM: Artificial Sequence
<220> FEATURE:
<223> OTHER INFORMATION: Primer

<400> SEQUENCE: 144
caggatattc ctcagttcag ttcc                                          24

<210> SEQ ID NO 145
<211> LENGTH: 21
<212> TYPE: DNA
<213> ORGANISM: Artificial Sequence
<220> FEATURE:
<223> OTHER INFORMATION: Primer

<400> SEQUENCE: 145
tcaaatgcag actcaacatg a                                             21

<210> SEQ ID NO 146
<211> LENGTH: 20
<212> TYPE: DNA
<213> ORGANISM: Artificial Sequence
<220> FEATURE:
<223> OTHER INFORMATION: Primer

<400> SEQUENCE: 146
agcagaggag ccatcaattc                                               20

<210> SEQ ID NO 147
<211> LENGTH: 20
<212> TYPE: DNA
<213> ORGANISM: Artificial Sequence
<220> FEATURE:
<223> OTHER INFORMATION: Primer

<400> SEQUENCE: 147
caggcacaca cactttcgtt                                               20

<210> SEQ ID NO 148
<211> LENGTH: 21
<212> TYPE: DNA
<213> ORGANISM: Artificial Sequence
<220> FEATURE:
<223> OTHER INFORMATION: Primer

<400> SEQUENCE: 148
ttctcatgca gtcaaccatt g                                             21

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
agacgtccaa aggtcgctaa                                               20
```

```
<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
ccctcactgc ctgtaaacct                                              20

<210> SEQ ID NO 151
<211> LENGTH: 20
<212> TYPE: DNA
<213> ORGANISM: Artificial Sequence
<220> FEATURE:
<223> OTHER INFORMATION: Primer

<400> SEQUENCE: 151
atcacaaaaa caggggccta                                              20

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
ccttgtctgg ctcaatcacc                                              20

<210> SEQ ID NO 153
<211> LENGTH: 20
<212> TYPE: DNA
<213> ORGANISM: Artificial Sequence
<220> FEATURE:
<223> OTHER INFORMATION: Primer

<400> SEQUENCE: 153
ctgctccaca ttcccattct                                              20

<210> SEQ ID NO 154
<211> LENGTH: 20
<212> TYPE: DNA
<213> ORGANISM: Artificial Sequence
<220> FEATURE:
<223> OTHER INFORMATION: Primer

<400> SEQUENCE: 154
tggcaggaaa catctgttca                                              20

<210> SEQ ID NO 155
<211> LENGTH: 21
<212> TYPE: DNA
<213> ORGANISM: Artificial Sequence
<220> FEATURE:
<223> OTHER INFORMATION: Primer

<400> SEQUENCE: 155
tggctgagta aaatggtgac a                                            21

<210> SEQ ID NO 156
<211> LENGTH: 20
<212> TYPE: DNA
<213> ORGANISM: Artificial Sequence
<220> FEATURE:
<223> OTHER INFORMATION: Primer
```

<400> SEQUENCE: 156
gcttggggga atttcttgat                                                      20

<210> SEQ ID NO 157
<211> LENGTH: 20
<212> TYPE: DNA
<213> ORGANISM: Artificial Sequence
<220> FEATURE:
<223> OTHER INFORMATION: Primer

<400> SEQUENCE: 157
cagaaggtca ggaccacaca                                                      20

<210> SEQ ID NO 158
<211> LENGTH: 20
<212> TYPE: DNA
<213> ORGANISM: Artificial Sequence
<220> FEATURE:
<223> OTHER INFORMATION: Primer

<400> SEQUENCE: 158
atttggtggg ttccagtgag                                                      20

<210> SEQ ID NO 159
<211> LENGTH: 21
<212> TYPE: DNA
<213> ORGANISM: Artificial Sequence
<220> FEATURE:
<223> OTHER INFORMATION: Primer

<400> SEQUENCE: 159
cctcctagca ttccatagca c                                                    21

<210> SEQ ID NO 160
<211> LENGTH: 21
<212> TYPE: DNA
<213> ORGANISM: Artificial Sequence
<220> FEATURE:
<223> OTHER INFORMATION: Primer

<400> SEQUENCE: 160
tgcaacctcg taagctcatt t                                                    21

<210> SEQ ID NO 161
<211> LENGTH: 20
<212> TYPE: DNA
<213> ORGANISM: Artificial Sequence
<220> FEATURE:
<223> OTHER INFORMATION: Primer

<400> SEQUENCE: 161
gccacatttg ctggtattca                                                      20

<210> SEQ ID NO 162
<211> LENGTH: 20
<212> TYPE: DNA
<213> ORGANISM: Artificial Sequence
<220> FEATURE:
<223> OTHER INFORMATION: Primer

<400> SEQUENCE: 162
tttttcctct gggaaaccat                                                      20

<210> SEQ ID NO 163

```
<211> LENGTH: 23
<212> TYPE: DNA
<213> ORGANISM: Artificial Sequence
<220> FEATURE:
<223> OTHER INFORMATION: Primer

<400> SEQUENCE: 163
tggttcagac atacacgtac agg                                             23

<210> SEQ ID NO 164
<211> LENGTH: 20
<212> TYPE: DNA
<213> ORGANISM: Artificial Sequence
<220> FEATURE:
<223> OTHER INFORMATION: Primer

<400> SEQUENCE: 164
ataacaggca caagggtgga                                                 20

<210> SEQ ID NO 165
<211> LENGTH: 21
<212> TYPE: DNA
<213> ORGANISM: Artificial Sequence
<220> FEATURE:
<223> OTHER INFORMATION: Primer

<400> SEQUENCE: 165
cctggcaaat gatgctttag a                                               21

<210> SEQ ID NO 166
<211> LENGTH: 20
<212> TYPE: DNA
<213> ORGANISM: Artificial Sequence
<220> FEATURE:
<223> OTHER INFORMATION: Primer

<400> SEQUENCE: 166
cctccctcct aggctcaagt                                                 20

<210> SEQ ID NO 167
<211> LENGTH: 20
<212> TYPE: DNA
<213> ORGANISM: Artificial Sequence
<220> FEATURE:
<223> OTHER INFORMATION: Primer

<400> SEQUENCE: 167
cgaggcgggt atttacttga                                                 20

<210> SEQ ID NO 168
<211> LENGTH: 20
<212> TYPE: DNA
<213> ORGANISM: Artificial Sequence
<220> FEATURE:
<223> OTHER INFORMATION: Primer

<400> SEQUENCE: 168
ggagttgggg caaaaatcac                                                 20

<210> SEQ ID NO 169
<211> LENGTH: 18
<212> TYPE: DNA
<213> ORGANISM: Artificial Sequence
<220> FEATURE:
<223> OTHER INFORMATION: Primer

<400> SEQUENCE: 169
``` caaaccccg agacacac          18

<210> SEQ ID NO 170
<211> LENGTH: 21
<212> TYPE: DNA
<213> ORGANISM: Artificial Sequence
<220> FEATURE:
<223> OTHER INFORMATION: Primer

<400> SEQUENCE: 170
aacgtggctc tttatcccat t          21

<210> SEQ ID NO 171
<211> LENGTH: 20
<212> TYPE: DNA
<213> ORGANISM: Artificial Sequence
<220> FEATURE:
<223> OTHER INFORMATION: Primer

<400> SEQUENCE: 171
gatggagggc cctttaattt          20

<210> SEQ ID NO 172
<211> LENGTH: 21
<212> TYPE: DNA
<213> ORGANISM: Artificial Sequence
<220> FEATURE:
<223> OTHER INFORMATION: Primer

<400> SEQUENCE: 172
cgatgaagtg gttgatgtga g          21

<210> SEQ ID NO 173
<211> LENGTH: 20
<212> TYPE: DNA
<213> ORGANISM: Artificial Sequence
<220> FEATURE:
<223> OTHER INFORMATION: Primer

<400> SEQUENCE: 173
gacaactccg aagggcaata          20

<210> SEQ ID NO 174
<211> LENGTH: 20
<212> TYPE: DNA
<213> ORGANISM: Artificial Sequence
<220> FEATURE:
<223> OTHER INFORMATION: Primer

<400> SEQUENCE: 174
agtttgggtt gcaagacgtt          20

<210> SEQ ID NO 175
<211> LENGTH: 20
<212> TYPE: DNA
<213> ORGANISM: Artificial Sequence
<220> FEATURE:
<223> OTHER INFORMATION: Primer

<400> SEQUENCE: 175
gcaacattga aatgctggaa          20

<210> SEQ ID NO 176
<211> LENGTH: 20
<212> TYPE: DNA

<213> ORGANISM: Artificial Sequence
<220> FEATURE:
<223> OTHER INFORMATION: Primer

<400> SEQUENCE: 176
taacatttgg gagggggaat                                               20

<210> SEQ ID NO 177
<211> LENGTH: 20
<212> TYPE: DNA
<213> ORGANISM: Artificial Sequence
<220> FEATURE:
<223> OTHER INFORMATION: Primer

<400> SEQUENCE: 177
gctgaatagc gggatcaaaa                                               20

<210> SEQ ID NO 178
<211> LENGTH: 24
<212> TYPE: DNA
<213> ORGANISM: Artificial Sequence
<220> FEATURE:
<223> OTHER INFORMATION: Primer

<400> SEQUENCE: 178
ggaattaggt accagatctc cttt                                          24

<210> SEQ ID NO 179
<211> LENGTH: 20
<212> TYPE: DNA
<213> ORGANISM: Artificial Sequence
<220> FEATURE:
<223> OTHER INFORMATION: Primer

<400> SEQUENCE: 179
gattatcagc ccagggaggt                                               20

<210> SEQ ID NO 180
<211> LENGTH: 20
<212> TYPE: DNA
<213> ORGANISM: Artificial Sequence
<220> FEATURE:
<223> OTHER INFORMATION: Primer

<400> SEQUENCE: 180
atggcagcac tgggaaatta                                               20

<210> SEQ ID NO 181
<211> LENGTH: 20
<212> TYPE: DNA
<213> ORGANISM: Artificial Sequence
<220> FEATURE:
<223> OTHER INFORMATION: Primer

<400> SEQUENCE: 181
tatggctgca gcattaccag                                               20

<210> SEQ ID NO 182
<211> LENGTH: 20
<212> TYPE: DNA
<213> ORGANISM: Artificial Sequence
<220> FEATURE:
<223> OTHER INFORMATION: Primer

<400> SEQUENCE: 182
gccagagtcc acagactcaa                                               20

<210> SEQ ID NO 183
<211> LENGTH: 20
<212> TYPE: DNA
<213> ORGANISM: Artificial Sequence
<220> FEATURE:
<223> OTHER INFORMATION: Primer

<400> SEQUENCE: 183
gagcaaggca tttgaatctg                                           20

<210> SEQ ID NO 184
<211> LENGTH: 20
<212> TYPE: DNA
<213> ORGANISM: Artificial Sequence
<220> FEATURE:
<223> OTHER INFORMATION: Primer

<400> SEQUENCE: 184
atatgaggcg ctctctctcg                                           20

<210> SEQ ID NO 185
<211> LENGTH: 20
<212> TYPE: DNA
<213> ORGANISM: Artificial Sequence
<220> FEATURE:
<223> OTHER INFORMATION: Primer

<400> SEQUENCE: 185
tgcctttggt tgtacctttg                                           20

<210> SEQ ID NO 186
<211> LENGTH: 20
<212> TYPE: DNA
<213> ORGANISM: Artificial Sequence
<220> FEATURE:
<223> OTHER INFORMATION: Primer

<400> SEQUENCE: 186
tcaagtgagc cttgtggaaa                                           20

<210> SEQ ID NO 187
<211> LENGTH: 20
<212> TYPE: DNA
<213> ORGANISM: Artificial Sequence
<220> FEATURE:
<223> OTHER INFORMATION: Primer

<400> SEQUENCE: 187
ccttccccgt tctttctctt                                           20

<210> SEQ ID NO 188
<211> LENGTH: 20
<212> TYPE: DNA
<213> ORGANISM: Artificial Sequence
<220> FEATURE:
<223> OTHER INFORMATION: Primer

<400> SEQUENCE: 188
aaggtaggtg accggctgat                                           20

<210> SEQ ID NO 189
<211> LENGTH: 20
<212> TYPE: DNA
<213> ORGANISM: Artificial Sequence
<220> FEATURE:

<223> OTHER INFORMATION: Primer

<400> SEQUENCE: 189
gcatctcaaa ctgtgcctgt                                              20

<210> SEQ ID NO 190
<211> LENGTH: 20
<212> TYPE: DNA
<213> ORGANISM: Artificial Sequence
<220> FEATURE:
<223> OTHER INFORMATION: Primer

<400> SEQUENCE: 190
cacgggtcta actgtcctca                                              20

<210> SEQ ID NO 191
<211> LENGTH: 20
<212> TYPE: DNA
<213> ORGANISM: Artificial Sequence
<220> FEATURE:
<223> OTHER INFORMATION: Primer

<400> SEQUENCE: 191
ccactccagc aagtctccag                                              20

<210> SEQ ID NO 192
<211> LENGTH: 20
<212> TYPE: DNA
<213> ORGANISM: Artificial Sequence
<220> FEATURE:
<223> OTHER INFORMATION: Primer

<400> SEQUENCE: 192
caagggcctg ctgtatgtca                                              20

<210> SEQ ID NO 193
<211> LENGTH: 20
<212> TYPE: DNA
<213> ORGANISM: Artificial Sequence
<220> FEATURE:
<223> OTHER INFORMATION: Primer

<400> SEQUENCE: 193
agcccatgtt ttccacagaa                                              20

<210> SEQ ID NO 194
<211> LENGTH: 20
<212> TYPE: DNA
<213> ORGANISM: Artificial Sequence
<220> FEATURE:
<223> OTHER INFORMATION: Primer

<400> SEQUENCE: 194
taccaggtgc cctaaacagg                                              20

<210> SEQ ID NO 195
<211> LENGTH: 21
<212> TYPE: DNA
<213> ORGANISM: Artificial Sequence
<220> FEATURE:
<223> OTHER INFORMATION: Primer

<400> SEQUENCE: 195
ttctagacac agacgcacac g                                            21

```
<210> SEQ ID NO 196
<211> LENGTH: 21
<212> TYPE: DNA
<213> ORGANISM: Artificial Sequence
<220> FEATURE:
<223> OTHER INFORMATION: Primer

<400> SEQUENCE: 196
gggactgcca ctagtagctc a                                              21

<210> SEQ ID NO 197
<211> LENGTH: 20
<212> TYPE: DNA
<213> ORGANISM: Artificial Sequence
<220> FEATURE:
<223> OTHER INFORMATION: Primer

<400> SEQUENCE: 197
tgggggcagt ttctattctg                                                20

<210> SEQ ID NO 198
<211> LENGTH: 20
<212> TYPE: DNA
<213> ORGANISM: Artificial Sequence
<220> FEATURE:
<223> OTHER INFORMATION: Primer

<400> SEQUENCE: 198
atcagttttc gatggggaga                                                20

<210> SEQ ID NO 199
<211> LENGTH: 20
<212> TYPE: DNA
<213> ORGANISM: Artificial Sequence
<220> FEATURE:
<223> OTHER INFORMATION: Primer

<400> SEQUENCE: 199
ttggatgctg gattttgaca                                                20

<210> SEQ ID NO 200
<211> LENGTH: 20
<212> TYPE: DNA
<213> ORGANISM: Artificial Sequence
<220> FEATURE:
<223> OTHER INFORMATION: Primer

<400> SEQUENCE: 200
ctcatatccc cctcccagaa                                                20

<210> SEQ ID NO 201
<211> LENGTH: 20
<212> TYPE: DNA
<213> ORGANISM: Artificial Sequence
<220> FEATURE:
<223> OTHER INFORMATION: Primer

<400> SEQUENCE: 201
tattggccag gaattttttgc                                               20

<210> SEQ ID NO 202
<211> LENGTH: 20
<212> TYPE: DNA
<213> ORGANISM: Artificial Sequence
<220> FEATURE:
<223> OTHER INFORMATION: Primer
```

<400> SEQUENCE: 202
ggagctcacg ctaatgacct                                               20

<210> SEQ ID NO 203
<211> LENGTH: 20
<212> TYPE: DNA
<213> ORGANISM: Artificial Sequence
<220> FEATURE:
<223> OTHER INFORMATION: Primer

<400> SEQUENCE: 203
ccccaagctg tttcctccat                                               20

<210> SEQ ID NO 204
<211> LENGTH: 20
<212> TYPE: DNA
<213> ORGANISM: Artificial Sequence
<220> FEATURE:
<223> OTHER INFORMATION: Primer

<400> SEQUENCE: 204
gctggggcaa gaaattcagc                                               20

<210> SEQ ID NO 205
<211> LENGTH: 20
<212> TYPE: DNA
<213> ORGANISM: Artificial Sequence
<220> FEATURE:
<223> OTHER INFORMATION: Primer

<400> SEQUENCE: 205
gagctgccta ctcgctgact                                               20

<210> SEQ ID NO 206
<211> LENGTH: 20
<212> TYPE: DNA
<213> ORGANISM: Artificial Sequence
<220> FEATURE:
<223> OTHER INFORMATION: Primer

<400> SEQUENCE: 206
gccactgatg acaacctcct                                               20

<210> SEQ ID NO 207
<211> LENGTH: 24
<212> TYPE: DNA
<213> ORGANISM: Artificial Sequence
<220> FEATURE:
<223> OTHER INFORMATION: Primer

<400> SEQUENCE: 207
catctagcat tctctcattt cagc                                          24

<210> SEQ ID NO 208
<211> LENGTH: 20
<212> TYPE: DNA
<213> ORGANISM: Artificial Sequence
<220> FEATURE:
<223> OTHER INFORMATION: Primer

<400> SEQUENCE: 208
tgccaaaacc aaagacaagg                                               20

<210> SEQ ID NO 209
<211> LENGTH: 20

<212> TYPE: DNA
<213> ORGANISM: Artificial Sequence
<220> FEATURE:
<223> OTHER INFORMATION: Primer

<400> SEQUENCE: 209
ggctgcttaa gggaaagtgc                                                    20

<210> SEQ ID NO 210
<211> LENGTH: 21
<212> TYPE: DNA
<213> ORGANISM: Artificial Sequence
<220> FEATURE:
<223> OTHER INFORMATION: Primer

<400> SEQUENCE: 210
cgtgttttgg tcaaagttgt g                                                  21

<210> SEQ ID NO 211
<211> LENGTH: 21
<212> TYPE: DNA
<213> ORGANISM: Artificial Sequence
<220> FEATURE:
<223> OTHER INFORMATION: Primer

<400> SEQUENCE: 211
atgtttggtg catgaaatct g                                                  21

<210> SEQ ID NO 212
<211> LENGTH: 20
<212> TYPE: DNA
<213> ORGANISM: Artificial Sequence
<220> FEATURE:
<223> OTHER INFORMATION: Primer

<400> SEQUENCE: 212
tgagttccac atggctcttg                                                    20

<210> SEQ ID NO 213
<211> LENGTH: 20
<212> TYPE: DNA
<213> ORGANISM: Artificial Sequence
<220> FEATURE:
<223> OTHER INFORMATION: Primer

<400> SEQUENCE: 213
tattcccctt gtgtgggaga                                                    20

<210> SEQ ID NO 214
<211> LENGTH: 20
<212> TYPE: DNA
<213> ORGANISM: Artificial Sequence
<220> FEATURE:
<223> OTHER INFORMATION: Primer

<400> SEQUENCE: 214
caaagagaat gggtgggagt                                                    20

<210> SEQ ID NO 215
<211> LENGTH: 20
<212> TYPE: DNA
<213> ORGANISM: Artificial Sequence
<220> FEATURE:
<223> OTHER INFORMATION: Primer

<400> SEQUENCE: 215

```
ggtgaggaaa gcacaaggtc                                              20

<210> SEQ ID NO 216
<211> LENGTH: 20
<212> TYPE: DNA
<213> ORGANISM: Artificial Sequence
<220> FEATURE:
<223> OTHER INFORMATION: Primer

<400> SEQUENCE: 216
ccgtggaatt tcttctgcac                                              20

<210> SEQ ID NO 217
<211> LENGTH: 21
<212> TYPE: DNA
<213> ORGANISM: Artificial Sequence
<220> FEATURE:
<223> OTHER INFORMATION: Primer

<400> SEQUENCE: 217
tcctcgtcct ctcagatgtg t                                            21

<210> SEQ ID NO 218
<211> LENGTH: 21
<212> TYPE: DNA
<213> ORGANISM: Artificial Sequence
<220> FEATURE:
<223> OTHER INFORMATION: Primer

<400> SEQUENCE: 218
tcaggactta gcaccaggaa a                                            21

<210> SEQ ID NO 219
<211> LENGTH: 20
<212> TYPE: DNA
<213> ORGANISM: Artificial Sequence
<220> FEATURE:
<223> OTHER INFORMATION: Primer

<400> SEQUENCE: 219
cccgttttca gaccaagtgt                                              20

<210> SEQ ID NO 220
<211> LENGTH: 20
<212> TYPE: DNA
<213> ORGANISM: Artificial Sequence
<220> FEATURE:
<223> OTHER INFORMATION: Primer

<400> SEQUENCE: 220
ttggaacagg atgggtgaat                                              20

<210> SEQ ID NO 221
<211> LENGTH: 20
<212> TYPE: DNA
<213> ORGANISM: Artificial Sequence
<220> FEATURE:
<223> OTHER INFORMATION: Primer

<400> SEQUENCE: 221
tgattcgggc ttggacttag                                              20

<210> SEQ ID NO 222
<211> LENGTH: 20
<212> TYPE: DNA
<213> ORGANISM: Artificial Sequence
```

```
<220> FEATURE:
<223> OTHER INFORMATION: Primer

<400> SEQUENCE: 222
gtcaatcact ttgcctgctc                                                20

<210> SEQ ID NO 223
<211> LENGTH: 20
<212> TYPE: DNA
<213> ORGANISM: Artificial Sequence
<220> FEATURE:
<223> OTHER INFORMATION: Primer

<400> SEQUENCE: 223
gtttgatctc tggccctgtc                                                20

<210> SEQ ID NO 224
<211> LENGTH: 21
<212> TYPE: DNA
<213> ORGANISM: Artificial Sequence
<220> FEATURE:
<223> OTHER INFORMATION: Primer

<400> SEQUENCE: 224
gcctccttaa tctcctccat c                                              21

<210> SEQ ID NO 225
<211> LENGTH: 20
<212> TYPE: DNA
<213> ORGANISM: Artificial Sequence
<220> FEATURE:
<223> OTHER INFORMATION: Primer

<400> SEQUENCE: 225
agaccacccc ttaggcaaac                                                20

<210> SEQ ID NO 226
<211> LENGTH: 20
<212> TYPE: DNA
<213> ORGANISM: Artificial Sequence
<220> FEATURE:
<223> OTHER INFORMATION: Primer

<400> SEQUENCE: 226
agtgcagcaa ggcagatgag                                                20

<210> SEQ ID NO 227
<211> LENGTH: 20
<212> TYPE: DNA
<213> ORGANISM: Artificial Sequence
<220> FEATURE:
<223> OTHER INFORMATION: Primer

<400> SEQUENCE: 227
tggggaggga acctcattac                                                20

<210> SEQ ID NO 228
<211> LENGTH: 21
<212> TYPE: DNA
<213> ORGANISM: Artificial Sequence
<220> FEATURE:
<223> OTHER INFORMATION: Primer

<400> SEQUENCE: 228
cagtgcctgt tgagtagaac c                                              21
```

<210> SEQ ID NO 229
<211> LENGTH: 22
<212> TYPE: DNA
<213> ORGANISM: Artificial Sequence
<220> FEATURE:
<223> OTHER INFORMATION: Primer

<400> SEQUENCE: 229
tgagtgctgc tcatattttt cc                                        22

<210> SEQ ID NO 230
<211> LENGTH: 21
<212> TYPE: DNA
<213> ORGANISM: Artificial Sequence
<220> FEATURE:
<223> OTHER INFORMATION: Primer

<400> SEQUENCE: 230
ggggcttcag tctcaggata g                                         21

<210> SEQ ID NO 231
<211> LENGTH: 21
<212> TYPE: DNA
<213> ORGANISM: Artificial Sequence
<220> FEATURE:
<223> OTHER INFORMATION: Primer

<400> SEQUENCE: 231
tcagcctatg aagatcctct g                                         21

<210> SEQ ID NO 232
<211> LENGTH: 20
<212> TYPE: DNA
<213> ORGANISM: Artificial Sequence
<220> FEATURE:
<223> OTHER INFORMATION: Primer

<400> SEQUENCE: 232
aaggaagacg gggaagactg                                           20

<210> SEQ ID NO 233
<211> LENGTH: 22
<212> TYPE: DNA
<213> ORGANISM: Artificial Sequence
<220> FEATURE:
<223> OTHER INFORMATION: Primer

<400> SEQUENCE: 233
tgggtacaaa gctcaagtca ac                                        22

<210> SEQ ID NO 234
<211> LENGTH: 20
<212> TYPE: DNA
<213> ORGANISM: Artificial Sequence
<220> FEATURE:
<223> OTHER INFORMATION: Primer

<400> SEQUENCE: 234
tctccaaagg cttctccttg                                           20

<210> SEQ ID NO 235
<211> LENGTH: 23
<212> TYPE: DNA
<213> ORGANISM: Artificial Sequence
<220> FEATURE:
<223> OTHER INFORMATION: Primer

```
<400> SEQUENCE: 235
tgtagcctag gtaaagagga caa                                        23

<210> SEQ ID NO 236
<211> LENGTH: 21
<212> TYPE: DNA
<213> ORGANISM: Artificial Sequence
<220> FEATURE:
<223> OTHER INFORMATION: Primer

<400> SEQUENCE: 236
catttagcat tttgccattc c                                          21

<210> SEQ ID NO 237
<211> LENGTH: 20
<212> TYPE: DNA
<213> ORGANISM: Artificial Sequence
<220> FEATURE:
<223> OTHER INFORMATION: Primer

<400> SEQUENCE: 237
tatgccttct ggaggagtgg                                            20

<210> SEQ ID NO 238
<211> LENGTH: 20
<212> TYPE: DNA
<213> ORGANISM: Artificial Sequence
<220> FEATURE:
<223> OTHER INFORMATION: Primer

<400> SEQUENCE: 238
tggaatagcg gtaaggcttg                                            20

<210> SEQ ID NO 239
<211> LENGTH: 20
<212> TYPE: DNA
<213> ORGANISM: Artificial Sequence
<220> FEATURE:
<223> OTHER INFORMATION: Primer

<400> SEQUENCE: 239
ttaacctgcc agctcagttc                                            20

<210> SEQ ID NO 240
<211> LENGTH: 20
<212> TYPE: DNA
<213> ORGANISM: Artificial Sequence
<220> FEATURE:
<223> OTHER INFORMATION: Primer

<400> SEQUENCE: 240
gcttccactc atttgcattg                                            20

<210> SEQ ID NO 241
<211> LENGTH: 21
<212> TYPE: DNA
<213> ORGANISM: Artificial Sequence
<220> FEATURE:
<223> OTHER INFORMATION: Primer

<400> SEQUENCE: 241
tgcataggca gacctcaaaa c                                          21

<210> SEQ ID NO 242
```

```
<211> LENGTH: 21
<212> TYPE: DNA
<213> ORGANISM: Artificial Sequence
<220> FEATURE:
<223> OTHER INFORMATION: Primer

<400> SEQUENCE: 242
gaaagcctga tgtttgacac c                                                21

<210> SEQ ID NO 243
<211> LENGTH: 20
<212> TYPE: DNA
<213> ORGANISM: Artificial Sequence
<220> FEATURE:
<223> OTHER INFORMATION: Primer

<400> SEQUENCE: 243
tttggtcatt gctgtcatgg                                                  20

<210> SEQ ID NO 244
<211> LENGTH: 21
<212> TYPE: DNA
<213> ORGANISM: Artificial Sequence
<220> FEATURE:
<223> OTHER INFORMATION: Primer

<400> SEQUENCE: 244
caacaaggaa ttgaatgatg c                                                21

<210> SEQ ID NO 245
<211> LENGTH: 21
<212> TYPE: DNA
<213> ORGANISM: Artificial Sequence
<220> FEATURE:
<223> OTHER INFORMATION: Primer

<400> SEQUENCE: 245
tgagtccctt ttgaaatgtt g                                                21

<210> SEQ ID NO 246
<211> LENGTH: 21
<212> TYPE: DNA
<213> ORGANISM: Artificial Sequence
<220> FEATURE:
<223> OTHER INFORMATION: Primer

<400> SEQUENCE: 246
gccaaccaat ggagttttaa g                                                21

<210> SEQ ID NO 247
<211> LENGTH: 22
<212> TYPE: DNA
<213> ORGANISM: Artificial Sequence
<220> FEATURE:
<223> OTHER INFORMATION: Primer

<400> SEQUENCE: 247
caatgtttga ttaaccatga cg                                               22

<210> SEQ ID NO 248
<211> LENGTH: 22
<212> TYPE: DNA
<213> ORGANISM: Artificial Sequence
<220> FEATURE:
<223> OTHER INFORMATION: Primer

<400> SEQUENCE: 248
``` gcactttttct cacacaattt gg                                            22

<210> SEQ ID NO 249
<211> LENGTH: 20
<212> TYPE: DNA
<213> ORGANISM: Artificial Sequence
<220> FEATURE:
<223> OTHER INFORMATION: Primer

<400> SEQUENCE: 249
gcaggaattc attctgaagc                                                20

<210> SEQ ID NO 250
<211> LENGTH: 20
<212> TYPE: DNA
<213> ORGANISM: Artificial Sequence
<220> FEATURE:
<223> OTHER INFORMATION: Primer

<400> SEQUENCE: 250
aacgcagtga ggaacaaagg                                                20

<210> SEQ ID NO 251
<211> LENGTH: 21
<212> TYPE: DNA
<213> ORGANISM: Artificial Sequence
<220> FEATURE:
<223> OTHER INFORMATION: Primer

<400> SEQUENCE: 251
tggatttgca tctgtgaatt g                                              21

<210> SEQ ID NO 252
<211> LENGTH: 22
<212> TYPE: DNA
<213> ORGANISM: Artificial Sequence
<220> FEATURE:
<223> OTHER INFORMATION: Primer

<400> SEQUENCE: 252
ttttgatggc ttttactttt cc                                             22

<210> SEQ ID NO 253
<211> LENGTH: 20
<212> TYPE: DNA
<213> ORGANISM: Artificial Sequence
<220> FEATURE:
<223> OTHER INFORMATION: Primer

<400> SEQUENCE: 253
ctgcctatgc caaacaaatg                                                20

<210> SEQ ID NO 254
<211> LENGTH: 20
<212> TYPE: DNA
<213> ORGANISM: Artificial Sequence
<220> FEATURE:
<223> OTHER INFORMATION: Primer

<400> SEQUENCE: 254
agcacaagcc ttttgtcagc                                                20

<210> SEQ ID NO 255
<211> LENGTH: 20
<212> TYPE: DNA

```
<213> ORGANISM: Artificial Sequence
<220> FEATURE:
<223> OTHER INFORMATION: Primer

<400> SEQUENCE: 255
gaatagcggg aagaactgga                                              20

<210> SEQ ID NO 256
<211> LENGTH: 20
<212> TYPE: DNA
<213> ORGANISM: Artificial Sequence
<220> FEATURE:
<223> OTHER INFORMATION: Primer

<400> SEQUENCE: 256
tgcattcgaa tcaggaatga                                              20

<210> SEQ ID NO 257
<211> LENGTH: 20
<212> TYPE: DNA
<213> ORGANISM: Artificial Sequence
<220> FEATURE:
<223> OTHER INFORMATION: Primer

<400> SEQUENCE: 257
cccatcctta gaccccagac                                              20

<210> SEQ ID NO 258
<211> LENGTH: 20
<212> TYPE: DNA
<213> ORGANISM: Artificial Sequence
<220> FEATURE:
<223> OTHER INFORMATION: Primer

<400> SEQUENCE: 258
gaaaatgaga cgcgaaaagg                                              20

<210> SEQ ID NO 259
<211> LENGTH: 20
<212> TYPE: DNA
<213> ORGANISM: Artificial Sequence
<220> FEATURE:
<223> OTHER INFORMATION: Primer

<400> SEQUENCE: 259
aaagcttgtg ggtgatggag                                              20

<210> SEQ ID NO 260
<211> LENGTH: 21
<212> TYPE: DNA
<213> ORGANISM: Artificial Sequence
<220> FEATURE:
<223> OTHER INFORMATION: Primer

<400> SEQUENCE: 260
tgcttggaat aggatgcttt g                                            21

<210> SEQ ID NO 261
<211> LENGTH: 20
<212> TYPE: DNA
<213> ORGANISM: Artificial Sequence
<220> FEATURE:
<223> OTHER INFORMATION: Primer

<400> SEQUENCE: 261
tccccaggac cctagtcttc                                              20
```

<210> SEQ ID NO 262
<211> LENGTH: 21
<212> TYPE: DNA
<213> ORGANISM: Artificial Sequence
<220> FEATURE:
<223> OTHER INFORMATION: Primer

<400> SEQUENCE: 262
ggtggcaagc acttttgtaa g                                         21

<210> SEQ ID NO 263
<211> LENGTH: 20
<212> TYPE: DNA
<213> ORGANISM: Artificial Sequence
<220> FEATURE:
<223> OTHER INFORMATION: Primer

<400> SEQUENCE: 263
agcatgggaa taacgacagg                                           20

<210> SEQ ID NO 264
<211> LENGTH: 21
<212> TYPE: DNA
<213> ORGANISM: Artificial Sequence
<220> FEATURE:
<223> OTHER INFORMATION: Primer

<400> SEQUENCE: 264
tcgttgtgtt ggaggtagag c                                         21

<210> SEQ ID NO 265
<211> LENGTH: 23
<212> TYPE: DNA
<213> ORGANISM: Artificial Sequence
<220> FEATURE:
<223> OTHER INFORMATION: Primer

<400> SEQUENCE: 265
aaatgaacac tatgcatgtc agg                                       23

<210> SEQ ID NO 266
<211> LENGTH: 20
<212> TYPE: DNA
<213> ORGANISM: Artificial Sequence
<220> FEATURE:
<223> OTHER INFORMATION: Primer

<400> SEQUENCE: 266
ttgcctcttg caactgattg                                           20

<210> SEQ ID NO 267
<211> LENGTH: 19
<212> TYPE: DNA
<213> ORGANISM: Artificial Sequence
<220> FEATURE:
<223> OTHER INFORMATION: Primer

<400> SEQUENCE: 267
catggaccgc tgatctctg                                            19

<210> SEQ ID NO 268
<211> LENGTH: 19
<212> TYPE: DNA
<213> ORGANISM: Artificial Sequence
<220> FEATURE:

```
<223> OTHER INFORMATION: Primer

<400> SEQUENCE: 268
ggagggatct agccaccac                                          19

<210> SEQ ID NO 269
<211> LENGTH: 20
<212> TYPE: DNA
<213> ORGANISM: Artificial Sequence
<220> FEATURE:
<223> OTHER INFORMATION: Primer

<400> SEQUENCE: 269
ggcaacagcc tcataactgc                                         20

<210> SEQ ID NO 270
<211> LENGTH: 20
<212> TYPE: DNA
<213> ORGANISM: Artificial Sequence
<220> FEATURE:
<223> OTHER INFORMATION: Primer

<400> SEQUENCE: 270
gctgtctcct ggctctaacc                                         20

<210> SEQ ID NO 271
<211> LENGTH: 18
<212> TYPE: DNA
<213> ORGANISM: Artificial Sequence
<220> FEATURE:
<223> OTHER INFORMATION: Primer

<400> SEQUENCE: 271
tttggctggg cctggtag                                           18

<210> SEQ ID NO 272
<211> LENGTH: 20
<212> TYPE: DNA
<213> ORGANISM: Artificial Sequence
<220> FEATURE:
<223> OTHER INFORMATION: Primer

<400> SEQUENCE: 272
cagagtgcac ctcagtgacc                                         20

<210> SEQ ID NO 273
<211> LENGTH: 23
<212> TYPE: DNA
<213> ORGANISM: Artificial Sequence
<220> FEATURE:
<223> OTHER INFORMATION: Primer

<400> SEQUENCE: 273
tgcagagaag agatacagaa agc                                     23

<210> SEQ ID NO 274
<211> LENGTH: 21
<212> TYPE: DNA
<213> ORGANISM: Artificial Sequence
<220> FEATURE:
<223> OTHER INFORMATION: Primer

<400> SEQUENCE: 274
tgcaaaaatc ccagattgaa g                                       21
```

```
<210> SEQ ID NO 275
<211> LENGTH: 21
<212> TYPE: DNA
<213> ORGANISM: Artificial Sequence
<220> FEATURE:
<223> OTHER INFORMATION: Primer

<400> SEQUENCE: 275
gagtgtggga gaagtcctac g                                              21

<210> SEQ ID NO 276
<211> LENGTH: 21
<212> TYPE: DNA
<213> ORGANISM: Artificial Sequence
<220> FEATURE:
<223> OTHER INFORMATION: Primer

<400> SEQUENCE: 276
ttcaggagat gaaaaggctt g                                              21

<210> SEQ ID NO 277
<211> LENGTH: 21
<212> TYPE: DNA
<213> ORGANISM: Artificial Sequence
<220> FEATURE:
<223> OTHER INFORMATION: Primer

<400> SEQUENCE: 277
tccctgaagg aaggaaaaat c                                              21

<210> SEQ ID NO 278
<211> LENGTH: 22
<212> TYPE: DNA
<213> ORGANISM: Artificial Sequence
<220> FEATURE:
<223> OTHER INFORMATION: Primer

<400> SEQUENCE: 278
gtgattgtga agttggattt gc                                             22

<210> SEQ ID NO 279
<211> LENGTH: 20
<212> TYPE: DNA
<213> ORGANISM: Artificial Sequence
<220> FEATURE:
<223> OTHER INFORMATION: Primer

<400> SEQUENCE: 279
attacccatg ggggatgttg                                                20

<210> SEQ ID NO 280
<211> LENGTH: 20
<212> TYPE: DNA
<213> ORGANISM: Artificial Sequence
<220> FEATURE:
<223> OTHER INFORMATION: Primer

<400> SEQUENCE: 280
agttggggaa cattccttcc                                                20

<210> SEQ ID NO 281
<211> LENGTH: 20
<212> TYPE: DNA
<213> ORGANISM: Artificial Sequence
<220> FEATURE:
<223> OTHER INFORMATION: Primer
```

<400> SEQUENCE: 281
atctgtaagg atcgggctga                                    20

<210> SEQ ID NO 282
<211> LENGTH: 20
<212> TYPE: DNA
<213> ORGANISM: Artificial Sequence
<220> FEATURE:
<223> OTHER INFORMATION: Primer

<400> SEQUENCE: 282
caacacaacg ccatactgct                                    20

<210> SEQ ID NO 283
<211> LENGTH: 20
<212> TYPE: DNA
<213> ORGANISM: Artificial Sequence
<220> FEATURE:
<223> OTHER INFORMATION: Primer

<400> SEQUENCE: 283
ttccccattt gatgatcctg                                    20

<210> SEQ ID NO 284
<211> LENGTH: 20
<212> TYPE: DNA
<213> ORGANISM: Artificial Sequence
<220> FEATURE:
<223> OTHER INFORMATION: Primer

<400> SEQUENCE: 284
agagttttcc ccactcagca                                    20

<210> SEQ ID NO 285
<211> LENGTH: 20
<212> TYPE: DNA
<213> ORGANISM: Artificial Sequence
<220> FEATURE:
<223> OTHER INFORMATION: Primer

<400> SEQUENCE: 285
tgaatatgcc tcaagcacca                                    20

<210> SEQ ID NO 286
<211> LENGTH: 23
<212> TYPE: DNA
<213> ORGANISM: Artificial Sequence
<220> FEATURE:
<223> OTHER INFORMATION: Primer

<400> SEQUENCE: 286
aatgcaaacc tcctaggtta aaa                                23

<210> SEQ ID NO 287
<211> LENGTH: 20
<212> TYPE: DNA
<213> ORGANISM: Artificial Sequence
<220> FEATURE:
<223> OTHER INFORMATION: Primer

<400> SEQUENCE: 287
gtgctctgca tctcatacgc                                    20

<210> SEQ ID NO 288
<211> LENGTH: 20

```
<212> TYPE: DNA
<213> ORGANISM: Artificial Sequence
<220> FEATURE:
<223> OTHER INFORMATION: Primer

<400> SEQUENCE: 288
cctccttggc taacttgctc                                            20

<210> SEQ ID NO 289
<211> LENGTH: 52
<212> TYPE: DNA
<213> ORGANISM: Artificial Sequence
<220> FEATURE:
<223> OTHER INFORMATION: Primer

<400> SEQUENCE: 289
tcgtcggcag cgtcagatgt gtataagaga caggagaccc cagtcttgcg ac         52

<210> SEQ ID NO 290
<211> LENGTH: 52
<212> TYPE: DNA
<213> ORGANISM: Artificial Sequence
<220> FEATURE:
<223> OTHER INFORMATION: Primer

<400> SEQUENCE: 290
tcgtcggcag cgtcagatgt gtataagaga cagcaggagg tgctggaaat cc         52

<210> SEQ ID NO 291
<211> LENGTH: 54
<212> TYPE: DNA
<213> ORGANISM: Artificial Sequence
<220> FEATURE:
<223> OTHER INFORMATION: Primer

<400> SEQUENCE: 291
tcgtcggcag cgtcagatgt gtataagaga cagggcattg cccctatata ctgt       54

<210> SEQ ID NO 292
<211> LENGTH: 58
<212> TYPE: DNA
<213> ORGANISM: Artificial Sequence
<220> FEATURE:
<223> OTHER INFORMATION: Primer

<400> SEQUENCE: 292
tcgtcggcag cgtcagatgt gtataagaga cagcctacgt atctaagtat tctccagc   58

<210> SEQ ID NO 293
<211> LENGTH: 56
<212> TYPE: DNA
<213> ORGANISM: Artificial Sequence
<220> FEATURE:
<223> OTHER INFORMATION: Primer

<400> SEQUENCE: 293
tcgtcggcag cgtcagatgt gtataagaga cagggtaacc aaagcaggaa aacatt     56

<210> SEQ ID NO 294
<211> LENGTH: 56
<212> TYPE: DNA
<213> ORGANISM: Artificial Sequence
<220> FEATURE:
<223> OTHER INFORMATION: Primer

<400> SEQUENCE: 294
```
tcgtcggcag cgtcagatgt gtataagaga caggaatcag cagtgttcat accttc        56

<210> SEQ ID NO 295
<211> LENGTH: 54
<212> TYPE: DNA
<213> ORGANISM: Artificial Sequence
<220> FEATURE:
<223> OTHER INFORMATION: Primer

<400> SEQUENCE: 295
tcgtcggcag cgtcagatgt gtataagaga cagagaagtc agtgcatgtg tctt        54

<210> SEQ ID NO 296
<211> LENGTH: 55
<212> TYPE: DNA
<213> ORGANISM: Artificial Sequence
<220> FEATURE:
<223> OTHER INFORMATION: Primer

<400> SEQUENCE: 296
tcgtcggcag cgtcagatgt gtataagaga cagtccgtat tccaggagta agagt        55

<210> SEQ ID NO 297
<211> LENGTH: 55
<212> TYPE: DNA
<213> ORGANISM: Artificial Sequence
<220> FEATURE:
<223> OTHER INFORMATION: Primer

<400> SEQUENCE: 297
tcgtcggcag cgtcagatgt gtataagaga cagggtggct tgttttcatt ttgtc        55

<210> SEQ ID NO 298
<211> LENGTH: 53
<212> TYPE: DNA
<213> ORGANISM: Artificial Sequence
<220> FEATURE:
<223> OTHER INFORMATION: Primer

<400> SEQUENCE: 298
tcgtcggcag cgtcagatgt gtataagaga caggtggtga ccctgaacgt taa        53

<210> SEQ ID NO 299
<211> LENGTH: 54
<212> TYPE: DNA
<213> ORGANISM: Artificial Sequence
<220> FEATURE:
<223> OTHER INFORMATION: Primer

<400> SEQUENCE: 299
tcgtcggcag cgtcagatgt gtataagaga caggaggcca agagttcaag acca        54

<210> SEQ ID NO 300
<211> LENGTH: 55
<212> TYPE: DNA
<213> ORGANISM: Artificial Sequence
<220> FEATURE:
<223> OTHER INFORMATION: Primer

<400> SEQUENCE: 300
tcgtcggcag cgtcagatgt gtataagaga caggggagga agtatctggt cttct        55

<210> SEQ ID NO 301
<211> LENGTH: 53
<212> TYPE: DNA
<213> ORGANISM: Artificial Sequence

```
<220> FEATURE:
<223> OTHER INFORMATION: Primer

<400> SEQUENCE: 301
tcgtcggcag cgtcagatgt gtataagaga cagtcctgtg gtctgtgaag cta          53

<210> SEQ ID NO 302
<211> LENGTH: 58
<212> TYPE: DNA
<213> ORGANISM: Artificial Sequence
<220> FEATURE:
<223> OTHER INFORMATION: Primer

<400> SEQUENCE: 302
tcgtcggcag cgtcagatgt gtataagaga cagactgtgg ttttaatttg catttccc     58

<210> SEQ ID NO 303
<211> LENGTH: 53
<212> TYPE: DNA
<213> ORGANISM: Artificial Sequence
<220> FEATURE:
<223> OTHER INFORMATION: Primer

<400> SEQUENCE: 303
tcgtcggcag cgtcagatgt gtataagaga caggttcaca cacatgcaag ctg          53

<210> SEQ ID NO 304
<211> LENGTH: 53
<212> TYPE: DNA
<213> ORGANISM: Artificial Sequence
<220> FEATURE:
<223> OTHER INFORMATION: Primer

<400> SEQUENCE: 304
tcgtcggcag cgtcagatgt gtataagaga cagcccaggc taaaagacca aga          53

<210> SEQ ID NO 305
<211> LENGTH: 53
<212> TYPE: DNA
<213> ORGANISM: Artificial Sequence
<220> FEATURE:
<223> OTHER INFORMATION: Primer

<400> SEQUENCE: 305
tcgtcggcag cgtcagatgt gtataagaga cagggtagtt ggatcgcttc agg          53

<210> SEQ ID NO 306
<211> LENGTH: 56
<212> TYPE: DNA
<213> ORGANISM: Artificial Sequence
<220> FEATURE:
<223> OTHER INFORMATION: Primer

<400> SEQUENCE: 306
gtctcgtggg ctcggagatg tgtataagag acagaagtcc ccactttgaa gatgtc       56

<210> SEQ ID NO 307
<211> LENGTH: 52
<212> TYPE: DNA
<213> ORGANISM: Artificial Sequence
<220> FEATURE:
<223> OTHER INFORMATION: Primer

<400> SEQUENCE: 307
gtctcgtggg ctcggagatg tgtataagag acagcatcag ccgcgtcgta gg           52
```

<210> SEQ ID NO 308
<211> LENGTH: 58
<212> TYPE: DNA
<213> ORGANISM: Artificial Sequence
<220> FEATURE:
<223> OTHER INFORMATION: Primer

<400> SEQUENCE: 308
gtctcgtggg ctcggagatg tgtataagag acagttccca gttctgaatc tagaaaga    58

<210> SEQ ID NO 309
<211> LENGTH: 58
<212> TYPE: DNA
<213> ORGANISM: Artificial Sequence
<220> FEATURE:
<223> OTHER INFORMATION: Primer

<400> SEQUENCE: 309
gtctcgtggg ctcggagatg tgtataagag acagacagtg ggtttcaaat gtcacttc    58

<210> SEQ ID NO 310
<211> LENGTH: 55
<212> TYPE: DNA
<213> ORGANISM: Artificial Sequence
<220> FEATURE:
<223> OTHER INFORMATION: Primer

<400> SEQUENCE: 310
gtctcgtggg ctcggagatg tgtataagag acagccctct ctccctggaa taagt    55

<210> SEQ ID NO 311
<211> LENGTH: 58
<212> TYPE: DNA
<213> ORGANISM: Artificial Sequence
<220> FEATURE:
<223> OTHER INFORMATION: Primer

<400> SEQUENCE: 311
gtctcgtggg ctcggagatg tgtataagag acagttgttc actttagtag gaactggt    58

<210> SEQ ID NO 312
<211> LENGTH: 57
<212> TYPE: DNA
<213> ORGANISM: Artificial Sequence
<220> FEATURE:
<223> OTHER INFORMATION: Primer

<400> SEQUENCE: 312
gtctcgtggg ctcggagatg tgtataagag acagcccacc aagattgtaa aatgtga    57

<210> SEQ ID NO 313
<211> LENGTH: 52
<212> TYPE: DNA
<213> ORGANISM: Artificial Sequence
<220> FEATURE:
<223> OTHER INFORMATION: Primer

<400> SEQUENCE: 313
gtctcgtggg ctcggagatg tgtataagag acagctcaga gggaaggtgg ca    52

<210> SEQ ID NO 314
<211> LENGTH: 57
<212> TYPE: DNA
<213> ORGANISM: Artificial Sequence
<220> FEATURE:
<223> OTHER INFORMATION: Primer

```
<400> SEQUENCE: 314
gtctcgtggg ctcggagatg tgtataagag acagcatatg gggtttggtc acatttt       57

<210> SEQ ID NO 315
<211> LENGTH: 55
<212> TYPE: DNA
<213> ORGANISM: Artificial Sequence
<220> FEATURE:
<223> OTHER INFORMATION: Primer

<400> SEQUENCE: 315
gtctcgtggg ctcggagatg tgtataagag acagcctggg tgtaaatgat gggaa         55

<210> SEQ ID NO 316
<211> LENGTH: 57
<212> TYPE: DNA
<213> ORGANISM: Artificial Sequence
<220> FEATURE:
<223> OTHER INFORMATION: Primer

<400> SEQUENCE: 316
gtctcgtggg ctcggagatg tgtataagag acaggatgag aattagcata ccttcca       57

<210> SEQ ID NO 317
<211> LENGTH: 55
<212> TYPE: DNA
<213> ORGANISM: Artificial Sequence
<220> FEATURE:
<223> OTHER INFORMATION: Primer

<400> SEQUENCE: 317
gtctcgtggg ctcggagatg tgtataagag acaggcacat ttacttaagc cctgg         55

<210> SEQ ID NO 318
<211> LENGTH: 54
<212> TYPE: DNA
<213> ORGANISM: Artificial Sequence
<220> FEATURE:
<223> OTHER INFORMATION: Primer

<400> SEQUENCE: 318
gtctcgtggg ctcggagatg tgtataagag acaggtgcat ttgaacatcg cctc          54

<210> SEQ ID NO 319
<211> LENGTH: 54
<212> TYPE: DNA
<213> ORGANISM: Artificial Sequence
<220> FEATURE:
<223> OTHER INFORMATION: Primer

<400> SEQUENCE: 319
gtctcgtggg ctcggagatg tgtataagag acagtgtgcc tttaaagtga cctt          54

<210> SEQ ID NO 320
<211> LENGTH: 54
<212> TYPE: DNA
<213> ORGANISM: Artificial Sequence
<220> FEATURE:
<223> OTHER INFORMATION: Primer

<400> SEQUENCE: 320
gtctcgtggg ctcggagatg tgtataagag acaggaaggg tagggagatg caga          54

<210> SEQ ID NO 321
```

```
<211> LENGTH: 57
<212> TYPE: DNA
<213> ORGANISM: Artificial Sequence
<220> FEATURE:
<223> OTHER INFORMATION: Primer

<400> SEQUENCE: 321
gtctcgtggg ctcggagatg tgtataagag acagcagcaa aggataaaca ttgtgga       57

<210> SEQ ID NO 322
<211> LENGTH: 54
<212> TYPE: DNA
<213> ORGANISM: Artificial Sequence
<220> FEATURE:
<223> OTHER INFORMATION: Primer

<400> SEQUENCE: 322
gtctcgtggg ctcggagatg tgtataagag acagcagcct cttgagtagc ttgg          54

<210> SEQ ID NO 323
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (52)..(57)
<223> OTHER INFORMATION: n is a, c, g, or t

<400> SEQUENCE: 323
gcacattatg ttgtagtcaa gcttcagctt cccgatatcc gacggtagtg tnnnnnngtt    60
tattggccat ttgtatatat t                                              81

<210> SEQ ID NO 324
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (60)..(65)
<223> OTHER INFORMATION: n is a, c, g, or t

<400> SEQUENCE: 324
gtctttgact cacctgtgta gtgtctgcac ttcagcttcc cgatatccga cggtagtgtn    60
nnnnnatgtt cacacacatg c                                              81

<210> SEQ ID NO 325
<211> LENGTH: 80
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (54)..(59)
<223> OTHER INFORMATION: n is a, c, g, or t

<400> SEQUENCE: 325
ccaaacccca tatgtgtggt tgccttcagc ttcccgatat ccgacggtag tgtnnnnnnt    60
gggccctttt aggcatatag                                                80

<210> SEQ ID NO 326
<211> LENGTH: 81
```

```
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (60)..(65)
<223> OTHER INFORMATION: n is a, c, g, or t

<400> SEQUENCE: 326
gcataaggct aggatcattt cattcaagac ttcagcttcc cgatatccga cggtagtgtn    60
nnnnncacaa aaatcaatgc t                                              81

<210> SEQ ID NO 327
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (60)..(65)
<223> OTHER INFORMATION: n is a, c, g, or t

<400> SEQUENCE: 327
gaatacttag atacgtaggt gatactgaac ttcagcttcc cgatatccga cggtagtgtn    60
nnnnncaaaa aagtacagtg g                                              81

<210> SEQ ID NO 328
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (59)..(64)
<223> OTHER INFORMATION: n is a, c, g, or t

<400> SEQUENCE: 328
gcaagggcct gcattgtggt aagtttgtct tcagcttccc gatatccgac ggtagtgtnn    60
nnnngctata aatatccagt g                                              81

<210> SEQ ID NO 329
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (59)..(64)
<223> OTHER INFORMATION: n is a, c, g, or t

<400> SEQUENCE: 329
ttttgaagat gcttgcatag ctatctacct tcagcttccc gatatccgac ggtagtgtnn    60
nnnngctgag taatatatgg g                                              81

<210> SEQ ID NO 330
<211> LENGTH: 80
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (50)..(55)
```

<223> OTHER INFORMATION: n is a, c, g, or t

<400> SEQUENCE: 330
gcacgcctgt aatcccaagc ttcagcttcc cgatatccga cggtagtgtn nnnnnggatc    60
gcttcaggcc aggagttcaa                                               80

<210> SEQ ID NO 331
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (60)..(65)
<223> OTHER INFORMATION: n is a, c, g, or t

<400> SEQUENCE: 331
cctcacattt tataaagact ttcaacaatc ttcagcttcc cgatatccga cggtagtgtn    60
nnnnncattt cctgtgcctt t                                              81

<210> SEQ ID NO 332
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (60)..(65)
<223> OTHER INFORMATION: n is a, c, g, or t

<400> SEQUENCE: 332
gcaactattc aattacagta tatagggcc ttcagcttcc cgatatccga cggtagtgtn     60
nnnnntatca tgaaattcta t                                              81

<210> SEQ ID NO 333
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (59)..(64)
<223> OTHER INFORMATION: n is a, c, g, or t

<400> SEQUENCE: 333
gtgggaaaaa tacttattcc agggagagct tcagcttccc gatatccgac ggtagtgtnn    60
nnnnttttaa aggggaaagg a                                              81

<210> SEQ ID NO 334
<211> LENGTH: 76
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (52)..(57)
<223> OTHER INFORMATION: n is a, c, g, or t

<400> SEQUENCE: 334
agagtgcaaa gataaatgtg ccttcagctt cccgatatcc gacggtagtg tnnnnnnagt    60
ggctggcact tgtggt                                                    76

```
<210> SEQ ID NO 335
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (59)..(64)
<223> OTHER INFORMATION: n is a, c, g, or t

<400> SEQUENCE: 335
cacttttgtt ccttgactgt tttttactct tcagcttccc gatatccgac ggtagtgtnn     60
nnnnctgagg taggctcatt t                                               81

<210> SEQ ID NO 336
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (60)..(65)
<223> OTHER INFORMATION: n is a, c, g, or t

<400> SEQUENCE: 336
gcccaattat ttcaaccagt ttccactgac ttcagcttcc cgatatccga cggtagtgtn     60
nnnnnagaag attcactcaa a                                               81

<210> SEQ ID NO 337
<211> LENGTH: 81
<212> TYPE: DNA
<213> ORGANISM: Artificial Sequence
<220> FEATURE:
<223> OTHER INFORMATION: MIP Sequence
<220> FEATURE:
<221> NAME/KEY: misc_feature
<222> LOCATION: (57)..(62)
<223> OTHER INFORMATION: n is a, c, g, or t

<400> SEQUENCE: 337
ggagaaatgt ctgaggctga atttggcttc agcttcccga tatccgacgg tagtgtnnnn     60
nntggctgcc tttttaggag g                                               81
```